(12) United States Patent
Soane et al.

(10) Patent No.: US 11,634,323 B2
(45) Date of Patent: *Apr. 25, 2023

(54) SYSTEMS AND METHODS FOR PROCESSING GASES

(71) Applicant: TRANSFORM MATERIALS LLC, Riviera Beach, FL (US)

(72) Inventors: David S. Soane, Coral Gables, FL (US); James Nathan Ashcraft, Jupiter, FL (US); Jason Samuel Hummelt, Palm Beach Gardens, FL (US); Mark Ellis Soderholm, Palm Beach Gardens, FL (US); Mathew Leeds, Palm Beach Gardens, FL (US); Alexander Olson Santana, Tequesta, FL (US); Matthew Elijah O'Reilly, Riviera Beach, FL (US)

(73) Assignee: Transform Materials LLC, Riviera Beach, FL (US)

( * ) Notice: Subject to any disclaimer, the term of this patent is extended or adjusted under 35 U.S.C. 154(b) by 772 days.

This patent is subject to a terminal disclaimer.

(21) Appl. No.: 16/548,378

(22) Filed: Aug. 22, 2019

(65) Prior Publication Data

US 2020/0063040 A1 Feb. 27, 2020

Related U.S. Application Data

(60) Provisional application No. 62/721,863, filed on Aug. 23, 2018, provisional application No. 62/736,206, (Continued)

(51) Int. Cl.
*C01B 3/34* (2006.01)
*B01J 19/12* (2006.01)
(Continued)

(52) U.S. Cl.
CPC .............. *C01B 3/34* (2013.01); *B01D 53/047* (2013.01); *B01D 53/14* (2013.01); *B01J 4/002* (2013.01);
(Continued)

(58) Field of Classification Search
CPC ........ C01B 2203/861; C01B 2203/062; C01B 2203/1235; C01B 2203/0277;
(Continued)

(56) References Cited

U.S. PATENT DOCUMENTS 3,519,517 A 7/1970 Dench
3,663,394 A 5/1972 Kawahara
(Continued)

FOREIGN PATENT DOCUMENTS

EP 0461683 A2 12/1991
EP 1936656 A1 6/2008
(Continued)

OTHER PUBLICATIONS

Fincke, J. R., et al., "Plasma Thermal Conversion of Methane to Acetylene," Plasma Chemistry and Plasma Processing, vol. 22, No. 1, Mar. 2002.

(Continued)

*Primary Examiner* — Jafar F Parsa
(74) *Attorney, Agent, or Firm* — Elmore Patent Law Group, P.C.; Mahreen Chaudhry Hoda; Carolyn S. Elmore

(57) ABSTRACT

The invention includes a gas processing system for transforming a hydrocarbon-containing inflow gas into outflow gas products, where the system includes a gas delivery subsystem, a plasma reaction chamber, and a microwave subsystem, with the gas delivery subsystem in fluid communication with the plasma reaction chamber, so that the gas delivery subsystem directs the hydrocarbon-containing inflow gas into the plasma reaction chamber, and the micro- (Continued)

wave subsystem directs microwave energy into the plasma reaction chamber to energize the hydrocarbon-containing inflow gas, thereby forming a plasma in the plasma reaction chamber, which plasma effects the transformation of a hydrocarbon in the hydrocarbon-containing inflow gas into the outflow gas products, which comprise acetylene and hydrogen. The invention also includes methods for the use of the gas processing system.

18 Claims, 16 Drawing Sheets

Related U.S. Application Data filed on Sep. 25, 2018, provisional application No. 62/793,763, filed on Jan. 17, 2019.

(51) Int. Cl.

| | |
|---|---|
| C01B 3/52 | (2006.01) |
| C07C 2/78 | (2006.01) |
| B01D 53/047 | (2006.01) |
| B01D 53/14 | (2006.01) |
| B01J 4/00 | (2006.01) |
| B01J 19/08 | (2006.01) |
| B01J 19/24 | (2006.01) |
| C10G 32/04 | (2006.01) |
| C10G 53/08 | (2006.01) |
| H01J 37/32 | (2006.01) |

(52) U.S. Cl.
CPC ........... *B01J 19/081* (2013.01); *B01J 19/126* (2013.01); *B01J 19/2415* (2013.01); *C01B 3/52* (2013.01); *C07C 2/78* (2013.01); *C10G 32/04* (2013.01); *C10G 53/08* (2013.01); *H01J 37/32192* (2013.01); *B01D 2257/702* (2013.01); *B01J 2219/0004* (2013.01); *B01J 2219/0869* (2013.01); *B01J 2219/0875* (2013.01); *B01J 2219/0894* (2013.01); *B01J 2219/3325* (2013.01); *C01B 2203/142* (2013.01); *C10G 2300/1025* (2013.01); *C10G 2300/201* (2013.01); *C10G 2300/4081* (2013.01); *C10G 2300/80* (2013.01); *H01J 37/32431* (2013.01)

(58) Field of Classification Search
CPC ........ B01D 2257/7022; B01D 2256/24; B01D 53/229; B01D 53/0462; C07C 11/24; C07C 2/76; C07C 2/80; C07C 17/08
See application file for complete search history.

(56) References Cited

U.S. PATENT DOCUMENTS

| | | | |
|---|---|---|---|
| 4,277,773 | A | 7/1981 | Blatnik |
| 4,574,038 | A | 3/1986 | Wan |
| 4,866,346 | A | 9/1989 | Gaudreau et al. |
| 4,975,164 | A | 12/1990 | Ravella et al. |
| 5,015,349 | A | 5/1991 | Suib et al. |
| 5,053,575 | A | 10/1991 | Nikravek et al. |
| 5,131,993 | A | 7/1992 | Suib et al. |
| 5,181,998 | A | 1/1993 | Murphy et al. |
| 5,205,912 | A | 4/1993 | Murphy |
| 5,205,915 | A | 4/1993 | Ravella et al. |
| 5,277,773 | A | 1/1994 | Murphy |
| 5,319,176 | A | 6/1994 | Alvi et al. |
| 5,328,577 | A | 7/1994 | Murphy |
| 5,736,092 | A | 4/1998 | Apte et al. |
| 5,750,823 | A | 5/1998 | Wofford et al. |
| 5,874,705 | A | 2/1999 | Duan |
| 5,972,175 | A | 10/1999 | Tanner et al. |
| 5,993,761 | A | 11/1999 | Czernichowski et al. |
| 6,030,506 | A | 2/2000 | Bittenson et al. |
| 6,099,696 | A | 8/2000 | Schwob et al. |
| 6,156,114 | A | 12/2000 | Bell et al. |
| 6,190,507 | B1 | 2/2001 | Whealton et al. |
| 6,362,449 | B1 | 3/2002 | Hadidi et al. |
| 6,395,238 | B1 | 5/2002 | Rogers et al. |
| 6,409,851 | B1 | 6/2002 | Sethuram et al. |
| 6,582,778 | B2 | 6/2003 | Namiki et al. |
| 6,602,920 | B2 | 8/2003 | Hall et al. |
| 6,696,662 | B2 | 2/2004 | Jewett et al. |
| 6,916,400 | B2 | 7/2005 | Moisan et al. |
| 7,008,970 | B2 | 3/2006 | Kong et al. |
| 7,160,521 | B2 | 1/2007 | Porshnev et al. |
| 7,170,027 | B2 | 1/2007 | Kurashima et al. |
| 7,183,451 | B2 | 2/2007 | Gattis et al. |
| 7,232,975 | B2 | 6/2007 | Kong et al. |
| 7,252,297 | B1 | 8/2007 | Barritt et al. |
| 7,309,471 | B2 | 12/2007 | Benje et al. |
| 7,438,869 | B1 | 10/2008 | Fabian et al. |
| 7,497,922 | B2 | 3/2009 | Kumar et al. |
| 7,915,462 | B2 | 3/2011 | Gattis et al. |
| 7,915,465 | B2 | 3/2011 | Gattis et al. |
| 7,915,466 | B2 | 3/2011 | Gattis et al. |
| 8,636,960 | B2 | 1/2014 | Spitzl et al. |
| 8,680,424 | B2 | 3/2014 | Kobayashi et al. |
| 8,776,719 | B2 | 7/2014 | Radoiu et al. |
| 8,968,588 | B2 | 3/2015 | Zhao et al. |
| 8,974,743 | B2 | 3/2015 | Krull et al. |
| 9,051,526 | B2 | 6/2015 | Markowz et al. |
| 9,095,835 | B2 | 8/2015 | Skoptsov et al. |
| 9,142,389 | B2 | 9/2015 | Wort et al. |
| 9,212,058 | B2 | 12/2015 | de Graffenried, Sr. |
| 9,227,169 | B2 | 1/2016 | Spitzl et al. |
| 9,293,302 | B2 | 3/2016 | Risby et al. |
| 9,308,513 | B2 | 4/2016 | Bricker et al. |
| 9,409,161 | B2 | 8/2016 | Bishop et al. |
| 9,484,191 | B2 | 11/2016 | Winkler |
| 9,573,608 | B2 | 2/2017 | Glass |
| 9,574,086 | B2 | 2/2017 | Johnson et al. |
| 9,623,397 | B2 | 4/2017 | Skoptsov et al. |
| 9,682,359 | B2 | 6/2017 | Skoptsov et al. |
| 9,758,444 | B2 | 9/2017 | Spitzyl |
| 9,767,992 | B1 | 9/2017 | Stowell et al. |
| 9,812,295 | B1 | 11/2017 | Stowell |
| 9,862,602 | B1 | 1/2018 | Riso et al. |
| 9,862,606 | B1 | 1/2018 | Cook et al. |
| 9,909,215 | B2 | 3/2018 | Holber et al. |
| 9,987,611 | B1 | 6/2018 | Strohm et al. |
| 9,997,322 | B2 | 6/2018 | Kong et al. |
| 9,997,334 | B1 | 6/2018 | Anzelmo et al. |
| 10,702,847 | B2 | 7/2020 | Spitzl |
| 2002/0127155 | A1 | 9/2002 | Minaee et al. |
| 2004/0149700 | A1 | 8/2004 | Bayer et al. |
| 2006/0163054 | A1 | 7/2006 | Spitzl et al. |
| 2007/0163678 | A1 | 7/2007 | Kim |
| 2007/0274893 | A1 | 11/2007 | Wright et al. |
| 2008/0029030 | A1 | 2/2008 | Goto et al. |
| 2008/0277265 | A1 | 11/2008 | Tsangaris et al. |
| 2009/0205254 | A1 | 8/2009 | Zhu et al. |
| 2009/0234156 | A1 | 9/2009 | Bartos |
| 2010/0294647 | A1 | 11/2010 | Bayer et al. |
| 2011/0163462 | A1 | 7/2011 | Lang et al. |
| 2011/0190565 | A1 | 8/2011 | Novoselov et al. |
| 2011/0230683 | A1 | 9/2011 | Benje et al. |
| 2012/0034135 | A1 | 2/2012 | Risby |
| 2012/0082913 | A1 | 4/2012 | Hyde et al. |
| 2012/0103790 | A1 | 5/2012 | Krull et al. |
| 2012/0186972 | A1 | 7/2012 | Li et al. |
| 2013/0213795 | A1 | 8/2013 | Strohm et al. |
| 2013/0296458 | A1 | 11/2013 | Krull et al. |
| 2014/0058085 | A1 | 2/2014 | Rende et al. |
| 2014/0159572 | A1 | 6/2014 | Risby et al. |
| 2014/0183033 | A1 | 7/2014 | Spitzl et al. |
| 2014/0239232 | A1 | 8/2014 | Staton et al. |
| 2015/0041309 | A1 | 2/2015 | Spitzl |
| 2015/0044105 | A1 | 2/2015 | Novoselov |
| 2015/0218383 | A1 | 8/2015 | Johnson et al. |

(56) References Cited

U.S. PATENT DOCUMENTS

| | | |
|---|---|---|
| 2015/0258523 A1 | 9/2015 | Skoptsov et al. |
| 2016/0243518 A1 | 8/2016 | Spitzl |
| 2016/0362351 A1 | 12/2016 | Nagaki et al. |
| 2018/0099871 A1 | 4/2018 | Tanner et al. |
| 2018/0138017 A1 | 5/2018 | Stowell |
| 2019/0046946 A1 | 2/2019 | Strohm et al. |
| 2019/0046947 A1 | 2/2019 | Strohm et al. |
| 2019/0185325 A1 | 6/2019 | Tanner et al. |
| 2020/0062591 A1 | 2/2020 | Soane et al. |

FOREIGN PATENT DOCUMENTS

| | | |
|---|---|---|
| GB | 1149473 | 4/1969 |
| RU | 2522636 C1 | 7/2014 |
| WO | 9209351 A1 | 6/1992 |
| WO | 96/41505 A1 | 12/1996 |
| WO | 2004010454 A2 | 1/2004 |
| WO | 2006/037991 A2 | 4/2006 |
| WO | 2006123883 A1 | 11/2006 |
| WO | 2007/086875 A1 | 8/2007 |
| WO | 2010/094969 A1 | 8/2010 |
| WO | 2010/094972 A1 | 8/2010 |
| WO | 2012006155 A1 | 1/2012 |
| WO | 2012/023858 A1 | 2/2012 |
| WO | 2013/149723 | 10/2013 |
| WO | 2016/089994 A1 | 6/2016 |

OTHER PUBLICATIONS

McCarthy, R. L., et al., "Chemical Synthesis from Free Radicals Produced in Microwave Fields," J. Chem. Phys. 22(8): 1360-1365 (1954).

Shen, ChangSheng, et al., "A study on methane coupling to acetylene under the microwave plasma," Science China Chemistry, 53(1): 231-237 (2010).

Spencer, L. F., "The Study of CO2 Conversion in a Microwave Plasma/Catalyst System," A dissertation submitted in partial fullfillment of the requirements for the degree of Doctor of Philosophy (Applied Physics) in The University of Michigan (2012).

Kong, Peter, "Atmospheric-Pressure Plasma Process And Applications," SOHN International Symposium On Advanced Processing of Metals and Materials; Principles, Technologies and Industrial Practice Sep. 2006.

Moisan, M., et al., "An atmospheric pressure waveguide-fed microwave plasma torch: the TIA design," Plasma Sources Sci. Technol., 3: 584-592 (1994).

Abdel-Aal, H. K., et al., "Challenges and Progress in Methane Conversion: An Assesment," Chemical Engineering, 1:1-11 (2016).

Abney, M. B., et al., "Evaluation of Sorbents for Acetylene Separation in Atmosphere Revitalization Loop Closure," 41st International Conference on Environmental Systems Jul. 17-21, 2011, Portland, Oregon, American Institute of Aeronautics and Astronautics.

Abney, M. B., et al., "Hydrogen Purification in Support of Plasma Pyrolysis of Sabatier Derived Methane," 45th International Conference on Environmental Systems Jul. 12-16, 2015, Bellevue, Washington, International Conference on Environmental Systems.

Copenhaver, J., et al., Acetylene and Carbon Monoxide Chemistry, Reinhold Publishing Corporation, New York, NY (1949).

Chaichumporn, C., et al., "Design and Construction of 2.45 GHz Microwave Plasma Source at Atmospheric Pressure," 2nd International Science, Social-Science, Engineering and Energy Conference 2010: Engineering Science and Management, Procedia Engineering 8: 94-100 (2011).

Balachandran, U. (Balu), et al., Hydrogen Separation Membranes, Energy Systems Division, Argonne National Laboratory Annual Report for FY 2010, Report Date: Jan. 31, 2011. http://www.osti.gov/bridge.

Jasiński, M. et al., "Atmospheric pressure microwave plasma source for hydrogen production," International Journal of hydrogen energy, 38: 11473-11483 (2013).

Atwater, J. E., et al., "Development and Testing of a Prototype Microwave Plasma Reactor for Hydrogen Recovery from Sabatier Waste Methane," Downloaded from SAE International by University of Liverpool, Sunday, Sep. 9, 2018.

Bartholome, E., "The BASF-process for production of acetylene by partial oxidation of gaseous hydrocarbons," Special Supplement to Chemical Engineering Science, vol. 3, 1954.

Mostaghimi, J., et al., "Thermal Plasma Sources: How Well are They Adopted to Process Needs?" Plasma Chem Plasma Process, 35: 421-436 (2015).

Blanksby, S. J., et al., "Bond Dissociation Energies of Organic Molecules," American Chemical Research, Accounts of Chemical Research 2002.

Takeuchi, M., et al., "Chemical Reaction of Hydrocarbons in the Microwave Discharge I: On the Mechanism of the Decomposition of Ethane and Ethylene," Bulletin of the Institute for Chemical Research, Kyoto University (1971), 49(4): 230-247.

Scapinello, M., et al., "The panorama of plasma-assisted non-oxidative methane reforming," Chemical Engineering & Processing: Process Intensification, 117: 120-140 (2017).

Chen, C.-K., et al., "Modelling the discharge region of a microwave generated hydrogen plasma," J. Phys. D: Appl. Phys., 32 (1999) 688-698.

Chen, H., L., et al., "Review of plasma catalysis on hydrocarbon reforming for hydrogen production—Interaction, integration, and prospects," Applied Catalysis B: Environmental, 85: 1-9 (2008).

American Chemical Society National Historic Chemical Landmarks. Discovery of the Commercial Processes for Making Calcium Carbide and Acetylene. http://www.acs.org/content/acs/en/education/whatischemistry/landmarks/calciumcarbideacetylene.html (accessed Aug. 20, 2018).

Wang, B., et al., "Conversion of Methane to C2 Hydrocarbons via Cold Plasma Reaction," Journal of Natural Gas Chemistry, 12 (2003)178-182.

Bin, D., et al., "Study on the hydrogenation coupling of methane," Science in China (Series B), 44(2): 191-195 (2001).

Gannon, R. E., "Acetylene From Hydrocarbons," Kirk-Othmer Encyclopedia of Chemical Technology, 2000.

Gruen, D. M., et al., "Carbon dimer, C2, as a growth species for diamond films from methane/hydrogen/argon microwave plasmas," Journal of Vacuum Science & Technology A ,13, 1628 (1995).

Hassouni, K., et al., "Investigation of chemical kinetics and energy transfer in a pulsed microwave H2/CH4 plasma," Plasma Sources Sci. Technol., 10 (2001) 61-75.

Heintze, M., et al., "Mechanism of C2 hydrocarbon formation from methane in a pulsed microwave plasma," Journal of Applied Physics, 92(12), 2002.

Heintze, M., et al., "Methane conversion into acetylene in a microwave plasma: Optimization of the operating parameters," Journal of Applied Physics, 92(5), 2002.

Holmen, A., et al., "Pyrolysis of natural gas: chemistry and process concepts," Fuel Processing Technology, 42 (1995) 249-267.

Huang, J., et al., "Dimerization of Methane through Microwave Plasmas," J. Phys. Chem., 97: 9403-9407 (1993).

Huang, J., et al., "Methane Dimerization Via Microwave Plasmas," Res. Chem. Intermed, vol. 20, (No. 1), pp. 133-139 (1994).

Hunt, J., et al., "Microwave-Specific Enhancement of the Carbon-Carbon Dioxide (Boudouard) Reaction," J. Phy,. Chem. C, 117: 26871-26880 (2013).

Hydrogen from biomethane; gasoline & diesel from tree residue; cellulosic ethanol among new proposed California LCFS fuel pathways (http://www.greencarcongress.com/2015/12/hydrogen-from-biomethane-gasoline-diesel-from-tree-residue-cellulosic-ethanolamong-new-proposed-cal.html), 1-29. Retrieved from the internet May 21, 2018.

Szabó, D., et al., "Microwave Plasma Synthesis of Materials—From Physics and Chemistry to Nanoparticles: A Materials Scientist's Viewpoint," Inorganics, Feb. 2014, 468-507.

Jasiński, M., et al., "Hydrogen Production Via Methane Reforming Using Various Microwave Plasma Sources," Chem. Listy, 102, s1332-s1337 (2008).

(56) References Cited

OTHER PUBLICATIONS

Jasiński, M., et al., "Atmospheric pressure microwave plasma source for hydrogen production," International Journal of Hydrogen Energy XXX, (2013) 1-11.

Jasiński, M., et al., "Production of hydrogen via methane reforming using atmospheric pressure microwave plasma," Journal of Power Sources, 181 (2008) 41-45.

Van den Bekerom, D., et al., "Non-equilibrium Microwave Plasma for Efficient High Temperature Chemistry," J. Vis. Exp. (126), e55066 (2017).

Fincke, J. R., et al., "Thermal Conversion of Methane to Acetylene Final Report," Idaho National Engineering and Environmental Laboratory, Idaho Falls, Idaho. Jan. 2000.

Kawahara, Y., "Decomposition of Hydrocarbons in a Microwave Discharge," The Journal of Physical Chemistry, 73(6) (1969).

Yunpeng, X., et al., "Methane conversion via microwave plasma initiated by a metal initiator," Studies in Surface Science and Catalysis, 2001 Elsevier Science B.V.

Lang, T., "Quasi-equilibria of gaseous species in the C—H system," Diamond and Related Materials, 3 (1994) 470-475.

Marun, C., et al., "Catalytic Oligomerization of Methane via Microwave Heating," J. Phys. Chem. A, 1999, 103, 4332-4340.

Indarto, A., "Methane Conversion in Plasma," Jun. 2010, Retrieved from the Internet <<https://www.researchgate.net/publication/286756315.>>.

Reuter, M. A., "Ulmann's Encyclopedia of Industrial Chemistry," VCH Verlaggesellshaft, Weinheim, Germany, 1990, vol. A16, pp. 375-387. Retrieved from the Internet on Jan. 3, 2015.

Zherlitsyn, A. G., et al., "Microwave plasma torch for processing hydrocarbon gases," Resource-Efficient Technologies, 2 (2016) 11-14.

Minea, T., et al., "Methane activation in a microwave plasma reactor," 22nd International Symposium on Plasma Chemistry, Jul. 5-10, 2015; Antwerp, Belgium.

Moisan, M., et al., "Large Diameter Plasma Generation Using a Waveguide-Based Field Applicator at 2.45 GHz," Journal of Microwave Power and Electromagnetic Energy, 30(1) 1995.

Bullerwell, J., et al., "Stability of acetylene/methane and acetylene/hydrogen/methane gas mixtures at elevated temperatures and pressures," Fuel, 89: 254-256 (2010).

Fridman, A., Plasma Chemistry—Table of Contents, pp. 209-214 and 589-602. Drexel University, Cambridge University Press, www.cambridge.org, (2008).

Snoeckx, R., et al., "Plasma-based liquefaction of methane: The road from hydrogen production to direct methane liquefaction," Plasma Process. Polym, 9999: 1-10 (2016).

Gallon, H. J., "Dry Reforming of Methane Using Non-Thermal Plasma-Catalysis," A thesis submitted to The University of Manchester for the degree of Doctor of Philosophy in the Faculty of Engineering and Physical Sciences, 2010.

Yang, Y., "Direct Non-oxidative Methane Conversion by Non-thermal Plasma: Experimental Study," Plasma Chemistry and Plasma Processing, vol. 23, No. 2, Jun. 2003.

Onoe, K., et al., "Selective synthesis of acetylene from methane by microwave plasma reactions," Fuel, vol. 76, No. 3, pp. 281-282, 1997.

Jasiński, M., et al., "Production of hydrogen via conversion of hydrocarbons using a microwave plasma," Journal of Physics D: Applied Physics, IOP Publishing, 2011, 44 (19).

Whitehead, J.C., et al., "Plasma-catalysis: the known knowns, the known unknowns and the unknown unknowns," J. Phys. D: Appl. Phys. 49 (2016).

Malik, M. A., et al., "Catalyst Enhanced Oxidation of VOCs and Methane in Cold-Plasma Reactors," Platinum Metals Rev., 1999, 43, (3), 109-113.

Ravasio, S., et al., "Analysis of reactivity and energy efficiency of methane conversion through non thermal plasmas," Chemical Engineering Science, 84 (2012) 580-590.

SafetyGram13-Acetylene, Air Products and Chemicals, Inc., 2014.

Suib, S. L., "A Direct, Continuous, Low-Power Catalytic Conversion of Methane to Higher Hydrocarbons via Microwave Plasmas," J. of Catalysis, 139: 383-391 (1993).

Mizeraczyk, J., et al., "Studies of atmospheric-pressure microwave plasmas used for gas processing," NUKLEONIKA, 57(2): 241-247 (2012).

Xu, Yunpeng, "Methane conversion via microwave plasma initiated by a metal initiator," in Studies in Surface Science and Catalysis 136, pp. 75-80. Natural Gas Conversion VI, Proceedings of the 6th Natural Gas Conversion Symposium, 2001, Alaska, USA, Elsevier Science B.V.

Zhang, J.-q., et al., "Non-Oxidative Coupling of Methane to C2 Hydrocarbons under Above-Atmospheric Pressure Using Pulsed Microwave Plasma," Energy & Fuels, 16: 687-693 (2002).

Final Office Action from U.S. Appl. No. 17/402,979, dated Apr. 6, 2022.

Notice of Allowance from U.S. Appl. No. 17/402,937, dated Jun. 14, 2022.

Office Action from U.S. Appl. No. 17/402,937, dated Jan. 5, 2022.

Office Action from U.S. Appl. No. 17/402,979, dated Dec. 9, 2021.

Kovacs, T. et al., "Methane Reformation Using Plasma: An Initial Study", J. Phys. D. Appl. Phys., 39, 2006, 2391-2400.

"Reaktionen gesättigter Kohlenwasserstoffe in der Gasphase und an Oberflächen" Disseratation, 2015.

Gu, Y., "The New Generation Microwave Plasma Assisted CVD Reactor for Diamond Synthesis," A Dissertation Submitted to Michigan State University, 2011.

English translation of Chapter 4 and from "Reaktionen gesättigter Kohlenwasserstoffe in der Gasphase und an Oberflächen" Dissertation, 2015.

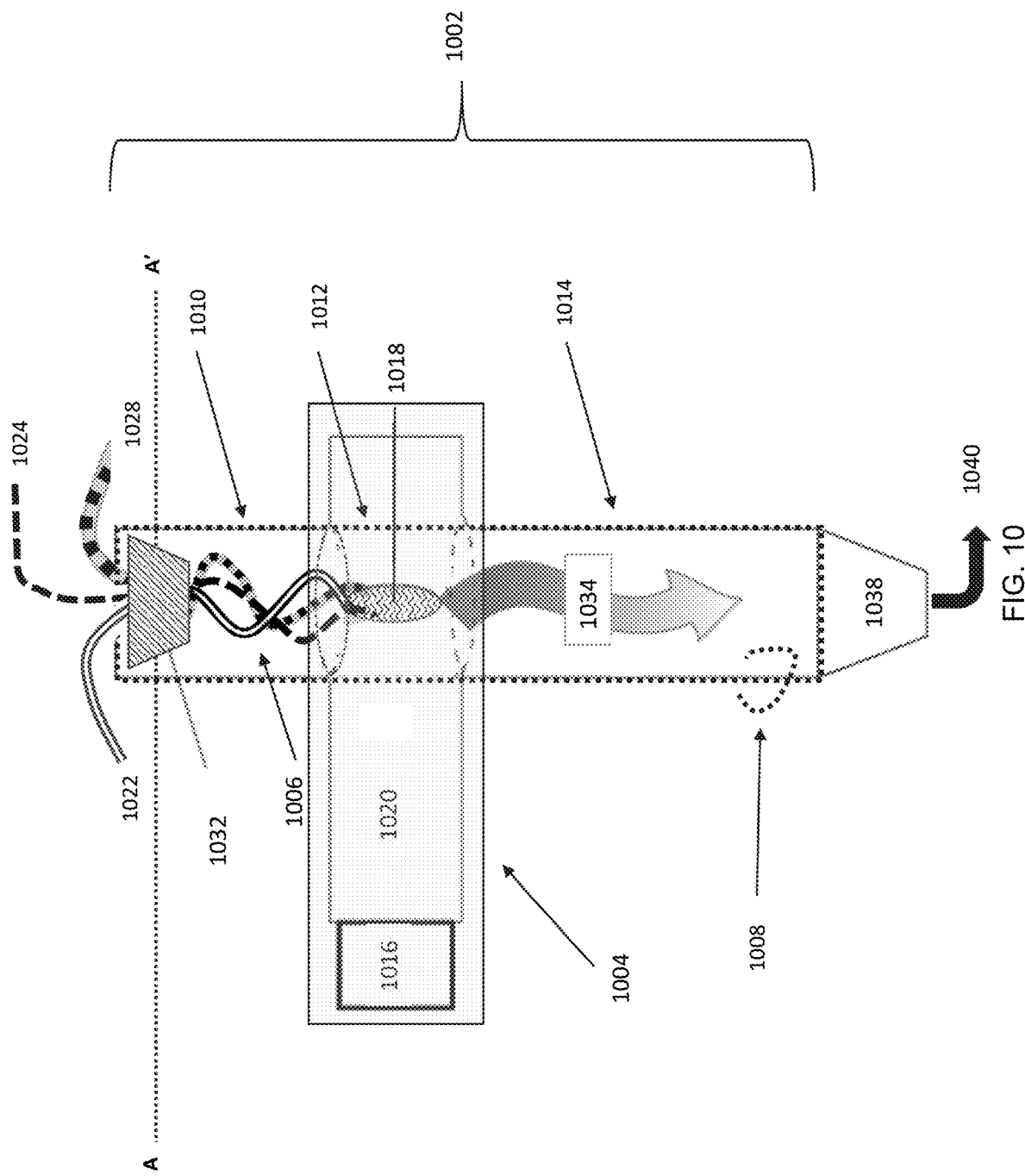

SYSTEMS AND METHODS FOR PROCESSING GASES

RELATED APPLICATIONS

This application claims the benefit of U.S. Provisional Application No. 62/721,863 filed on Aug. 23, 2018, U.S. Provisional Application No. 62/736,206 filed on Sep. 25, 2018, and U.S. Provisional Application No. 62/793,763 filed on Jan. 17, 2019. The entire teachings of each of the above applications are incorporated herein by reference.

BACKGROUND

Acetylene can be used as a chemical precursor or as a feedstock for industrial combustion uses, such as welding and metal cutting. Commercial production of acetylene has been carried out since the early twentieth century. The original method for acetylene production utilized coal as the source material, through a process involving a calcium carbide intermediary. Other methods were developed later in the twentieth century, mainly using heat-based processes such as thermal cracking or electric arc furnaces.

Acetylene produced from coal involves a three-step process: first, coal is heated to produce high-carbon-content coke; second, the coke is heated further in the presence of calcium oxide to yield calcium carbide; third, calcium carbide reacts with water to yield acetylene and calcium hydroxide. The first two steps require very high temperatures, while the last step is exothermic. This method for forming acetylene is still used commercially, especially in China where coal is readily available.

This process, however, carries the impurities of the coal and lime source materials into the final product, so that the resulting acetylene is contaminated with impurities such as phosphines, arsines, and hydrogen sulfate. All of these species are capable of poisoning catalysts for subsequent chemical reactions, so that they need to be scrubbed from the acetylene product before it can be used commercially. Chemical grade acetylene, used for further chemical processing, must be >99.6% pure $C_2H_2$, with <25 ppm phosphine/arsine/$H_2S$. Industrial grade acetylene, which is burned for welding and metal cutting applications, can tolerate more impurities (>98.0 pure $C_2H_2$, <500 ppm phosphine/arsine/$H_2S$). Therefore, the coal-derived production of acetylene is limited in the U.S. to forming industrial grade acetylene; still, even when coal-derived acetylene is just used for welding and metal cutting, the presence of potentially hazardous contaminants raises concerns.

As an alternative, acetylene can be prepared from hydrocarbons by partial oxidation, for example by the process developed by BASF, as described in U.S. Pat. No. 5,824,834. In this process, a hydrocarbon feedstock and oxygen are preheated and then reacted in a combustion chamber, causing the produced gases to reach temperatures >1500° C. The combustion reaction is quenched with water to effect rapid cooling, yielding a gaseous mixture (called "cleavage gas") of acetylene, hydrogen, carbon monoxide, steam and byproducts. This method of acetylene production yields about 7.5% acetylene, along with large quantities of hydrogen (57%), carbon monoxide (26%), and methane (5.2%). One of the byproducts is soot, which needs to be removed from the cleavage gas as it is processed further. Other byproducts include higher-order hydrocarbons, including alkanes, alkenes, alkynes, and aromatics. Removing the impurities from the cleavage gas and recovering the acetylene it contains involve significant engineering challenges.

In addition to the production issues, acetylene is difficult to handle and transport. It is highly explosive. When transported through pipelines, it is kept at a low pressure and is only conveyed for short distances. Acetylene for industrial purposes is pumped into tanks at high pressure and dissolved in solvents, for example, dimethylformamide, N-methyl-2-pyrrolidone, or acetone. When the acetylene cylinder is opened, the dissolved gas vaporizes and flows through a connecting hose to the welding or cutting torch. The entire amount of acetylene in a cylinder is not usable however, because a certain amount remains dissolved in the solvent and is returned to the manufacturer in this state. With the rise of the petrochemical industry in the mid-twentieth century, acetylene continued to be used industrially (i.e., for welding, metal cutting and the like) but it was displaced as a precursor for chemical reactions, replaced by other feedstocks (e.g., ethylene) that were derived directly from oil rather than from coal. As oil has become more expensive and natural gas has become cheaper though, there is increased interest in acetylene as a platform for further chemical processing instead of petroleum-derived feedstocks.

Moreover, the abundance of natural gas is driving the search for more ways to use this material without burning it, to decrease its greenhouse gas effects and to avoid transforming it into $CO_2$, another greenhouse gas, by simple combustion. Increasing demand for non-hydrocarbon sources of fuel supports the use of natural gas as a feedstock for producing hydrogen, which in turn can be used as a source of power. Conventional technologies already exist for extracting hydrogen gas from the methane in natural gas. Steam reforming, for example, can produce hydrogen gas and carbon monoxide; the hydrogen created by the steam reforming process can then be used in pure form for other applications, such as hydrogen fuel cells or gas turbines, in which it combines with oxygen to form water, without greenhouse gas emissions. Other processes, such as partial oxidation, can produce a hydrogen-containing syngas, a combustible mixture that can be used as a fuel. Conventional techniques for producing hydrogen from methane have drawbacks, however. Steam reforming is carried out at high temperatures, and is energy-intensive, requiring costly materials that can withstand the harsh reaction conditions. Steam reforming uses catalysts to effect the conversion of methane to hydrogen, but the catalysts are vulnerable to poisoning by common contaminants. Partial oxidation is a less efficient technique than steam reforming for producing hydrogen, being prone to soot formation, and being limited in hydrogen yield.

Besides natural gas, other mixed gas sources such as oceanic clathrates, coal mine gas, and biogas contain methane gas as well. Biogas is naturally produced mixed gas source that is produced by the anaerobic decomposition of organic waste material in various human-created environments such as landfills, manure holding ponds, waste facilities, and the like, and in natural environments such as peat bogs, melting permafrost, and the like. The anaerobic bacteria that occur in such environments digest the organic material that accumulates there to produce a gas mixture composed mainly of carbon dioxide and methane. Biogas with a high methane content, as can be found in landfill-derived gas mixtures, can be hazardous, because methane is potentially flammable. Moreover, methane is a potent greenhouse gas. Currently biogas that is collected from organic decomposition (e.g., landfills, waste facilities, holding ponds, and the like, or natural regions containing decaying organic materials) can be purified to remove the CO2 and other trace gases, resulting in a high concentration of methane for producing energy. However, simply burning methane-rich biogas produces $CO_2$, another greenhouse gas. It would be desirable to identify uses for biogas or other mixed gas sources that can exploit their energy potential without burning them, to decrease the greenhouse gas effects of methane while avoiding transforming methane into another greenhouse gas, $CO_2$.

There is a need in the art, therefore, for a process that utilizes mixed gas sources such as natural gas or biogas, and/or more purified hydrocarbon feedstocks (e.g., methane, ethane, propane, and butane, and combinations thereof) to form higher-value products. For those processes intended to produce acetylene, it would be advantageous to use mixed gas sources such as natural gas or biogas, and/or more purified hydrocarbon feedstocks (e.g., methane, ethane, propane, and butane) as a feedstock, avoiding the limitations of other mixed gas conversion processes or hydrocarbon combustion processes while taking advantage of the abundance of these feedstock materials. Concomitantly, there is a need in the art for a process that can produce acetylene in a convenient and cost-effective way, using mixed gas sources such as natural gas or biogas, and/or more purified hydrocarbon feedstocks. It would be especially advantageous to produce acetylene with minimal impurities, so that it can be used safely and without substantial additional processing. Furthermore, there is further a need in the art to provide alternative fuels such as hydrogen scalably and efficiently. It would be desirable to carry out these processes in an economic and environmentally responsible way.

In addition, acetylene has utility as a fuel for various industrial applications, for example, metal cutting. This use represents a significant market, comparable in size to various petrochemical uses of acetylene. At present, a major industrial use of acetylene is as a fuel for oxyacetylene torches, used for cutting steel; in addition to cutting, acetylene is used in some welding, carburization, and heat-treating of steel. Oxyacetylene torches burn at a higher flame temperature (3,500° C.) than other oxy-fuel torches, such as oxy-hydrogen (3,000° C.) and oxy-propane (2,500° C.) torches, and oxyacetylene forms a smaller, more precise flame cone. These features allow for higher quality and more precise cutting than other comparable oxy-fuel cutting methods. Additionally, because the combustion of acetylene requires a smaller stoichiometric ratio of oxygen than other fuels like propane, the oxy-acetylene torches consume less oxygen than other oxy-fuel torches, leading to lower oxygen operational costs. Finally, the lower flame temperature and higher oxygen requirements of other hydrocarbon fuel types like oxy-propane torches allow for a higher risk of incomplete combustion, producing hazardous carbon monoxide in the work environment. For the aforesaid reasons, oxyacetylene cutting is standard in the industry for steel cutting.

However, as described previously, there are limitations in the production of acetylene and its transportation. Therefore, sourcing acetylene for industrial cutting is expensive and logistically challenging. First of all, acetylene used as a fuel for torches must be transported and stored in small metal cylinders because of the risk of explosion. In order to reduce the risk of explosion, the acetylene in the cylinders is dissolved in acetone, lowering its partial pressure and thus the likelihood of explosion. Because acetone is present in the cylinders along with acetylene, the acetylene can only be drawn at low flow rates (for example, not to exceed 1/7 of the container contents per hour), to reduce the chance of acetone being drawn into the outflow line along with the acetylene-acetone in the gas feed can diminish flame temperatures and the quality of the cutting process. Even with low rates of outflow, the acetylene in the cylinders can be depleted quickly; once depleted, a cylinder cannot be refilled on-site without extensive safety infrastructure and expertise, again because of the risk of explosion. Because of their small size, cylinders do not scale well for larger operations, but instead must be connected in parallel via manifolding, adding to a project's complexity. Also, because of the risk of explosion, cylinders require a number of safety precautions as they are transported, adding costs and logistical challenges.

There remains a need in the art for a more streamlined, safe method of sourcing acetylene. It would be desirable to circumvent the need for acetone-containing cylinders as the repository for acetylene gas that is used in metal working. For example, it would be useful to have acetylene fuel available on demand and as needed, avoiding the volume and flow rate constraints of cylinder storage. In addition, it would also be advantageous to have acetylene produced in proximity to the point of its use to avoid the cylinder-specific difficulties with transportation.

SUMMARY

Disclosed herein, in embodiments, are gas processing systems for transforming a hydrocarbon-containing inflow gas into outflow gas products, comprising a gas delivery subsystem, a plasma reaction chamber, and a microwave subsystem, wherein the gas delivery subsystem is in fluid communication with the plasma reaction chamber and directs the hydrocarbon-containing inflow gas into the plasma reaction chamber, wherein the microwave subsystem directs microwave energy into the plasma reaction chamber to energize the hydrocarbon-containing inflow gas thereby forming a plasma in the plasma reaction chamber, and wherein the plasma effects the transformation of a hydrocarbon in the hydrocarbon-containing inflow gas into the outflow gas products that comprise acetylene and hydrogen. In embodiments, the hydrocarbon-containing inflow gas can be derived from a mixed gas source, and the mixed gas source can be natural gas or a biogas; in embodiments, the hydrocarbon-containing inflow gas comprises a gas selected from the group consisting of methane, ethane, propane, and butane, and the hydrocarbon-containing inflow gas can consist essentially of methane. In embodiments, the gas delivery subsystem comprises a delivery conduit and a gas injector, wherein the delivery conduit is in fluid communication with the gas injector, wherein the delivery conduit delivers one or more gases to the gas injector, and wherein the gas injector delivers the one or more gases into the plasma reaction chamber. The delivery conduit can comprise a feed gas conveying circuit that delivers the hydrocarbon-containing inflow gas into the gas injector, and the hydrocarbon-containing inflow gas can comprise methane or can consist essentially of methane. In embodiments, the delivery conduit comprises an additional gas conveying circuit that delivers an additional gas into the gas injector, and the additional gas can be hydrogen. In embodiments, the additional gas conveying circuit is an auxiliary gas conveying circuit that delivers an auxiliary gas into the gas injector, or the additional gas conveying circuit is a recycled gas conveying circuit that delivers a recycled gas into the gas injector. The recycled gas can comprise hydrogen, or it can comprise a hydrogen-rich reactant gas which can consist essentially of hydrogen, or the recycled gas can consist essentially of the hydrogen-rich reactant gas.

In embodiments, the delivery conduit delivers each of the one or more gases into the gas injector through a separate pathway. In embodiments, the gas injector comprises an injector body comprising two or more coaxially arranged and separate gas feeds, a first gas feed conveying the hydrocarbon-containing inflow gas into the plasma reaction chamber through a first set of one or more nozzles, and the second gas feed conveying the additional gas into the plasma reaction chamber through a second set of one or more nozzles. In embodiments, at least one of the one or more nozzles is oriented at an angle to a longitudinal axis of the plasma reaction chamber or at an angle to a transverse axis of the plasma reaction chamber. In embodiments, at least one of the one or more nozzles is oriented at an angle to a longitudinal axis or a transverse axis of the injector body. The combined gas flow from the first set of nozzles and the second set of nozzles creates a vortex flow within the plasma reaction chamber. In embodiments, the plasma reaction chamber is disposed within an elongate reactor tube having a proximal and a distal end, and the elongate reactor tube is dimensionally adapted for interaction with the microwave subsystem. The elongate reactor tube can be a quartz tube. The plasma reactor chamber can be disposed approximately at the midportion of the elongate reactor tube. In embodiments, the gas injector conveys the hydrocarbon-containing inflow gas and the additional gas into a proximal portion of the elongate reactor tube wherein the hydrocarbon-containing inflow gas and the additional gas flow distally therefrom towards the plasma reaction chamber. The gas injector can be positioned centrally within the proximal portion, and the first set of one or more nozzles and the second set of one or more nozzles are oriented peripherally; alternatively, the gas injector is positioned peripherally within the proximal portion, and the first set of one or more nozzles and the second set of one or more nozzles are oriented centrally. In embodiments, the microwave subsystem comprises an applicator for directing microwave energy towards the plasma reaction chamber, and the plasma reaction chamber is disposed in a region of the elongate reactor tube that passes through the applicator and intersects it perpendicularly. The applicator can be a single-arm applicator. In embodiments, the microwave subsystem further comprises a power supply, a magnetron, and a waveguide, whereby the power supply energizes the magnetron to produce microwave energy with the microwave energy being conveyed by the waveguide to the applicator, and wherein the applicator directs the microwave energy towards the reaction chamber within the elongate reactor tube, thereby forming the plasma in the plasma reaction chamber. The magnetron can produce L-band microwave energy. In embodiments, the plasma within the plasma reaction chamber produces the outflow gas products, and the outflow gas products flow within the plasma reaction chamber distally towards the distal end of the elongate reactor tube. The outflow products can emerge from the distal end of the elongate reactor tube to enter an effluent separation and disposal subsystem. In embodiments, the effluent separation and disposal subsystem can comprise a solids filter and a cold trap, and/or can comprise an adsorption column, and/or can comprise a pressure swing adsorption system adapted for removing non-hydrogen components from an effluent stream, and/or can comprise a temperature swing adsorption system adapted for removing higher acetylenes from an effluent stream, and/or can comprise an absorption column which in embodiments can absorb acetylene, and/or can comprise a concentrated acid in an amount sufficient to oxidize higher-order hydrocarbons, and/or can comprise a catalyst suitable for converting higher-order hydrocarbons into derivative compounds separable from the effluent stream, and/or can comprise a condenser, and/or can comprise a gas separation membrane array which in embodiments can separate hydrogen from the effluent stream, and/or can comprise a hydrogen separation subsystem which in embodiments can be in fluid communication with the recycled gas conveying circuit wherein hydrogen collected by the hydrogen separation subsystem is recycled into the recycled gas conveying circuit, and/or can comprise an acetylene separation subsystem. In embodiments, the system further comprises a vacuum subsystem that maintains a first reduced pressure environment for the outflow products passing through one or more components of the effluent separation and disposal subsystem The vacuum subsystem can produce a second reduced pressure environment within the elongate reactor tube, and/or it can produce a third reduced pressure environment for the gas delivery subsystem. In embodiments, the vacuum subsystem produces a first, second, and third reduced pressure environment; in embodiments, the first, second, and third reduced pressure environments are within a range of about 30 to about 120 Torr. In embodiments, at least one of the reduced pressure environments is between about 50 to about 100 Torr, or is between about 60 to about 80 Torr. In embodiments, the first, second, and third reduced pressure environments are substantially similar. In embodiments, the system further comprises a cooling subsystem. The cooling subsystem can comprise at least one of a water cooling subsystem and a gas cooling subsystem. In embodiments, the gas cooling subsystem comprises a nitrogen-based cooling circuit, and the nitrogen-based cooling circuit can comprise one or more enclosures for components of the system, whereby the one or more enclosures are sealed sufficiently to enclose nitrogen gas around the components and exclude oxygen therefrom. In embodiments, the system comprises a data management and safety subsystem.

Further disclosed herein are methods for processing a hydrocarbon-containing inflow gas to produce acetylene gas, comprising providing the hydrocarbon-containing inflow gas, injecting the hydrocarbon-containing inflow gas into a reaction chamber, energizing the hydrocarbon-containing inflow gas in the reaction chamber with microwave energy to create a plasma; forming gas products in the plasma, wherein one of the gas products is the acetylene gas; and flowing the gas products to exit the reaction chamber. In embodiments, the hydrocarbon-containing inflow gas is derived from a mixed gas source; the mixed gas source can be natural gas or a biogas. In embodiments, the hydrocarbon-containing inflow gas comprises a gas selected from the group consisting of methane, ethane, propane, and butane, and it can consist essentially of methane. In certain practices, the method further comprises the step of providing one or more additional gases concomitant with the step of providing the hydrocarbon-containing inflow gas, and the one or more additional gases can be selected from the group consisting of hydrogen, nitrogen, and a recycled gas. In embodiments, the recycled gas comprises a hydrogen-rich reactant gas, which can consist essentially of hydrogen. In certain practices, the method further comprises the step of segregating acetylene gas from the gas products following the step of flowing the gas products to exit the reaction chamber. In certain practices, the method further comprises the step of recycling at least one of the gas products. In embodiments, the at least one gas product can comprise hydrogen gas, or can consist essentially of hydrogen gas.

Also disclosed herein are methods for transforming a hydrocarbon-containing inflow gas into an outflow gas, comprising providing the hydrocarbon-containing inflow gas, directing the hydrocarbon-containing inflow gas into the gas processing system as described above, and processing the hydrocarbon-containing inflow gas using the gas processing system described above to transform the inflow gas into the outflow gas, wherein the outflow gas comprises acetylene. In embodiments, the hydrocarbon-containing inflow gas is derived from a mixed gas source, and the mixed gas source can be natural gas or a biogas. In embodiments, the outflow gas further comprises hydrogen.

Disclosed herein, in addition, are metal-cutting systems, comprising the gas processing system as described above, and a storage system for containing the outflow gas products produced by the system; and an apparatus for metal-cutting in fluid communication with the storage system, wherein the apparatus draws the outflow gas products from the storage system and ignites them for use in metal cutting. In embodiments, the apparatus is an acetylene torch or an oxyacetylene torch. In embodiments, the metal-cutting system further comprises a hydrogen separation system in fluid communication with the gas processing system as described above, wherein the outflow gas flows into the hydrogen separation system, wherein the hydrogen separation system separates the outflow gas into two product streams, wherein one product stream is an acetylene-rich gas; and wherein the apparatus for metal cutting uses the acetylene-rich gas stored in the storage system as fuel for metal cutting.

BRIEF DESCRIPTION OF THE FIGURES

FIG. 10 is a schematic diagram of a reaction chamber and its components.

DETAILED DESCRIPTION

Figure 1:
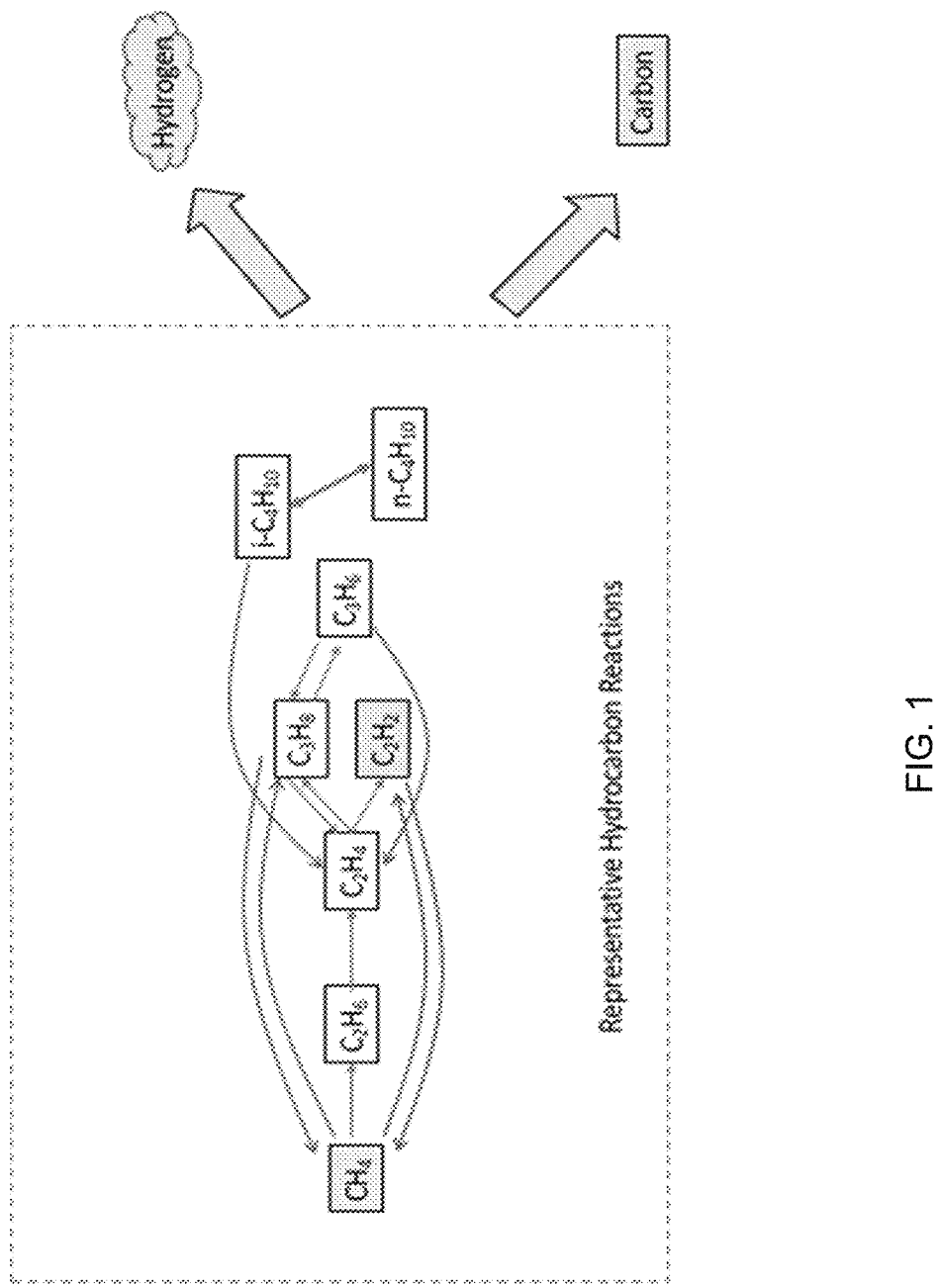
FIG. 1 is a schematic diagram showing various chemical reactions involved in the conversion of methane into hydrogen, carbon, and hydrocarbon products.

Disclosed herein in more detail are systems and methods for converting $C_1$-$C_4$ hydrocarbons, including unsaturated hydrocarbons and saturated hydrocarbons such as methane (as derived from mixed gas sources such as natural gas or biogas for example), into hydrogen, acetylene, and other carbon-based products. In embodiments, these systems and methods use non-thermal plasma produced by microwave energy to effect these conversions. In embodiments, the systems and methods disclosed herein can be optimized ("tuned") to maximize efficient production of acetylene, or of hydrogen, as products that can be isolated for further commercialization; in other embodiments, these systems and methods can be tuned to produce a combination of these gases for specific industrial purposes.

1. Overview a. Non-Thermal Plasmas

Plasma, the fourth state of matter, is an ionized gas: any gas can be turned into a plasma by applying enough energy to it to create a significant density of charged species, i.e., electrons and ions. Plasmas possess some of the properties of gases, but they differ from the ordinary gaseous state because they respond to both electric and magnetic fields, properties that are due to the charged species that exist in the plasma state. Despite having these properties, plasmas are electrically neutral, a characteristic termed quasi-neutrality. In addition to the ions and free electrons from the precursor gas that exist in the plasma, a plasma includes uncharged neutral gas species and precursor molecules that can enter into other chemical reactions. Some weakly ionized gases do not necessarily satisfy all of the conditions of a plasma but may still have many plasma-like qualities that influence their behavior. For example, many of the high-pressure plasmas used in industrial applications fall into this category.

One of the fundamental characteristics of a plasma is its temperature. Plasmas have been used in chemical and industrial applications because they can generate temperatures much greater than those obtained in traditional chemical engineering processes. In a plasma, energy is transferred to electrons, which in turn transfer energy to heavier particles through collisions. Electrons have a higher temperature than heavier particles, and an equilibrium temperature is reached that reflects the collisional frequency and radiative processes of the various particles in the plasma. Those plasmas having an electron temperature ($T_e$) that is close to that of the heavy particles' translational temperature ($T_0$) are defined as thermal plasmas, with gas temperatures greater than 3,000 K. By contrast, in non-thermal plasmas, highly energetic electrons can co-exist with species having substantially lower temperatures. Therefore, the translational temperature $T_0$ of the non-thermal plasma can be much lower than the electron temperature $T_e$ of the plasma—$T_e$ can be close to 11,600 K in industrial plasmas or even higher in other types of plasmas.

The energy situation in a plasma is more complex when the plasma contains molecules (such as $H_2$, $N_2$, or $CH_4$) instead of just atoms. These molecules have the ability to store energy in various rotational and vibrational motions, and therefore have rotational and vibrational temperatures associated with them. These temperatures for such plasmas generally lie in between the translational and electron temperature of the plasma, and they can affect the behavior of the plasma and its associated chemistry. The techniques disclosed herein are based on the ability of a non-thermal plasma to transfer the major portion of the electrical input energy to energetic electrons in the constitutive feed gas, rather than heating the gas itself. Through electron impacts, ionization, dissociation, and excitation, charged atomic and molecular species (e.g., electrons, ions, radicals) are generated that can participate in chemical reactions.

Methane is particularly resistant to chemical conversion because of its stability: breaking the C—H bonds in methane requires an enthalpy change of 1664 kJ mol$^{-1}$. Using the techniques described below, a non-thermal plasma can be produced and harnessed to break bonds in $C_1$-$C_4$ hydrocarbons, including methane bonds, and create acetylene and hydrogen molecules with high efficiency and selectivity.

b. Microwave Plasma Generation

In embodiments, the plasma used for these systems and methods is a microwave plasma, formed by directing microwave energy at the methane-containing feed gas, as described below in more detail. While methane is used as an exemplary embodiment in this description, it is understood that other short-chain alkanes (e.g., ethane, propane, butane) can be used as feed gases as well, either as single gas feed gases, or in combination with each other or with methane.

The microwave plasma process described herein is a gas phase process, using gaseous reactant precursors to form desired gaseous products. Because of the very fast oscillation frequency of the electric field relative to the molecular and electronic collision frequencies, microwave-generated plasmas are often in a high degree of non-equilibrium, meaning that electron and vibrational temperatures can be much greater than the gas temperature. In embodiments, collisions between the charged species (electrons, ions) and uncharged species (molecules, atoms, particles) in the microwave plasma transfer energy: this microwave-energized plasma supports a highly reactive chemical environment because of the energy contained in the plasma's free electrons. Because of the high degree of ionization of the precursor gas, the chemical dissociation and ionization of intermediates, and the elevated vibrational and excitational energies in the plasma, the desired chemical reactions described below proceed rapidly and efficiently.

Without being bound by theory, microwave radiation is understood to act as follows to create a plasma from a gaseous precursor. When the precursor gas (e.g., methane) is subjected to microwave radiation that meets or exceeds the dielectric strength of such gas, a free electron (present from background radiation or other sources) in the microwave field region is able to gain enough energy from the microwave electrical field in between collisions with neutral molecules that it can ionize another atom or molecule. The secondary ionized electron is subsequently accelerated in a direction that is governed by the electric field of microwave radiation, and it gains energy too until it causes another ionization event. This process of ionization progresses throughout the microwave field region until a steady state is reached. The final number of electrons in the plasma is determined mainly by the electron loss processes of the plasma, such as diffusion, recombination, and attachment.

The systems and methods disclosed herein use $C_1$-$C_4$ hydrocarbons, such as methane, as the reactant precursor gas that is subjected to microwave radiation. Methane may be used to exemplify a reactant precursor gas suitable for use in these systems and methods.

Methane dissociation in the plasma, initiated by collisions with the energized electrons as described above, results in the formation of $CH_x$ radicals. The major initial reaction is the breaking of the C—H bonds in methane, with resultant formation of CH3*, CH2*, CH*, H*, and C. These radicals can recombine to form two-carbon fragments as exemplified by the following equations:

$$CH_3^* + CH_3^* \rightarrow C_2H_6$$

$$CH_2^* + CH_2^* \rightarrow C_2H_4$$

$$CH^* + CH^* \rightarrow C_2H_2$$

$$CH_3^* + CH^* \rightarrow C_2H_4$$

$$CH_3^* + CH_2^* \rightarrow C_2H_4 + H^*$$

$$CH_3^* + CH^* \rightarrow C_2H_4$$

$$CH_3^* + CH^* \rightarrow C_2H_2 + H_2$$

$$CH_2^* + CH^* \rightarrow C_2H_2 + H^*$$

In addition, methane can combine with various radicals to form two-carbon fragments as exemplified by the following equations:

$$CH_4 + CH_3^* \rightarrow C_2H_6 + H^*$$

$$CH_4 + CH_2^* \rightarrow C_2H_6$$

$$CH_4 + CH_2^* \rightarrow C_2H_4 + 2H^* / H_2 CH_4 + CH^* \rightarrow C_2H_4$$

$$CH_4 + CH^* \rightarrow C_2H_2 + H^* + H_2$$

Besides the illustrated reactions to form two-carbon fragments and hydrogen, higher-order hydrocarbons can be formed by recombinations of plasma-generated radicals with each other and with the precursor gas. As used herein, the term "higher-order hydrocarbon" refers to any hydrocarbon having 3 or more carbon atoms, whether saturated or unsaturated, including aromatics.

Furthermore, complete dehydrogenation of methane can take place, resulting in the formation of elemental carbon and hydrogen gas. Representative reactions are show in FIG. 1. As shown in FIG. 1, a number of exemplary reactions producing hydrocarbons are shown within the dotted line, while the elemental products (hydrogen and carbon) are shown outside the dotted line.

In embodiments, parameters can be optimized to maximize acetylene formation. In other embodiments, parameters can be optimized to maximize hydrogen formation. As a general principle, for example, if the feed gases entering the plasma reaction chamber include less hydrogen as compared to hydrocarbon input, the output will be more hydrogen formed, potentially in combination with more carbon solids. Following this principle, in order to maximize hydrogen formation, a pure hydrocarbon feed could be used, and more of the desired hydrogen would be produced, along with a quantity of carbon solids. Factors affecting product selectivity (e.g., allowing the preferential formation of acetylene over other species, or allowing the preferential formation of hydrogen over hydrocarbon products) include, without limitation, the identity of the reactant precursor gas, the addition of other gases to the system, the flow rate of any gases entering the system, the temperature and pressure in the reactor system, the amount of microwave power and flow geometry used to create the plasma, the energy density in the reaction zone, the arrangement of the electrical field surrounding the plasma, and reactor vessel geometry and dimensions. In embodiments, static electric and magnetic fields can be employed to influence the behavior of the plasma and hence the product selectivity.

c. Precursor Gases

For the systems and methods disclosed herein, $C_1$-$C_4$ alkane hydrocarbons (for example, methane, ethane, propane, and butane) or other hydrocarbon gases can be used alone or in combination with other gases as precursor gases. In an embodiment of these systems and methods, methane is the main precursor gas. In embodiments, it can be combined with hydrogen and/or nitrogen as it enters the plasma reaction chamber, forming a single gas mixture that is energized to the plasma state. In embodiments, methane enters the plasma reaction chamber through its own set of nozzles, while other gases (such as hydrogen and/or nitrogen) are added to the plasma reaction chamber separately, through a different set or sets of nozzles. Methane can be used in a pure state, or it can be introduced into the system as a component of a commercially available gas stream.

Mixed gas sources such as natural gas or biogas are particularly advantageous sources of this precursor gas. As used herein, the term "biogas" refers to a mixed gas produced by the anaerobic decomposition of organic waste material in various natural or manmade environments; the term "biogas" includes all those natural or man-made environments in which such gas-producing anaerobic decomposition can take place, e.g., landfills, manure holding ponds, municipal waste sites, sewage treatment facilities, agricultural waste sites, permafrost decay, and the like. Biogas as collected or retrieved from those sites can be treated or upgraded to increase its methane content and to remove impurities, so that it becomes especially suitable as a precursor gas for the systems and methods disclosed herein.

Biogas, produced from raw materials such as municipal waste, agricultural waste, plant material, sewage, manure, food waste or other natural or manmade organic sources, is typically formed in a closed system via the anaerobic digestion or fermentation of the organic material. The first stage of this process is hydrolysis, in which the insoluble organic polymers are broken down into sugars and amino acids that serve as substrates for the activity of the anaerobic acidogenic bacteria. In a second stage, these bacteria convert the sugars and amino acids into carbon dioxide, hydrogen, ammonia, and organic acids; the acidogenic bacteria further convert the organic acids into acetic acid, ammonia and carbon dioxide. As a third stage, a separate population of anaerobic bacteria, the methanogens, convert these fermentation products into methane and carbon dioxide. Biogas, containing a mixture of methane and carbon dioxide along with gaseous byproducts such as hydrogen sulfide, can be collected and treated to remove carbon dioxide and the undesirable gaseous products, leaving a gaseous mixture with a high concentration of methane that is suitable for energy production or for further processing. Methane in biogas is concentrated using a process of biogas upgrading, resulting in a product that has similar performance characteristics to fossil-derived natural gas.

Processes such as water washing, adsorption, membrane separation, amine gas treatment, and the like, can be used for biogas upgrading. Upgrading processes can advantageously be carried out to remove oxygen from the biogas before it is used as a gas source. Oxygen in the feed gas can render it vulnerable to combustion; moreover, oxygen can corrode equipment used in the plasma-based hydrocarbon processing system as disclosed herein. Furthermore, under certain circumstances, oxygen removal may be necessary to meet regulatory standards or other purity requirements. A number of oxygen removal technologies are suitable for use with biogas. As an example, oxygen can be reacted with a reduced metal species, thus oxidizing the metal and consuming the oxygen. The oxidized metal species will then be regenerated back to the active form by reducing the metal species by passing a hydrogen or carbon monoxide containing gas stream over the metal species, generating water or carbon dioxide, respectively. Metal species such as palladium or nickel could be used to catalytically combust oxygen at >500° F. with hydrocarbon species mixed with the $O_2$. As another approach, solid scavengers can be used in a disposable fashion to trap oxygen. For example, $Fe_2S_3$ can react with three molar equivalents of molecular oxygen to form rust and elemental sulfur. As yet another approach, oxygen can be separated from other gases by molecular sieves, such as 5 A or 13X molecular sieve, similar to the technology seen in air separation units (ASUs). Other upgrading processes for biogas would be available to skilled artisans using no more than routine experimentation. Upgraded biogas can reach a purity and quality similar to the natural gas in U.S. pipelines, and can be used for the same purposes.

Natural gas as extracted from the earth is predominantly methane, making it a useful source of precursor gas for these systems and methods. Typically, it also includes higher-order hydrocarbons such as ethane, propane, butane, and pentane, along with non-hydrocarbon impurities. The table below (Table 1) illustrates an exemplary composition of natural gas.

TABLE 1

| Methane | $CH_4$ | 70-90% |
|---|---|---|
| Ethane | $C_2H_6$ | 0-20% |
| Propane | $C_3H_8$ | |
| Butane | $C_4H_{10}$ | |
| Carbon Dioxide | $CO_2$ | 0-8% |
| Oxygen | $O_2$ | 0-0.2% |
| Nitrogen | $N_2$ | 0-5% |
| Hydrogen sulfide | $H_2S$ | 0-5% |
| Rare gases | Ar, He, Ne, Xe | Trace |

Source: http://naturalgas.org/overview/background

Natural gas is generally processed to remove most of the non-methane components before it is made available for commercial or residential use, so that it is almost pure methane when it is reaches the consumer. As an example, natural gas available commercially can include about 96% methane. While an extensive system of pipelines exists in the United States to bring natural gas to consumer markets after it has been stripped of its impurities, much natural gas is found in areas that are far from these markets and far from the pipeline infrastructure (often termed remote or "stranded" natural gas). In embodiments, the systems and methods disclosed herein can be used in situ, for example at the location of the stranded natural gas, to convert it into acetylene and other useful products; these systems and methods accordingly offer a cost-effective way to utilize this stranded natural gas as a resource.

2. Systems and Subsystems

In embodiments, the plasma-based hydrocarbon processing system as disclosed herein can comprise six subsystems: 1) a gas delivery subsystem, 2) a microwave subsystem, 3) a vacuum subsystem, 4) a cooling subsystem, 5) an effluent separation and disposal subsystem, and 6) a data management and safety subsystem. These subsystems are described in more detail below. The integration of these subsystems is shown schematically on FIG. 2. Desirable outputs from these subsystems and methods can include a high degree of methane conversion, and a high degree of acetylene selectivity and/or a high degree of hydrogen selectivity.

Figure 2:
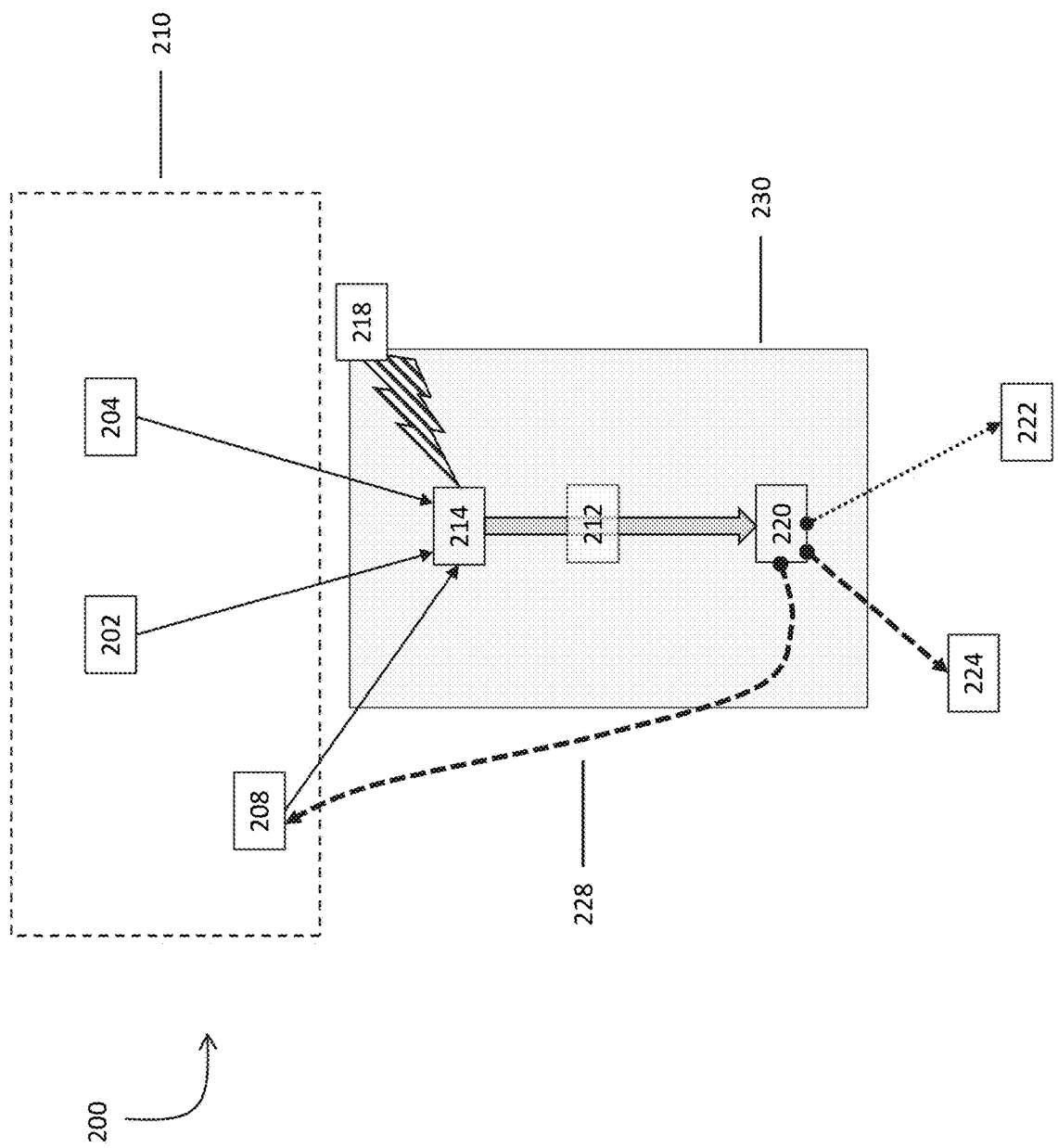
FIG. 2 depicts schematically a plasma-based hydrocarbon processing system and component subsystems.

As shown schematically in FIG. 2, a plasma-based hydrocarbon processing system 200 provides for the conversion of one or more inflow gases 202, 204, and 208 into a mixture of gaseous products contained in an outflow stream 212 emerging from a plasma reaction chamber 214, where the plasma reaction chamber contains the plasma that has been generated by a microwave subsystem 218. In the depicted embodiment, a hydrocarbon inflow gas 202, such as methane, enters the plasma reaction chamber 214 separately from the hydrogen-containing inflow gas 208 that is produced from a recycling of a certain fraction of the outflow stream 212. An optional auxiliary gas 204 such as nitrogen can be introduced separately as shown, or it can be mixed with one or both of the other inflow gases 202 and 208. The various inflow gas streams and their direction into the plasma reaction chamber 214 are encompassed by the gas delivery subsystem 210. The gas delivery subsystem 210 is responsible for producing the appropriate proportions of inflow gases and controlling their flow rates. Once the inflow gases enter the plasma reaction chamber 214, they are energized by microwaves produced by the microwave subsystem 218, which creates a plasma state within the plasma reaction chamber 214. An outflow stream 212 carries outflow (or "produced") gas products including acetylene, hydrogen, and a mixture of unreacted methane and higher-order hydrocarbons. Carbon solids can be entrained by the outflow gas stream 212. An effluent separation and disposal subsystem 220 allows for the separation of waste components from the outflow stream 212 so that they can be disposed of, and further allows for the separation of desirable components into discrete streams as necessary for further commercialization or for reintroduction into the plasma reaction chamber 214 as an inflow gas 208. For example, acetylene 224 can be separated from the outflow stream 212 in the separation/disposal subsystem 220, and it can be used commercially. In embodiments, for example, the acetylene can be further purified for use in chemical reactions. In other embodiments, the acetylene can be further processed, either to form other compounds or to form elemental carbon for other uses or for disposal. In embodiments, the carbon solids entrained by the outflow gas stream 212 can be removed by the separation/disposal subsystem 220 as a discrete product or waste material 222. In the depicted embodiment, a recycled stream 228 that is predominately hydrogen emerges from the separation/disposal subsystem and is recycled back into the plasma reaction chamber 214 as an inflow gas 208. In other embodiments, a portion or the entirety of hydrogen produced by the reactor can be separated from the outflow stream 212 and commercialized separately. In yet other embodiments, the separation of outflow stream 212 components proceeds differently: for example, carbon can be separated entirely, with a mixed hydrogen and hydrocarbon gas stream being segregated for commercialization or other uses. The separation/disposal subsystem can be configured to segregate single gases or gas mixtures in accordance with specific gas processing goals. As shown schematically in FIG. 2, a vacuum subsystem 230 surrounds certain system components to maintain them at a low pressure. A cooling subsystem (not shown) provides appropriate cooling for each system component.

In embodiments, a number of system parameters can be modified to optimize hydrocarbon (e.g., methane) conversion rate and acetylene or hydrogen selectivity, including input gas flow rate (SLM), input pressure, and power per converted hydrocarbon (e.g., methane). Table 2 shows the effect of varying these parameters. A useful metric for comparing results of different system parameters is efficiency, calculated as the energy used per molecule of methane converted ($eV/CH_4$). This metric is easily applied to both industrial uses, such as production cost per kg of product, and scientific uses, such as comparing against bond strengths and calculating thermodynamic efficiency.

TABLE 2

|  | 1 | 2 | 3 |
|---|---|---|---|
| Reactor I.D. (mm.) | 108 | 108 | 108 |
| $CH_4/H_2/N_2$ Feed flow (SLM) | 383/460/38 | 367/550/37 | 338/676/34 |

TABLE 2-continued

|  | 1 | 2 | 3 |
|---|---|---|---|
| Pressure (Torr) | 40 | 42 | 52 |
| $eV/CH_4$ | 3.90 | 4.07 | 4.42 |
| Effluent (SLM) | 1226 | 1285 | 1353 |
| $CH_4/H_2/N_2/C_2H_2$ Effluent (%) | 1.6/81.5/ 3.1/13.8 | 1.4/83.1/ 2.9/12.6 | 1.2/85.2/ 2.6/11 |
| $C_2H_2$ Selectivity (%) | 93 | 93 | 93 | a. Gas Delivery Subsystem

In embodiments, a gas delivery subsystem is constructed to direct inflow gases into the plasma reaction chamber. The gas delivery subsystem comprises two components, the delivery conduit and the gas injector. Included in the description of this subsystem are further descriptions of (i) gases fed into the reactor (inflow gases); (ii) the delivery conduit for conveying inflow gases into the plasma reaction chamber, where the delivery conduit includes one or more separate circuits (or "conveying circuits") for gas flow, and where the conveying circuits can include a main feed gas conveying circuit, auxiliary gas conveying circuits for additional gases besides the main feed gas, and/or a recycled gas conveying circuit to allow return of one or more produced gases (e.g., hydrogen) to be used as inflow gases for subsequent reactions, and (iii) the gas injector assembly in fluid communication with the delivery conduit and its component conveying circuits that introduces component inflow gases into the plasma reaction chamber itself i. Inflow Gases Inflow gases can comprise precursor reactant gases such as $C_1$-$C_4$ alkane hydrocarbons in various combinations. Precursor reactant gases are those that provide hydrogens or carbons for further reactions in the plasma state. In embodiments, the inflow gases are methane and hydrogen, with nitrogen optionally combined with the methane. In certain embodiments, methane and hydrogen are reactants. The proportions of reactant gases, along with the optional nitrogen additive, can be varied empirically to optimize the product profile and yield.

Inflow gases used by the plasma-based hydrocarbon processing system can be supplied directly from feed tanks, feed lines, and/or through recycling. As used herein, the term "inflow gas" means any gas that is added to plasma reaction chamber within which the plasma is formed. An inflow gas may be a reactant gas such as methane or hydrogen, which is transformed by the plasma state into various products, as described in FIG. 1. An inflow gas may be an auxiliary additive gas such as nitrogen. An inflow gas can be supplied from external gas sources called "feed lines," or from intrasystem recycling, wherein a gas produced by the system is reintroduced in whole or in part into the plasma reaction chamber for subsequent reactions.

An inflow gas entering the system via an external gas source or feed line can be derived from a gas reservoir such as a storage tank, or it can be derived from an extrinsically situated flowing gas lines such as a mixed gas source line (e.g., a natural gas line or biogas line). In embodiments, the inflow gas contains solely (or substantially only) the reactants methane and hydrogen, with no deliberately added additional gaseous additives. The methane in the inflow gas can be obtained as a component of a more complex flowing gas mixture such as natural gas or biogas. In embodiments, methane and, optionally nitrogen, are fed in from feed lines (i.e., storage tanks or flowing gas lines), while hydrogen can be fed in from a storage tank or it can be recycled from the product stream and directed back into the reactor.

A recycled gas stream used for intrasystem recycling is an effluent (i.e., outflow gas) from the plasma reaction chamber, optionally separated into various component gases, with some or all of this gas or these gases reintroduced into the plasma reaction chamber. In embodiments, the hydrogen in the outflow gas products stream is separated from other gases and is recycled in a purified form. In embodiments, a hydrocarbon inflow gas is introduced into the plasma reaction chamber via a flowing gas feed line, for example a natural gas line or biogas line, while hydrogen is introduced into the plasma reaction chamber separately from the hydrocarbon inflow; this hydrogen can be derived in whole or in part from a recycled gas stream.

In embodiments, the recycled gas can comprise a hydrogen-rich reactant gas, wherein hydrogen is the main component, with some hydrocarbons also present that are capable of reactions. A hydrogen-rich reactant gas can consist essentially of hydrogen, i.e., can include about 95% hydrogen or greater, or about 96% hydrogen or greater, or about 97% hydrogen or greater, or about 98% hydrogen or greater, or about 99% hydrogen or greater. In embodiments, the hydrogen-rich reactant gas comprises about 90% of the recycled gas or more, or about 91% of the recycled gas or more, or about 92% of the recycled gas or more, or about 93% of the recycled gas or more, or about 94% of the recycled gas or more. In embodiments, the recycled gas consists essentially of the hydrogen-rich reactant gas, i.e., the hydrogen-rich reactant gas comprises about 95% of the recycled gas or more, or about 96% of the recycled gas or more, or about 97% of the recycled gas or more, or about 98% of the recycled gas or more, or about 99% of the recycled gas or more. In embodiments, the recycled gas comprises a non-reactant gas such as nitrogen in addition to the hydrogen-rich reactant gas. In embodiments, the remainder of the recycled gas apart from the hydrogen-rich reactant gas is nitrogen. In other embodiments, nitrogen is added as a separate auxiliary gas, apart from its presence or absence in the recycled gas. Volumes of hydrogen and nitrogen used in the system can be expressed in relation to the total methane flow. For example, the following ratio of inflow gas feeds can be used: 1:0-3:0.1 methane:hydrogen:nitrogen; in other embodiments, the following ratio of inflow gas feeds can be used: 1:1-2:0.1 methane:hydrogen:nitrogen. In embodiments, similar ratios of methane and hydrogen can be used in the absence of nitrogen. In an embodiment, a methane flow into the reactor of 300-400 SLM (approximately 11-14 SCFM) can be used. In an embodiment, a methane flow of about 380 SLM (13.4 SCFM) can be used. In embodiments, these flows are suitable for a reactor power of 100 kW.

In embodiments, the amount of hydrogen entering the reactor can be varied in order to select for more or less acetylene production. Increasing the amount of hydrogen entering the reactor increases the amount of this gas available for reacting with methane, thereby improving the conversion selectivity for acetylene production and decreasing the amount of undesirable soot build-up. In embodiments, an increased amount of hydrogen entering the reactor decreases the amount of ethylene in the outflow, as compared to acetylene.

In embodiments, hydrogen is provided from hydrogen cylinders. In other embodiments, hydrogen can be provided by recycling hydrogen that is produced by the overall system: in other words, hydrogen produced from a $C_1$-$C_4$ hydrocarbon feedstock such as methane in the plasma reaction can be reused as a reactant. In certain embodiments, a recycled gas conveying circuit that conveys hydrogen as an inflow gas back into the system can be combined with a separate inflow source of hydrogen, for example from a hydrogen feed tank to tune the input of this gas. This approach can be advantageous at certain times during the production cycle, for example at system start-up when no recycled hydrogen has yet been produced, or to keep hydrogen inflow at a constant level despite variations in hydrogen produced during recycling.

In an embodiment, the gas delivery subsystem can be precharged, for example, at system start-up, to balance the mixing of gases and to harmonize the gas flow with the microwave energy. First, the system can be evacuated and set at a near-vacuum pressure. Second, the system can be filled from an external source of hydrogen, either backfilled via hydrogen introduced retrograde into the recycled gas conveying circuit, or front-filled from a separate hydrogen inflow line. Third, a $C_1$-$C_4$ hydrocarbon (e.g., methane) or $C_1$-$C_4$ hydrocarbon/nitrogen mixture can be added as an inflow gas, with flows measured by flowmeters. With the system thus precharged with appropriate gases, the reactor can be energized, and the inflow gases can be processed. As the inflow gases are processed in the plasma reaction chamber, hydrogen is generated in the outflow gas products stream, along with other gas products. Hydrogen captured from the outflow gas products stream then can be recycled into the system, while at the same time the exogenous hydrogen inflow is decreased. This balancing of extrinsic and intrinsic hydrogen inflows (from external feed lines and from recycling) can facilitate a smooth start-up procedure for the overall system.

In embodiments, methane is the main component of the hydrocarbon containing inflow gas for the plasma-based hydrocarbon gas processing described in these systems and methods. In embodiments, methane can be introduced from gas cylinders, from pipelines, or from an inflow of a mixed gas (e.g., natural gas or biogas) as described previously. A set of compressors can be used, so that methane is introduced at a correct pressure, for example at a feed pressure of at least about 2 atm. If natural gas or biogas is used to provide the methane feed gas, the amount of available methane can be monitored, for example by using a benchtop gas chromatograph, and the impurities in the natural gas can be identified and removed. For example, if the natural gas or biogas feed contains sulfur, it can affect the purity of the acetylene product stream; such an impurity must be removed before processing. Various impurities that are commonly found in natural gas or biogas (e.g. carbon dioxide, mercaptans, hydrogen sulfide, and the like) can be removed with a series of pre-scrubbers, where the type of scrubber selected depends on the impurity to be removed.

Desirably, a mixed gas comprising methane can include a high concentration of methane, so that it is substantially free of impurities or other gases. Natural gas derived directly from a natural source without commercial treatment can contain about 90% or greater of methane. However, natural gas that is processed to be available commercially, or equivalently treated biogas, can be substantially free of non-methane gases and impurities. A hydrocarbon-containing inflow gas from such a source is deemed to consist essentially of methane, which term refers to an inflow gas containing about 95% of methane or greater. Such a gas, consisting essentially of methane, can contain, for example, about 95% methane or greater, or about 96% methane or greater, or about 97% methane or greater, or about 98% methane or greater, or about 99% methane or greater. Gases provided from natural sources such as in situ natural gas (as found in wells prior to processing) or such as biogas may contain lesser amounts of methane, but they can be pretreated for use as a hydrocarbon-containing inflow gas so that such gases have higher concentrations of methane; in embodiments, such pretreated gases consist essentially of methane when used as hydrocarbon-containing inflow gases for these systems and methods.

In embodiments, other auxiliary gases can be used as components of or additives to the inflow gas stream, for example additives such as nitrogen, carbon dioxide, and/or other reactive or inert gases. In an embodiment, nitrogen can be optionally used as a component of the inflow feed gas; it can also be used as a sealing gas for the vacuum pumps, as described below. In an embodiment, the inflow feed gas contains about 10% nitrogen, although this amount may be varied or tuned to optimize efficiency and selectivity for acetylene production; in other embodiments, nitrogen may be present in amounts ranging from about 0% to about 10%, with the nitrogen either deliberately added or extraneously present, for example as a minor component adventitiously found the feed gas. In other embodiments, no additional nitrogen is included. In addition to its use as an inflow gas component, nitrogen in gas and liquid form can be used as a part of the cooling subsystem to cool various components and provide a nitrogen "buffer" around the reactor, as described below. Carbon dioxide can be included as a separate component of the inflow gas, or it can be mixed into the reactor effluent to serve as an internal standard for gas chromatographic analysis of that effluent. In an embodiment, carbon dioxide is added to the effluent in the amount of 30% of the methane feed in order to achieve good precision in downstream gas chromatography measurements. Other auxiliary gases may be used as inflow gases along with the reactant gases, for example helium for gas chromatography and argon.

ii. Gas Delivery Conduit

The gas delivery conduit conveys the various inflow gases (including reactant gases, additive or auxiliary gases, and recycled gases) into the gas injector; the gas injector delivers the various inflow gases into the plasma reaction chamber. The gas delivery conduit contains conveying circuits dedicated to specific gas streams: the feed gas is carried within the feed gas conveying circuit, additional gases are carried by one or more additional gas conveying circuits, recycled gas(es) are carried by one or more recycled gas conveying circuits. In embodiments, these systems and methods use a hydrocarbon-bearing inflow stream as a main gas feed, for example, a methane stream or a mixed gas stream (e.g., natural gas or biogas), with the main gas feed being carried by the feed gas conveying circuit. In embodiments, additional gas streams can also pass through the gas delivery conduit in addition to the main gas feed, adding inert gases such as nitrogen, and/or adding reactants such as hydrogen as separate streams via their designated conveying circuits. Furthermore, in embodiments, a recycled gas stream can be added to the mix through a recycled gas conveying circuit, as described in more detail below; a recycled gas stream can contain hydrogen as the predominant component, along with small quantities of unreacted methane and other hydrocarbon components. In embodiments, each conveying circuit is in fluid communication with the gas injector assembly and conveys its gas separately into the gas injector assembly, for example through a dedicated nozzle, valve, or conduit.

Figure 3:
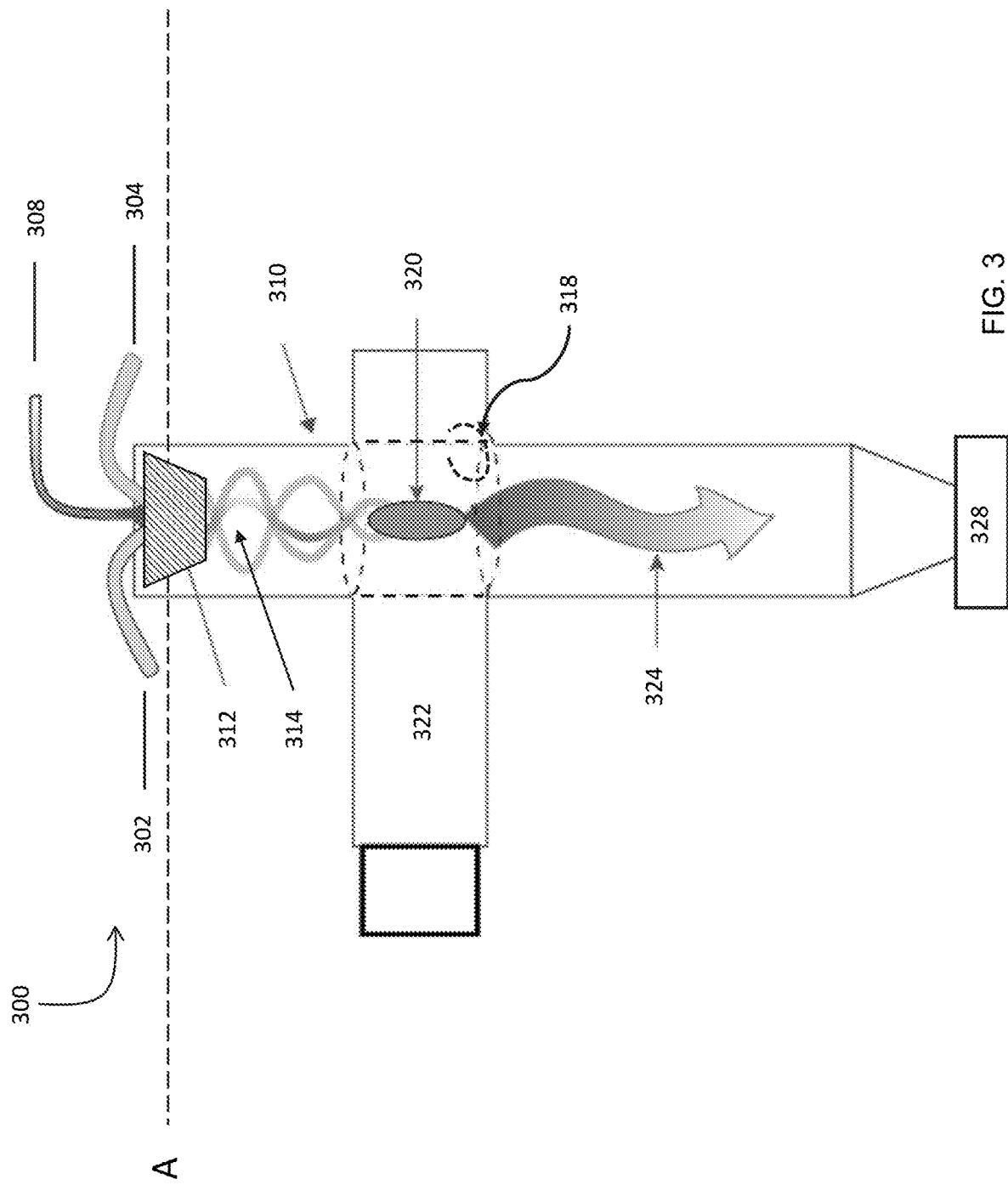
FIG. 3 depicts schematically a gas delivery subsystem.

A schematic diagram of an embodiment of a gas delivery subsystem 300 in accordance with these systems and methods is shown in FIG. 3. As shown in this Figure, a hydrocarbon-bearing inflow gas stream 302 is combined with a hydrogen-bearing inflow gas stream 304 and an optional auxiliary gas stream 308 to enter the plasma reaction chamber 310. In the depicted embodiment, the three gas streams enter through a gas injector 312 (described below in more detail) which disperses the various flows in directions and with velocities such that a vortex intermingling 314 of the three separate flows is produced within the plasma reaction chamber 310. The intermingled gases in the vortex intermingling 314 enter a reaction zone 318 of the plasma reaction chamber 310, where they are energized by the microwave energy produced in the microwave subsystem 322 to form the plasma 320 within the reaction zone 318 of the plasma reaction chamber 310. In the depicted embodiment, the inflow gases 302, 304 and 308 each enter the gas injector 312 as separate streams through separate inlets, and each enters the plasma reaction chamber 310 through its own outlet from the gas injector. The flow direction, flow velocity and flow rate from each outlet is oriented so that it produces the vortex intermingling 314 of the gases within the plasma reaction chamber 310.

Inflow gases can be introduced into the plasma reaction chamber in constant or variable flow patterns, and in continuous flow patterns or discontinuous flow patterns, and in any combination of these patterns. In embodiments, a variable flow pattern can be regular or irregular in its variability, and it can include intermittent pulses or surges of flow superimposed on an underlying wave form describing the flow pattern. A sinusoidal flow pattern would be an example of a variable flow pattern, as would a stepwise or "boxcar" flow pattern using square waves to delineate different amounts of flow. In embodiments, these variable flow patterns can include periods where there is no flow, so that the variable flow pattern would be discontinuous. In embodiments, gases can be introduced through all of the inlets simultaneously, or gases can be introduced through different inlets at different times. Gases can be introduced at different flow rates and at different flow patterns at each inlet. For example, a feed gas can be introduced continuously with a constant flow pattern, while one or more auxiliary gas streams can be introduced sporadically, i.e., discontinuously. Or, for example, the feed gas can be introduced discontinuously (i.e., with interruptions in its inflow), with one or more auxiliary gases introduced variably and/or discontinuously so that the auxiliary gases are flowing while the feed gas is not. Or, as another example, a feed gas can be introduced continuously with a continuous flow pattern, while one or more auxiliary gas streams can be introduced continuously, but with a different flow pattern than the feed gas. Other combinations of continuous/discontinuous patterning and flow pattern variability can be arranged to accomplish specific gas processing goals, for example, to decrease soot formation in the plasma reaction chamber, or to increase acetylene selectivity, or to allow for intermittent cleaning of the reaction tubing interior.

As previously described, gases that are energized into the plasma state undergo a spectrum of reactions, so that a hydrocarbon feed gas is transformed into other hydrocarbons plus hydrogen. FIG. 3 shows an outflow stream 324 emerging from the plasma 320 that contains the desired hydrocarbon product or products, certain extraneous hydrocarbon products, and hydrogen gas. The components of the outflow stream 324 are separated from each other by means of the effluent separation/disposal system 328, described previously.

iii. Gas Injector

The gas injector introduces the various inflow gas streams into the plasma reaction chamber through a plurality of inlets. In embodiments, the gas injector containing the flow channels for the various inflow gas streams can be printed out of a high temperature resin. It can be deployed within or is disposed in fluid communication with the reactor at a variable distance from the plasma reaction chamber within the reactor, where the term "plasma reaction chamber" refers to the region within the reactor where the microwave energy encounters the feed gas streams. In an embodiment, the gas injector can be positioned at the proximal end of the reactor, permitting antegrade gas flow from proximal to distal along the long axis of the reactor. In other embodiments, the gas injector can be positioned at the distal end of the reactor, or can be positioned at any other location along the long axis of the reactor. In embodiments, the gas injector is positioned centrally within the reactor tube, with gas flow directed peripherally. In other embodiments, the gas injector is positioned peripherally within the reactor tube, with gas flow directed centrally. Gas flow exiting the nozzles can be aimed at any angle along the long axis of the tube, so that gas can flow proximally or distally in an axial direction. The nozzles can be arranged to yield symmetric or asymmetric vortex flow.

In embodiments, the inflow gas flows can be aimed by the gas injector so as to create a spiral or vortical gas flow, which assists with mixing the various gas streams. The gas injector is configured to provide a separate nozzle or port for each inflow gas stream as it enters the reactor. The vortical flow can be produced from a gas injector device disposed centrally in the reactor with two or more nozzles or ports, where each inflow gas is separately delivered through its own subset of the one or more nozzles or ports. In an embodiment, these nozzles or ports, located centrally within the reactor, can be aimed peripherally, and can be angled to create the desired gas flow pattern. In other embodiments, vortical flow can be produced by gases flowing into the reactor through a gas injector having two or more nozzles or ports arrayed along the periphery of the reactor, where each inflow gas is separately delivered through its own discrete subset of the two or more nozzles or ports. In embodiments, the vortical flow serves to confine the plasma toward the interior region of the reactor. Additional vortex flow configurations, such as reverse vortex flow, can also be employed, as would be understood by those skilled in the art.

Figure 4A:
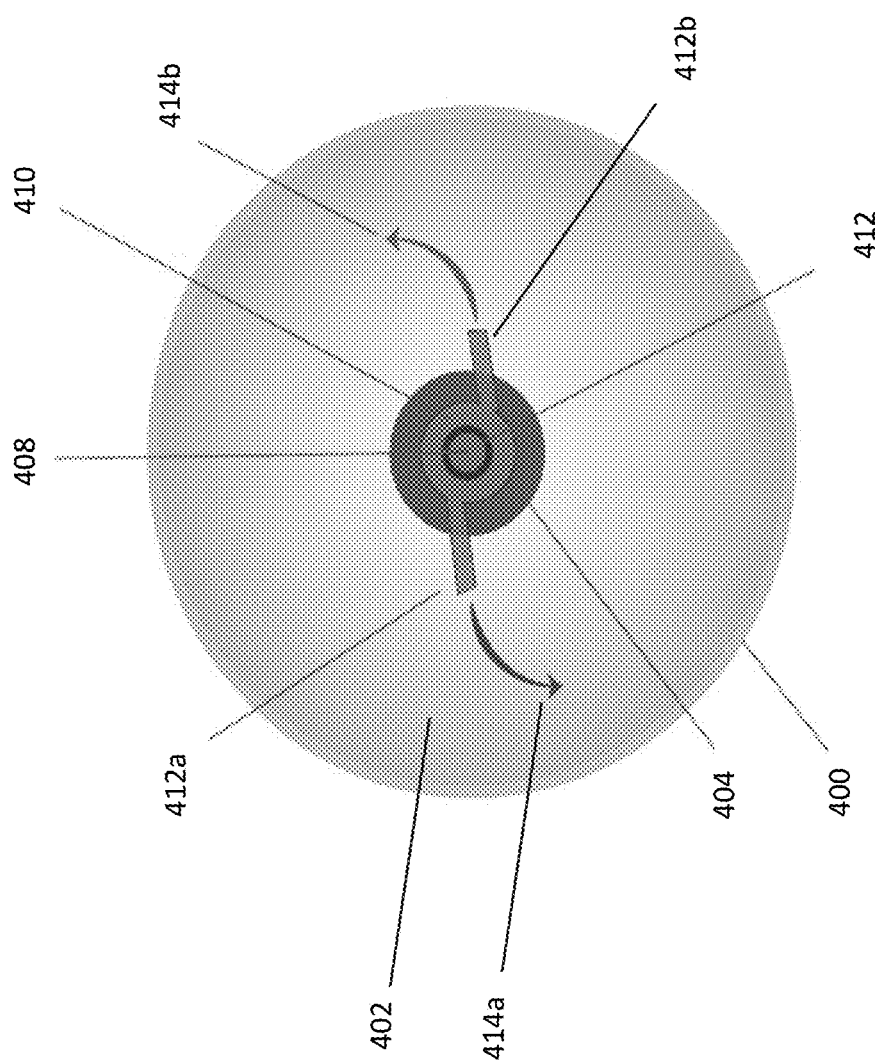
FIGS. 4A and 4B illustrate embodiments of gas injectors.
Figure 4B:
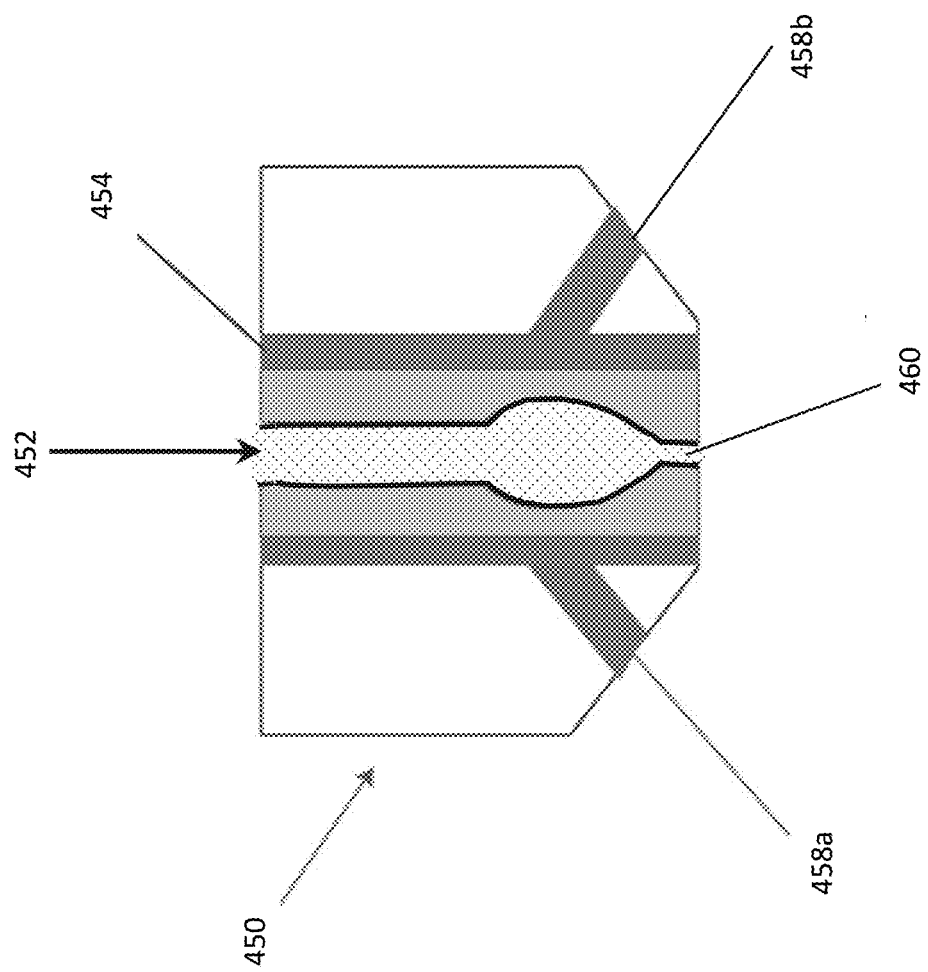

FIGS. 4A and 4B depict an embodiment of a gas injector that is compatible with these systems and methods. FIG. 4A shows a transverse cross-section of the proximal part of the reaction chamber 402 of a plasma reactor 400, within which the gas injector 404 is centrally located; the approximate location of the depicted cross-section in FIG. 4A is shown as Line A in FIG. 3. The gas injector 404 shown in this FIG. 4A encases two coaxial but separate gas flows, a central gas flow 408 and a secondary gas flow 410. The central gas flow 408 contains one gas, for example the main feed gas that can contain methane, the primary reactant. The secondary gas flow 410 contains a separate and distinct gas, for example an additional gas such as hydrogen or an auxiliary gas; this gas can also be a recycled gas such as hydrogen. Alternatively, the central gas flow 408 can contain the additional gas, while the secondary gas flow can contain the main feed gas. In other embodiments (not illustrated), the recycled gas flow can be maintained in a separate coaxial chamber distinct from a flow channel for an auxiliary gas, with each flow channel having its own set of one or more gas nozzles entering the plasma reaction chamber 402. For the injector design depicted in FIG. 4A, the central gas flow 408 exits the gas injector 404 centrally through a central gas nozzle 412 aimed distally and seen here only in cross-section, while the secondary gas flow 410 exits the gas injector 404 through gas nozzles 412a and 412b, which are aimed peripherally. As shown in this Figure, the secondary gas nozzles 412a and 412b are directed at an angle that allows the secondary gas flows 414a and 414b to enter the plasma reaction chamber 402 to form a gas vortex within the reactor 400.

FIG. 4B shows a longitudinal section of an embodiment of a gas injector 450, incorporating the principles illustrated in FIG. 4A. The gas injector 450 depicted in FIG. 4B shows the coaxial arrangement of the central gas flow 452 surrounded by the secondary gas flow 454. The gas injector 450 is positioned centrally within the reactor (not shown in the Figure), and the gas flows from the central gas flow 452 and the secondary gas flow 454 exit the gas injector 450 to flow into the reactor. The secondary gas nozzles 458a and 458b can be arranged at angles (as seen in FIG. 4A), so that the secondary gas exiting these nozzles is aimed to create a vortex flow. As well, the gas exiting the primary gas nozzle 460 can be directed to create or to contribute to a vortex flow. In embodiments, the vortex flow created in the reactor 400 by the gas injector 450 permits gas mixing, which in turn can optimize the exposure of the gas streams to the plasma.

b. Microwave Subsystem

In embodiments, the microwave subsystem comprises the various components used to generate, guide, and apply microwave power to form the non-thermal plasma that transforms the feed gas into its products.

Figure 5:
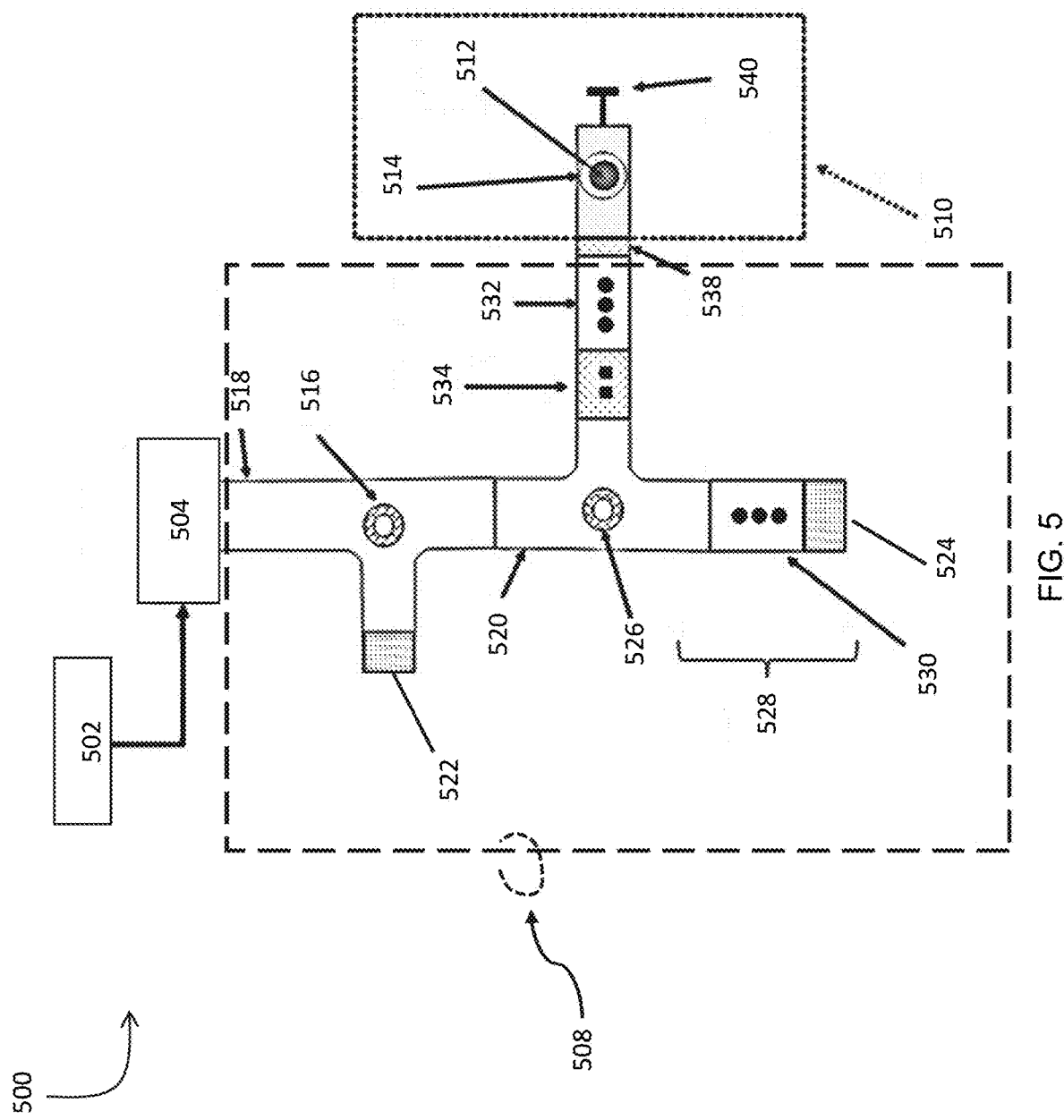
FIGS. 5, 6, and 7 illustrate embodiments of microwave subsystems.
Figure 6:
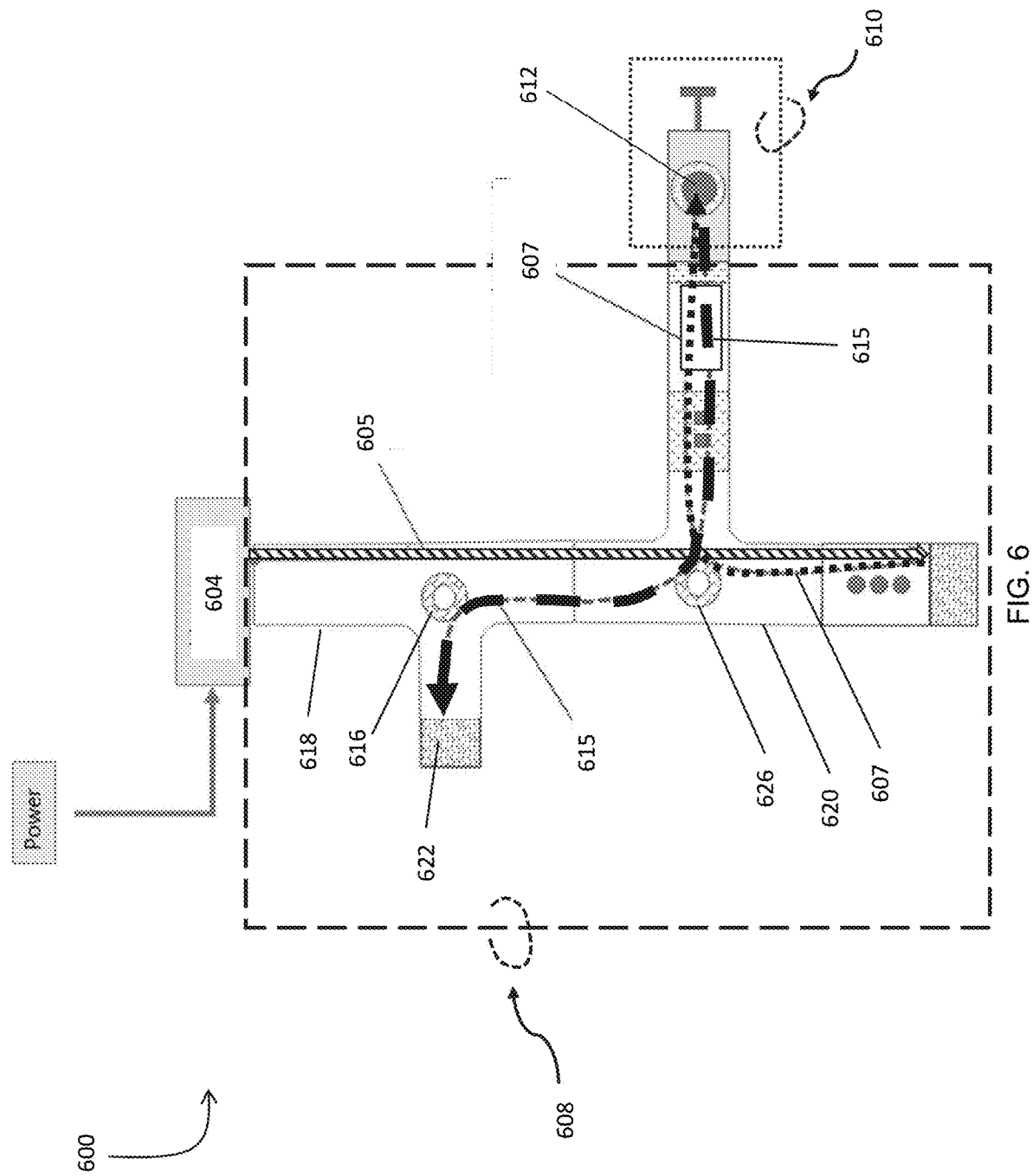

A schematic diagram for an embodiment of a microwave subsystem is shown in FIGS. 5 and 6, described in more detail below. FIG. 5 provides an overview of the subsystem's components. As shown in FIG. 5, an embodiment of the microwave subsystem 500 includes a power supply 502, a magnetron 504, a waveguide assembly 508, and an applicator 510, with the microwave energy produced by the magnetron 504 encountering the inflow gas in a plasma reaction chamber 512 within an elongate reactor tube 514 (seen here in cross-section) to create the plasma. The reactor tube 514 can be made of quartz, as is described below in more detail. In an embodiment, the power supply 502 requires 480 V, 150 A of AC electrical power to generate 20 kV, 5.8 A of low ripple DC power with an efficiency of 96% to energize the magnetron. In an embodiment, the magnetron 504, also rated at 100 kW, produces microwave power at 83-89% efficiency. In embodiments, the microwaves produced are in the L-band, having a frequency of 915 MHz.

As shown in this Figure, the microwaves enter a waveguide assembly 508 that directs them to the applicator 510, which in turn directs the microwaves to the plasma reaction chamber 512 in the reactor tube 514. In the depicted embodiment, the waveguide assembly 508 comprises two circulators 518 and 520, which direct the microwaves towards the applicator 510 and which prevent reflected microwave power from coupling back into the magnetron 504 and damaging it. Each circulator 518 and 520 contains a ferrite array 516 and 526 respectively that deflects reflected microwaves in order to direct them towards the applicator 510 and plasma reaction chamber 512, as described below in more detail. Each circulator 518 and 520 has its respective water load 522 and 524 at its end to collect the reflected microwaves. As depicted, the second circulator 520 includes a power tuner 528 that steps down power using a three-stub tuner 530 in the arm that is distal to its junction with the applicator. In the arm of the second circulator 520 that interfaces with the applicator 510, a three-stub tuner 532 is arranged distal to the dual-directional coupler 534; this arrangement is intended to minimize microwave reflection and optimize the microwave energy directed into the applicator 510. A quartz window 538 is inserted between the second circulator 520 and the applicator 510 to prevent arcing. When the plasma is off and the microwaves are on, a standing wave is set up in the applicator 510 between the three-stub tuner 532 and a sliding shorting plate 540 on the end of the applicator 510 such that the electric field is sufficient to initiate breakdown of the feed gases in the reactor tube 514 that contains the plasma reaction chamber 512. The reactor tube 514 runs through the broad wall of the applicator 510 but is not in direct contact with the microwave waveguide 508. Once the initiation of the plasma state is achieved, the three-stub tuner 532 can then be adjusted to match the impedance of the incoming microwave signal to the plasma-loaded applicator 510. Microwave energy entering the applicator 510 is tuned to peak at the center of the plasma reaction chamber 512, using the shorting plate 540 as needed to change the dimensions of the cavity within which the plasma is formed.

To optimize the power for producing the plasma, it is desirable to match the impedance of the waveguide 508 to the impedance of the applicator 510 in the presence and the absence of the plasma. Plasma impedance is dynamic however, and can change based on the operating pressures, gas flows, and gas compositions in the plasma reaction chamber 512. In embodiments, the microwave subsystem can be equipped with a standard three-stub autotuner 532, which has three metal stubs inserted into the waveguide. The depth to which each of these stubs is inserted into the waveguide alters the phase of the microwaves entering the reactor 510 and allows for power matching into the plasma. Microwave power and phase measurement in the autotuner 532 allow the autotuner 532 to modify stub depth algorithmically, so that reflected power (i.e., the power not absorbed by the plasma), is minimized. In embodiments, a dual directional coupler 534 with attached power diodes (not labeled) can be included, to measure forward and reflected power in the subsystem. The coupler 534 can be fitted with two small holes that couple microwaves with a known attenuation to the diodes, which convert the microwave into a voltage. In embodiments, reflected power is less than 1% of total microwave power sent into the system. In embodiments, the microwave applicator 510 is a single-mode resonant cavity that couples the microwaves to the flowing gas feed in the plasma reaction chamber 512. A sliding electrical short 540 can be built into the applicator 510 to change total cavity length. In embodiments, the plasma for the 100-kW demo unit can generate upwards of 10 kW of heat, which can be removed via water and gas cooling subsystems.

The plasma is created in the plasma reaction chamber 512 within the elongate reactor tube 514. In embodiments, the reactor tube 514 can comprise a long aspect ratio fused quartz tube, with an outer diameter between about 30 and about 120 mm, a length of approximately 6 ft, and a thickness varying from about 2.5 to about 6.0 mm. In an embodiment, the reactor tube can have an outer diameter of 50 mm, or an outer diameter of 38 mm. In embodiments, tube sizes can have an outer diameter (OD) and corresponding inner diameter (ID) of 120/114 mm OD/ID, or 120/108 mm OD/ID, or 80/75 mm OD/ID, or 50/46 mm OD/ID, or 38/35 mm OD/ID. In embodiments, the reactor tube 514 has a consistent diameter throughout its length. In other embodiments, the reactor tube 514 can have a varying diameter, with certain portions of the tube 514 having a smaller diameter, and other areas having a larger diameter. In embodiments, a tube can have an outer diameter of about 50 mm at the top and about 65 mm at the bottom. In embodiments, the tube can have a narrower diameter at a preselected portion of the tube, for example, approximately in the middle of the tube. Quartz is advantageous as a reactor tube 514 material because it has high temperature handling, thermal shock resistance, and low microwave absorption.

FIG. 6 shows, in more detail, a microwave subsystem 600, such as was depicted in FIG. 5, and the paths of microwave energy 605, 607, and 615 flowing therein; in FIG. 6, certain features of the microwave subsystem 600 are shown schematically but, for clarity, were not labeled as they were in FIG. 5. As shown in the embodiment depicted in FIG. 6, microwave energy, generated by the magnetron 604, is directed forward along a forward energy path 605 from the magnetron 604 to the distal end of the waveguide assembly 608, from which it is reflected along an antegrade (forward) reflected path 607. The direction of the antegrade (forward) reflected path 607 is shaped by its encounter with the ferrite array 626 in the second circulator 620, which deflects the reflected microwaves 607 towards the applicator 610 and the plasma reaction chamber 612. Microwaves may also be reflected retrograde from the applicator 610 along a retrograde (reverse) reflected path 615, which passes backwards through the second circulator 620 into the first circulator 618, where the microwaves in this path 615 are collected by the water load 622 within the first circulator 618. The retrograde (reverse) reflected path 615 is deflected by the ferrite array 626 in the second circulator 620, and then by the ferrite array 616 in the first circulator 618 to establish its final direction. In an embodiment, forward power in the system is approximately 25 kW, with reflected power 1% of this or less, with the goal of 0% reflected microwave energy. In embodiments, the forward power in the system is approximately 30 kW; in other embodiments, the forward power in the system is approximately 100 kW. In yet other embodiments, forward power levels of about 8 kW, about 10 kW, or about 19-20 kW can be employed. In embodiments, the system can advantageously encompass a forward power at levels less than about 100 kW.

Figure 7:
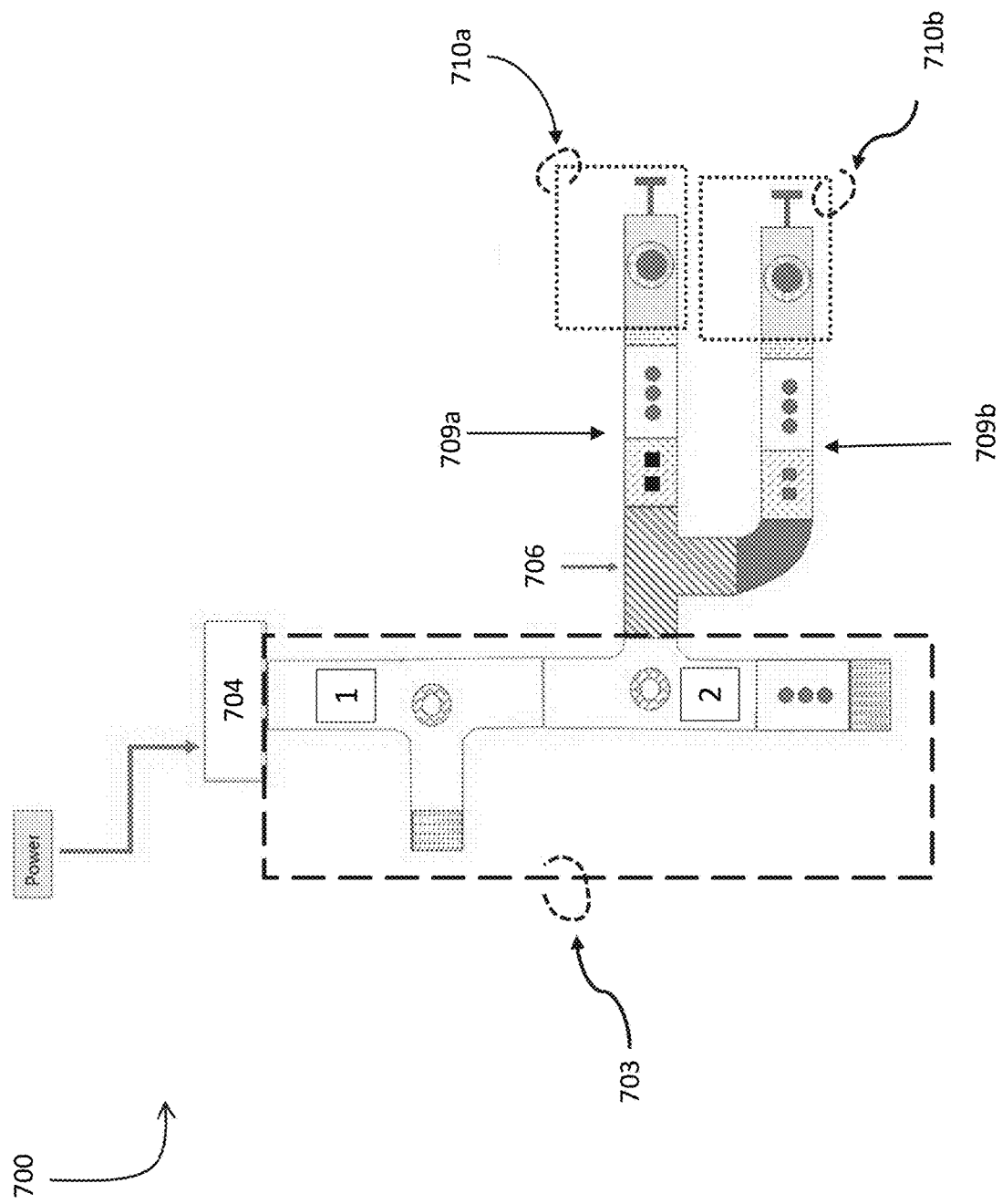

In an embodiment, the microwave subsystem includes a single arm pathway towards the plasma reaction chamber, as depicted in FIG. 5 and FIG. 6. In other embodiments, a double-arm applicator pathway can be employed, as shown below in FIG. 7. As shown schematically in FIG. 7, a double-armed microwave subsystem 700 comprises a magnetron 704 producing microwave energy that enters the circulator assembly 703, which comprises two circulators, labeled "1" and "2." Microwave energy passes through the circulators substantially as depicted in FIG. 6, to enter a power splitter 706 that directs the microwaves into two waveguide arms 709a and 709b, within which arms the microwaves are aimed towards their respective applicators 710a and 710b. In embodiments, the double-arm waveguide 709a and 709b plus applicators 710a and 710b can split the incident power in a 50:50 ratio, but in other embodiments, a selected ratio of power splitting can be engineered.

Certain maintenance measures within the microwave subsystem can extend the lifespan of the components and optimize the product output. In embodiments, for example, the reactor can be cleaned periodically. It is understood that carbon soot build-up can occur in the reactor tube when non-thermal plasma technology is used to convert methane to acetylene, and the presence of soot can lead to localized areas of overheating on the quartz surface with subsequent damage to the reactor tube. In addition, soot that accumulates distal to the microwave coupling can become conductive, leading to formation of undesirable arcs. Therefore, in embodiments, regular cleaning of the reactor is undertaken in order to minimize these problems. Cleaning can be undertaken on a periodic basis, or based on the discontinuous demands for commercial operation, or in response to observable characteristics of the plasma or effluent. For cleaning purposes, several steps are typically employed: 1) de-energizing the plasma process with in the plasma reaction chamber, either by switching off the microwave power creating the plasma, or by shifting the gas inflow from the process gas to an inert cleaning gas or gas mixture (e.g., pure $N_2$ or a combination of nitrogen with air or with other cleaning gases), or both; 2) discontinuing the feed gas inflow and introducing an inert gas mixture (e.g., nitrogen) that purges the inflow lines of the flammable feed gas; 3) filling the reactor with the cleaning gas (e.g., nitrogen mixed with air); 4) re-energizing the plasma reaction chamber with microwave energy to create a plasma state from the cleaning gas, including monitoring and adjusting the microwave energy and the pressure to permit effective cleaning; 5) reversing the process once the reactor tube is clean, with evacuation of the cleaning gas or displacement of the cleaning gas by the feed gas, leading to filling the reactor tube with the feed gas, and subsequent energizing of the feed gas to form a plasma.

In embodiments, soot deposition (and therefore, the need for cleaning) can be minimized by increasing the hydrogen component of the inflow gases; this approach, however, has the drawback of decreased efficiency in hydrocarbon (e.g., methane) conversion. In other embodiments, soot deposition can be managed directly by periodic manual cleaning; this approach has the drawback of requiring physical interventions to access the internal surfaces of the reactor tubing where the soot accumulates. In yet other embodiments, soot deposition can be managed by periodically changing the gas inflow into the plasma reaction chamber from the hydrocarbon:hydrogen feedstock used to produce acetylene to a hydrogen:nitrogen mix which, at low power, forms a plasma that removes soot that has been deposited on the inner surface of the reactor tube. In an embodiment, a pure CO2 plasma can be used as a cleaning plasma. In an embodiment, a hydrogen:nitrogen gas mixture can be used, with a H:N ratio of 5-15:1 can be used, at a power of about 8 kW. In an embodiment, this gas-based cleaning protocol can be carried out on a periodic basis (for example, with a cleaning run of 1-2 minutes every hour or two), aiming for a 1-2% downtime for cleaning out of the continuous run scheme. In other embodiments, a nitrogen:air mixture at a 50:4 ratio can be used, resulting in a cleaning time of about three minutes every 2-3 hours.

An embodiment of this system contains parallel microwave reactor setups multiplexed together, with a first reactor and a second reactor joined after the reactor tube and heat exchanger and isolation valves for each reactor but sharing vacuum pumps. A first reactor's magnetron can be shut off and, and the reactor isolated by the isolation valve, then opened to an alternate vacuum system, while the second reactor is operating to energize the feedstock gas in its plasma reaction chamber. A cleaning plasma can then be utilized for the first reactor. Once the cleaning is done, the first reactor system will be evacuated of the cleaning gas mixture and purged with nitrogen, then purged again by the respective mixture of new feed gas and recycled gas used for the process, then reopened to the main vacuum system and reignited. The second reactor can be cleaned in turn, using the same sequence. In some embodiments, the total number of parallel reactors can be increased to include three or more reactors, with their cleaning cycles sequenced such that the total throughput of the multiplexed system is constant while any one reactor is undergoing cleaning. This cleaning step can therefore be cycled through the multiplexed reactor system individually or in small groups indefinitely, with cycles timed such that there is no loss in product throughput over continuous use.

c. Vacuum Subsystem

In embodiments, a vacuum system is arranged around all components between the gas injector providing gas inflow to the reactor and the product outflow stream distal to the reactor. Maintaining a low pressure in the system contributes to its efficiency (where efficiency is measured by eV of energy per mol of methane converted to acetylene). In embodiments, a vacuum is maintained in the reactor, or a low pressure environment is produced, on the order of about 30 to about 120 Torr, or about 60 to about 100 Torr, or about 70 to about 80 Torr. In an embodiment, an operating pressure of about 70 Torr is maintained for all hydrocarbon feed gases except ethane, which is processed at an operating pressure of about 120 Torr.

Figure 8:
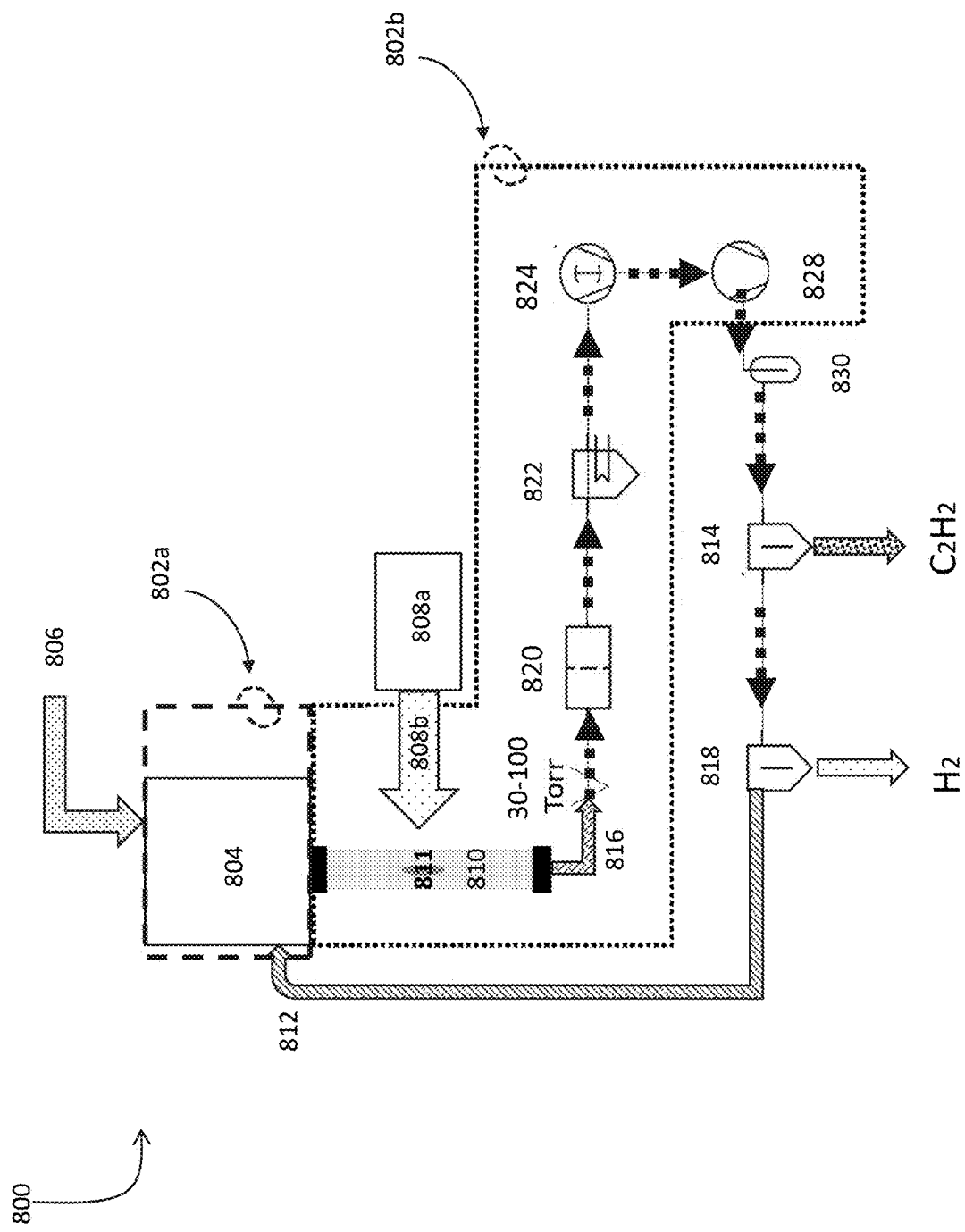
FIG. 8 is a schematic showing a vacuum subsystem integrated with other subsystems of a plasma-based hydrocarbon processing system.

A simplified schematic of a plasma-based hydrocarbon processing system 800 highlighting the vacuum subsystem 802a and 802b is shown in the FIG. 8, with arrows indicating the direction of gaseous flow throughout the system 800. The vacuum subsystem 802a and 802b envelopes certain components of the processing system 800 to maintain a pressure in those components in the range of about 30 to about 120 Torr. As depicted in FIG. 8, the vacuum subsystem designated by the dashed line 802a creates a first reduced-pressure environment around the reactor 810 and its outflow stream 816, and around various components downstream from the reactor 810, all as described in more detail below; the vacuum subsystem designated by the dashed line 802b creates a second reduced pressure environment around the gas delivery subsystem 804. For purposes of clarity, a portion of the vacuum subsystem is identified by dashed line 802a and a portion of the vacuum subsystem is identified by dashed line 802b; these two dashed lines can represent separate subsystems, or they can be merged together to represent a single vacuum subsystem. Subsystems and components shown in this Figure for clarity include: (i) the gas delivery subsystem 804 that passes the inflow gases, including hydrocarbon feed gas 806 and hydrogen-containing recycled gas 812, through their respective feed gas inlets (not shown) into the reactor 810; (ii) a microwave delivery system 808a that forms the microwaves 808b that act upon the inflow gases (i.e., the hydrocarbon feed gas 806 and the hydrogen-bearing recycled gas 812) in the reactor 810 to effect chemical transformations in the two inflow gases 806 and 812 in the plasma reaction chamber 811 region of the reactor 810, with the products of these chemical transformations exiting the reactor 810 as the outflow stream 816; (iii) an effluent separation and disposal system comprising an acetylene separator 814 and a hydrogen separator 818 that separates the outflow stream 816 into its gaseous components, with the remainder of the outflow stream 816 distal to the acetylene separator 814 and the hydrogen separator 818 becomes the recycled gas stream 812. As mentioned previously and as shown in this Figure, certain components situated downstream from the reactor 810 are also contained within the vacuum subsystem as designated by dashed line 802a, such as a filter 820 for the outflow stream 816, a heat exchanger/separator 822, and a series of pumps 824 and 828. In this Figure, a cold trap 830 for removing higher order hydrocarbons is situated outside the vacuum subsystem as designated by dashed line 802a, as are the acetylene separator 814 and the hydrogen separator 818.

The filter 820 shown in the Figure is intended to remove carbon solids from the outflow stream 816. In embodiments, the plasma process makes a small amount of carbon solids as a by-product; for example, carbon solids can be produced in the range of 0.1-0.5%. Therefore, it is desirable to filter the outflow stream 816 to remove these carbon solids in order to prevent these particles from fouling the downstream components of the system. Since the filter 820 is the first surface that the outflow stream 816 encounters after leaving the reactor 810, the gas in this stream is very hot (on the order of 400-1000° C.). Therefore, the material for the filter 820 is selected so that it can withstand such temperatures, with or without additional cooling. In embodiments, the filter 820 can be made of ceramic materials or of stainless steel, with cooling added as needed.

d. Cooling Subsystem

In embodiments, a cooling subsystem can be implemented to control the operating temperatures for the various components of the gas processing system described herein. In embodiments, the plasma formed in the reactor reaches a temperature between 2000-3000 K (1700-2700° C.), exiting the reactor at a temperature of about 400 to about 1100° C. To protect the downstream components of the system from heat damage, cooling is provided. In addition, it is desirable to cool the reactor itself, for example, to keep the outer temperature of the reactor tube below 500° C. Moreover, the reactor tube is more likely to retain heat during gas-based cleaning (as described above) vs during acetylene production, so that more cooling power can be required intermittently to protect the reactor tube from heat stress. In embodiments, the cooling for the system includes two types of cooling: water cooling and gas cooling. Water cooling can be used for many of the components of the system, for example the magnetron, the power supply, the vacuum pumps, the applicator, and the like. Gas cooling can be employed for other components as appropriate, for example, the reactor tube, the reactor itself, and the various O-ring seals in the system. In embodiments, nitrogen is used for gas cooling. Nitrogen has the additional benefit of replacing atmospheric gases in enclosed parts of the system, thus enhancing safety. In an embodiment, the reactor tube and the applicator can be enclosed in a sealed, nitrogen-purged (oxygen-free) environment, where the presence of nitrogen provides cooling and also serves as a safety mechanism: by replacing the oxygen in the environment around the reactor system, the nitrogen gas coolant reduces the chance of explosion if a leak is created.

e. Effluent Separation and Disposal Subsystem

In embodiments, the outflow stream emerges from the low-pressure environment created by the vacuum subsystem, and then undergoes further management to separate the desired gaseous products from each other and from the waste products. Methane and other hydrocarbon-containing gases such as ethane, propane, butane and the like produce acetylene and hydrogen when energized in a non-thermal plasma as described herein, along with particulate carbon and higher-order hydrocarbons. To optimize the economics of the process and to provide a customized gas flow for recycling, a set of components is positioned distal to the vacuum subsystem to segregate certain of the gaseous components in the outflow stream from each other.

In embodiments, it is envisioned that a plasma-based hydrocarbon processing system and the methods of its use described herein convert methane in a stoichiometry that is net hydrogen positive, with 1.5 moles of hydrogen being generated for every mole of methane consumed. The outflow stream thus contains a mixture of hydrocarbons, including the desirable product acetylene, along with a predominance of hydrogen. In embodiments, this hydrogen can be separated from the outflow stream, for example, by using a membrane separator to separate the hydrogen from the remainder of the effluent. After separation, hydrogen can be purified and commercialized as a separate gas product; alternatively, or in addition, hydrogen can be recycled into the system, as illustrated in previous Figures. In other embodiments, acetylene can be separated from the outflow stream instead of or in addition to hydrogen separation. For example, acetylene can be absorbed in an absorption column and then desorbed and collected. In an embodiment, the outflow stream from the reactor can first be treated to remove particulate carbon and condensates, and then acetylene can be removed. After the acetylene is removed, the hydrogen can be optionally removed, captured, or recycled.

As the outflow stream leaves the plasma reaction chamber, it contains a combination of gases, volatilized higher-order hydrocarbons, and particulate carbon. As previously described, the particulate carbon can be filtered out immediately downstream from the reactor chamber. In embodiments, the outflow stream can subsequently be passed through a cold trap in order to remove certain higher-order hydrocarbons from the outflow stream as condensates. After passing through the cold trap, the outflow stream can be further separated. For example, other higher-order hydrocarbons can be removed from the outflow stream as described below. These compounds are typically deemed waste products, and they can be discarded or disposed of after their removal. Following or simultaneously with the removal of higher-order hydrocarbons, acetylene and hydrogen are separated from the outflow stream via the effluent separation and disposal subsystem. The separation process proceeds using one or more separation technologies, such as adsorption technologies, absorption technologies, chemical reaction technologies such as oxidization or catalyst-mediated conversion, and the like.

i. Adsorption

In certain embodiments, for example, the outflow stream can be passed through an adsorption column, where the column contains a high surface-area adsorbent material that can selectively remove acetylene or higher-order hydrocarbons from the outflow stream flowing therethrough. In embodiments, adsorbent material can include appropriately sized materials such as activated carbon, zeolites, silica aerogels, molecular sieves, metal-organic frameworks (MOFs), coordination polymers, clays, diatomaceous earth, or pumice. The adsorbent material can be a powder or a film, or it can be formed into spherical pellets, rods, or other shapes which may be useful. These adsorbent materials can be modified by calcination at elevated temperatures, ion-exchange, or doping with molecules that increase adsorption affinity or capacity. Additionally, a combination of two or more adsorbent materials can be used to take advantage of multiple physical properties. The adsorbent materials can be contained within a single adsorbent column or divided into multiple adsorbent columns to trap different impurities from the outflow stream in distinct locations. Advantageously, adsorbent materials can be selected to minimize product loss as the outflow stream passes through the adsorbent column: in some instances, higher-order hydrocarbon impurities have a higher affinity for the adsorbent material than does the desired product; in other instances, the impurities can displace the product molecules off the surface of the adsorbent. In either case, product loss is minimal.

Under certain circumstances, adsorbents can be disposed of after a single use if the capacity of the adsorbent and the concentration of impurities allows for sufficient impurities to be removed before disposal. Under other circumstances, for example, if disposal is unfeasible for economic or logistical reasons, the adsorbent can be regenerated and re-used cyclically. Methods for regenerating the adsorbent include pressure reduction, solvent washing, heating, and displacement by another gas. During regeneration, the impurities can be desorbed off the surface of the adsorbent, or they can be converted in-situ to another chemical that is easier to desorb. If the impurities have been converted to an acceptable derivative molecule, this molecule can be desorbed in-line and released into the process stream. If the impurities are unaltered on the surface of the adsorbent, so that they cannot be released into the downstream flow, they can be diverted to a side stream to be vented, incinerated or collected for waste disposal. In embodiments, an automated system can arrange for alternation between or among multiple adsorber vessels, allowing for regeneration cycles in a continuous operation; such a system has been referred to in the art as a swing adsorber.

Adsorbers can be used for further separation of the outflow stream after the removal of higher-order hydrocarbons. Depending on the preferred mode of adsorption and desorption, a pressure swing adsorber (PSA), a vacuum swing adsorber (VSA), or a temperature swing adsorber (TSA) can be used. For example, in certain embodiments, the outflow stream can be fed into a PSA system in order to separate hydrogen gas from the outflow stream. In the PSA system, the outflow stream is pressurized and fed into an adsorption column in which all non-hydrogen components are adsorbed onto the adsorbent material. With all non-hydrogen materials removed from the stream a purified hydrogen exits the column. In embodiments, the feed for the PSA system can be the outflow stream from the plasma reactor, or it can be the collected gas from the first absorption column described above, or some combination thereof.

Or, for example, the outflow stream can be fed into a TSA system that is adapted for separating higher acetylenes from the outflow stream. As used herein, the term "higher acetylenes" refers at least to alkynes containing 3 and 4 carbon atoms, although it can also be applied to all gaseous alkynes and to gaseous aromatics. Through use of a TSA system, higher acetylenes can be separated significantly, even completely, from an acetylene stream without acetylene loss. In embodiments, the higher acetylene molecules can displace acetylene on the surface of an adsorbent, allowing for extreme selectivity in separating the higher acetylenes from the acetylene stream. In order to accomplish this, the adsorption process advantageously is terminated before the higher acetylenes are themselves displaced by an even heavier molecule like benzene. Therefore, the adsorption cycle in the TSA should be tuned to allow the higher acetylenes to be adsorbed and retained on the adsorber surface, but to prevent the higher acetylenes from being displaced. Thus, before the higher acetylenes are displaced off the adsorbent surface, the reactor is closed off to the process stream. The adsorbent can then be disposed of and replaced, or alternatively, regenerated. In regeneration, the outflow stream is diverted from the adsorber and hot air (>300° C.) is passed over the adsorbent bed. The impurities are released from the adsorbent and either vented or burned. In some iterations, multiple vessels can be used for a continuous operation in which some vessels are adsorbing while others are regenerating.

ii. Absorption

In certain embodiments, the outflow stream can be passed through an absorption column, wherein a solvent at an optimized flow rate running counter-current to the outflow stream preferentially absorbs higher-order hydrocarbons from the flowing outflow stream instead of absorbing the desired gas product like acetylene. The higher-order hydrocarbons can then be separated from the solvent in a second column, and the solvent is returned to the absorption column. Examples of solvents with stronger affinity for higher-order hydrocarbons over the desired gas product include methanol, ammonia, toluene, benzene, kerosene, butyrolactone, acetonitrile, propionitrile, methoxypropionitrile, acetone, furfural, N,N-dimethylformamide, N,N-diethylformamide, N,N-dimethylacetamide, N,N-diethylacetamide, N-formylmorpholine, and N-alkylpyrrolidones, for example N-methylpyrrolidone (NMP).

In other embodiments, the outflow stream can be passed through an absorption column, wherein a solvent having a strong affinity for acetylene and preferably running counter-current to the outflow stream, absorbs acetylene from the flowing outflow stream. The absorbed acetylene can be removed from the solvent by heating the solvent in a second column for restoring the solvent, and the restored solvent then can be returned to the absorption column. Examples of solvents with stronger affinity for acetylene over other outflow gases include methanol, ammonia, toluene, benzene, kerosene, butyrolactone, acetonitrile, propionitrile, methoxypropionitrile, acetone, furfural, N,N-dimethylformamide, N,N-diethylformamide, N,N-dimethylacetamide, N,N-diethylacetamide, N-formylmorpholine, and N-alkylpyrrolidones, e.g., N-methylpyrrolidone (NMP).

iii. Chemical Reactions

In certain embodiments, higher-order hydrocarbons in the outflow stream can be oxidized and thereby removed from the outflow stream. For example, certain higher-order hydrocarbons, particularly diacetylene and substituted acetylenes such as methylacetylene and vinylacetylene, can be difficult to separate from acetylene, and they can be removed by converting them into non-acetylenic compounds. To accomplish this, the outflow stream can be passed through a column or vessel containing an oxidizing agent, such as a concentrated liquid acid capable of acting as an oxidizing agent, such as nitric acid, sulfuric acid, phosphoric acid, and the like. The higher-order hydrocarbons such as diacetylene and the substituted acetylenes can react with the oxidizing agent or concentrated acid to create other hydrocarbon compounds that can be more easily separated from the outflow stream. In certain embodiments, the outflow stream can be contacted with phosphoric acid on a solid support to convert the higher-order hydrocarbons such as diacetylene and the substituted acetylenes into other hydrocarbon products that can be more easily separated from the outflow stream.

In certain embodiments, the outflow stream can be passed through a catalyst bed, using a catalyst that comprises transition metals, transition metal oxides, transition metal salts, or zeolites, in order to convert various higher-order hydrocarbons into other carbon species that are more readily removable from the gaseous product stream. When exposed to a suitable catalyst, these higher-order hydrocarbons can be converted into a more easily removable compound by catalyst-driven mechanisms such as polymerization, oxidation, hydrogenation, and disproportionation. Depending on the mechanistic mode of catalytic conversion and the products obtained, these derivatives of the higher-order hydrocarbons can be removed through further downstream processes such as are described herein.

iv. Other Separation Technologies

In certain embodiments, higher-order hydrocarbons can be removed from the outflow stream by using a condenser, whereby the condenser collects these compounds on a high-surface-area material such as silica gel, activated carbon, activated alumina, zeolites, and the like. For example, certain higher-order hydrocarbons, e.g., methylacetylene and vinylacetylene, can be difficult to separate from acetylene in gaseous form, but their condensation points (5.01° C. and 10.3° C. respectively) contrast to the condensation point of acetylene (−84° C.) making them suitable for removal via condensation from the outflow stream. In this embodiment, a cold bed containing high surface area material at temperatures between −84° C. and 10° C. can effectively condense out higher-order hydrocarbons from the outflow stream.

In certain embodiments, the outflow stream can be passed through a gas separation membrane system, wherein gas molecules are separated via size exclusion. For example, smaller molecules, such as hydrogen, will preferentially flow through the membrane element, forming a permeate stream, while larger molecules, such as methane, acetylene, higher-order hydrocarbons, nitrogen, carbon dioxide, and any other larger molecules, do not flow through the membrane (depending on the porosity of the membrane), forming a retentate stream. In certain embodiments, the permeate steam is a hydrogen-enriched stream and the retentate stream is a hydrogen depleted stream. Gas separation membrane elements can be formed from a variety of substances, for example: hollow fiber polymer membranes where the polymer can be polycarbonate, polyamide, or cellulose acetate; inorganic membranes where the inorganic material can be mesoporous silica, zeolite, a metal-organic-framework, or mixed metal oxides; metal membranes where the metal can be palladium or palladium-silver alloys; and the like. In embodiments, the feed for the membrane separation system can be the outflow stream from the plasma reactor, or it can be the collected gas from the first absorption column described above, or some combination thereof.

Following certain of these outflow separation measures, in embodiments, the outflow stream, containing acetylene, hydrogen, and higher-order hydrocarbons, can be further separated into its components so that the desired gaseous products can be retrieved. In other embodiments, the outflow stream is not subjected to further separation, for example if it is to be used for further chemical processing, or if it is provided to a customer or end-user as a mixed stream.

f. Data Management and Safety Subsystems

Advantageously, the overall gas production system comprises interconnected data management subsystems and safety subsystems, so that the safety measures incorporated in these systems and methods are informed by data collected about the system's performance. In embodiments, data management can include devices, procedures and algorithms for data collection and performance diagnosis, and storage facilities for recording and preserving data. In embodiments, performance diagnosis includes monitoring the state of the system within normal parameters to facilitate overall integration and control and identifying signs of upcoming or active failure states. Optical diagnostics can be directed at surveillance of the plasma region, for example visible light cameras, mid-IR pyrometers, broadband spectrometers, and the like. Apparatus diagnostics can include pressure transducers, thermocouples, flow meters, microwave power sensors, and the like. Other diagnostic equipment can be used as appropriate, for example full-scale spectrometers and oscilloscopes. In embodiments, various diagnostic modalities can be integrated and monitored automatically and/or manually during a run.

In embodiments, the manual and automatic diagnostic procedures can be integrated with safety procedures, which can include a fault-interlock system. In an embodiment, diagnostic input can be actively monitored by hardware and software. If an anomaly is detected, a fault signal can be triggered that activates a predetermined response pattern. For those most serious faults, such as a sudden corroborated pressure spike, an immediate automated "hard" shutdown can be triggered. For faults of moderate severity, where the consequences are less serious, a slower automated shutdown can be triggered, intended to stop operations over the course of several seconds. For those faults where a parameter is outside the expected range, but no major consequences are anticipated, the operator can be alerted, so that appropriate actions are taken to rectify the situation and clear the fault without requiring a system shutdown.

3. Exemplary Systems and Subsystems a. 100 kW-Powered Plasma-Based Hydrocarbon Processing System A plasma-based hydrocarbon processing system using plasma technology to transform hydrocarbon-containing inflow gas into acetylene and hydrogen can obtain a high degree of source hydrocarbon conversion in combination with a high degree of selectivity for the production of acetylene and/or hydrogen. The system described below uses a 100 kW power supply to generate the microwaves that form the plasma and effect the chemical transformations.

The central reaction of this process takes place when methane (derived, for example, from natural gas or biogas) or another $C_2$-$C_4$ source hydrocarbon is fed into a microwave-energized region, where it breaks down into a plasma. Without being bound by theory, it is postulated that the plasma drives the reaction from the source hydrocarbon to acetylene and hydrogen by decomposing the hydrocarbon into excited $CH_x$ radicals that recombine after the plasma energy state to form a spectrum of hydrocarbon products and hydrogen. Using a $C_2$-$C_4$ hydrocarbon as a feed improves the overall process efficiency as compared to methane, while a high degree of selectivity to acetylene can be maintained. However, using methane as contained in natural gas or biogas has the advantage of operational efficiency and cost-effectiveness.

The methane conversion process in the 100 kW-powered processing system (i.e., using methane as may be found in a natural gas or biogas feed or a pure methane feed) uses approx. 9.5 kWhr per kg of acetylene product formed, with an acetylene yield of 90%: for the feed gas employed, about 90% is converted to acetylene. The resulting product mix is influenced by the non-thermal nature of the plasma temperatures. The gas temperature is 3000-4000 K while the vibrational temperature and electronic temperatures are two to three times higher, pushing the reaction equilibrium to form acetylene with a high selectivity, and with abundant hydrogen as a byproduct. Hydrogen produced by the plasma reaction can be recycled back into this system as a secondary feed gas that is used for subsequent reactions, and/or it can be segregated as a separate gas product. The co-presence of hydrogen and hydrocarbon as components of the reaction reduces the reaction's production of solids. To achieve a desirable proportion of hydrogen and methane for the reaction, the system recycles the produced hydrogen to participate in the methane-based reactions, as described in more detail below.

i. Overall System

The 100 kW-powered plasma-based hydrocarbon processing system comprises four subsystems: gas delivery, microwave, vacuum, and cooling. The gas delivery subsystem contains two inflow lines. The first inflow line is a feed line conveying a mixed gas such as natural gas continuously sourced from a local utility company or such as upgraded biogas, comprising a mixture of predominantly methane, with small amounts of ethane, propane, carbon dioxide, and nitrogen (depending on the source of the raw mixed gas). This inflow may be scrubbed using conventional technologies before it enters the plasma reaction chamber, resulting in an almost pure methane stream, with other residual mixed gas components present on the order of about 100 ppm. The total flow from this inflow line is scalable with the overall microwave power of the system, with a flow of approximately about 3 SLM methane/kW microwave power. A second inflow line conveys recycled gas produced by the reactor that contains about 85 to about 90% hydrogen, with small amounts of methane, other reactants, and an amount of unreactive nitrogen of about 5 to about 6%. The total flow from this inflow line is also scaled with the overall microwave power of the system, with a flow of about 5 SLM recycled gas/kW microwave power.

Each inflow stream is sent into the plasma reaction chamber through its own inlet that injects its flow into an entry region of a quartz tube to flow through the tube to the region in which the plasma is created. The inlet for each inflow stream can be angled by a gas injector device to produce the vortex flow that mixes the streams within the quartz tube as they flow towards the reaction region, i.e., the plasma reaction chamber. The flow of gas entering through each inlet is controlled by mass flow controllers, adjusted to create a hydrogen-to-methane molar ratio of 1.5 $H_2$:1 $CH_4$. As the methane is transformed into plasma, a spectrum of reaction products is formed within the plasma reaction chamber within the quartz tube.

When methane is used as a feed gas, about 95% of the methane undergoes chemical change within the plasma. Acetylene accounts for 95% of the hydrocarbons produced from the plasma-energized reactions, giving an overall approximate 90% acetylene yield. Hydrogen is the other dominant reaction product from these reactions, accounting for approximately 80% of the total outflow stream by volume.

Figure 9:
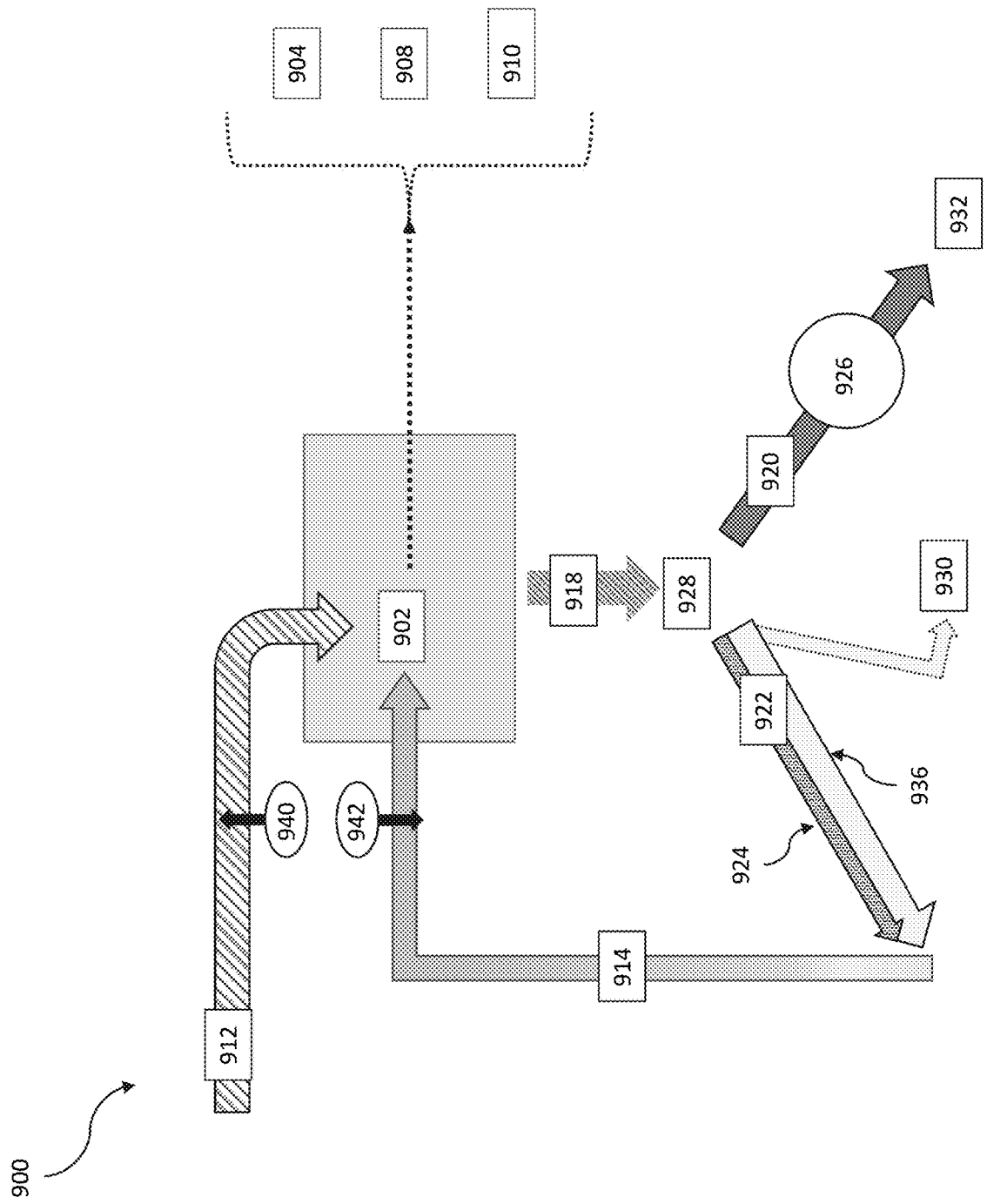
FIG. 9 is a block diagram of a plasma-based hydrocarbon processing system and related subsystems.

An exemplary 100 kW-powered plasma-based hydrocarbon processing system 900 is represented schematically by the block diagram shown in FIG. 9. As shown in this Figure, a central reactor 902, comprising an injection region 904, a reaction region 908, and an outflow region 910, receives two separate gas streams: (1) a feed gas 912 containing a source hydrocarbon (for example the methane in a mixed gas such as natural gas or biogas, or a single $C_1$-$C_4$ hydrocarbon, or a customized blend of $C_1$-$C_4$ hydrocarbons), and (2) a recycled gas flow 914 that includes hydrogen and mixed hydrocarbon-containing gas and optionally unreactive nitrogen.

As schematically represented in the Figure, the inflow gas streams 912 and 914 are processed in the reactor 902 to form an outflow stream 918 that contains acetylene, hydrogen, and a small proportion of mixed hydrocarbons. The outflow stream 918 is then separated into its gaseous components via a gas separation system 928 (e.g., adsorption, absorption, or a combination thereof, to yield an acetylene stream 920 and a hydrogen-dominant gas stream 922 that contains hydrogen 936 and a mixture of hydrocarbons 924. Thus diverted from the main outflow stream 918 by the gas separation system 928, the acetylene stream 920 can be purified via further sequestration of impurities in a purification system 926 to yield a purified acetylene gas product 932. Once the acetylene component 920 has been removed from the outflow stream 918, the remaining gas stream 922 is predominantly hydrogen along with a mixture of hydrocarbon reaction products, i.e., is hydrogen-dominant. This hydrogen-dominant gas stream 922 can be subjected to further separation if desired, so that hydrogen gas is isolated as a distinct gas stream 930. The hydrogen gas product stream 930 can be further purified as necessary and sold as a product, or it can be recycled back into the reactor 902 for further reaction with the feed gas 912. In this system 900, instead of recycling the hydrogen gas product stream 930, the mixed hydrogen-dominant gas stream 922 is recycled to form the recycled gas flow 914, which is reintroduced into the reactor 902 for further reaction with the feed gas 912. Mass flow controllers 940 and 942 coordinate the inflow of the feed gas 912 and recycled gas 914 into the reactor 902 to create the desired ratio of hydrogen to methane (or hydrogen to other source hydrocarbon) in the reactor 902.

ii. Reactor

The reactor identified in FIG. 9 is shown in more detail in FIG. 10. FIG. 10 depicts schematically the reactor 1002, its components, and its integration with the microwave subsystem 1004. As depicted, and as outlined by the grey shadowed box, the microwave subsystem includes a power supply and magnetron complex 1016 for producing the microwaves, and a waveguide assembly 1020 for guiding the microwaves towards a reaction region 1012 within the quartz tube where the microwave plasma 1018 is formed. As shown in FIG. 10, a quartz tube 1008 contains the components of the reactor 1002: the injection region 1010, the reaction region or reaction chamber 1012, and the outflow region 1014. Within the quartz tube 1008, the microwave plasma 1018 is generated by the microwaves (not shown) aimed at the gas flow 1006 within the tube 1008, thereby effecting the transformation of source hydrocarbon into hydrogen and various hydrocarbon-derived products. This quartz tube 1008 is inserted through the broad wall of a microwave waveguide assembly 1020. The size of the quartz tube 1008 depends on the amount of microwave power used in the system. For the depicted system using 100 kW of power to produce microwaves, the quartz tube 1008 has an 80 mm outer diameter, a 75 mm inner diameter, a length of 1700 mm, and is maintained at a pressure of about 70 Torr by downstream vacuum pumps (not shown). The relationship of the quartz tube 1008 and the microwave subsystem 1004 is described below in more detail.

As shown in FIG. 10, the recycled gas stream 1022 mixes with the feed gas stream 1024 within the injection region 1010 of the reactor 1002, each stream entering the injection region 1010 of the reactor 1002 through its own inlet (not shown). The passage of each gas stream through the gas injector device 1032 (also shown schematically in FIG. 11) into the reactor 1002 affects its direction, flow rate, and velocity. As depicted in FIG. 10, an optional gas stream or gas streams 1028 can be directed into the injection region 1010, to be blended with the recycled gas stream 1022 and the feed gas stream 1024 to create a vortical gas flow 1006. After mixing, the gases in the gas flow 1006 flow distally through the quartz tube 1008, to encounter microwave energy produced by the power supply and magnetron complex 1016 and delivered through the waveguide assembly 1020 into the reaction region 1012 of the reactor 1002. The interaction of the microwave energy and the gas within the reaction region 1012 of the reactor 1002 produces the plasma 1018. The outflow gaseous stream 1034 containing the reaction products emerges from the plasma 1018 to enter the outflow region 1038 of the quartz tube 1008, to be passed out of the reactor 1002 for further separation 1040. As shown in this Figure, a microwave subsystem 1004 includes the power supply and magnetron complex 1016 and the waveguide assembly 1020; not shown in this Figure are additional elements of the microwave subsystem that are illustrated and described in the Figures below.

Figure 11A:
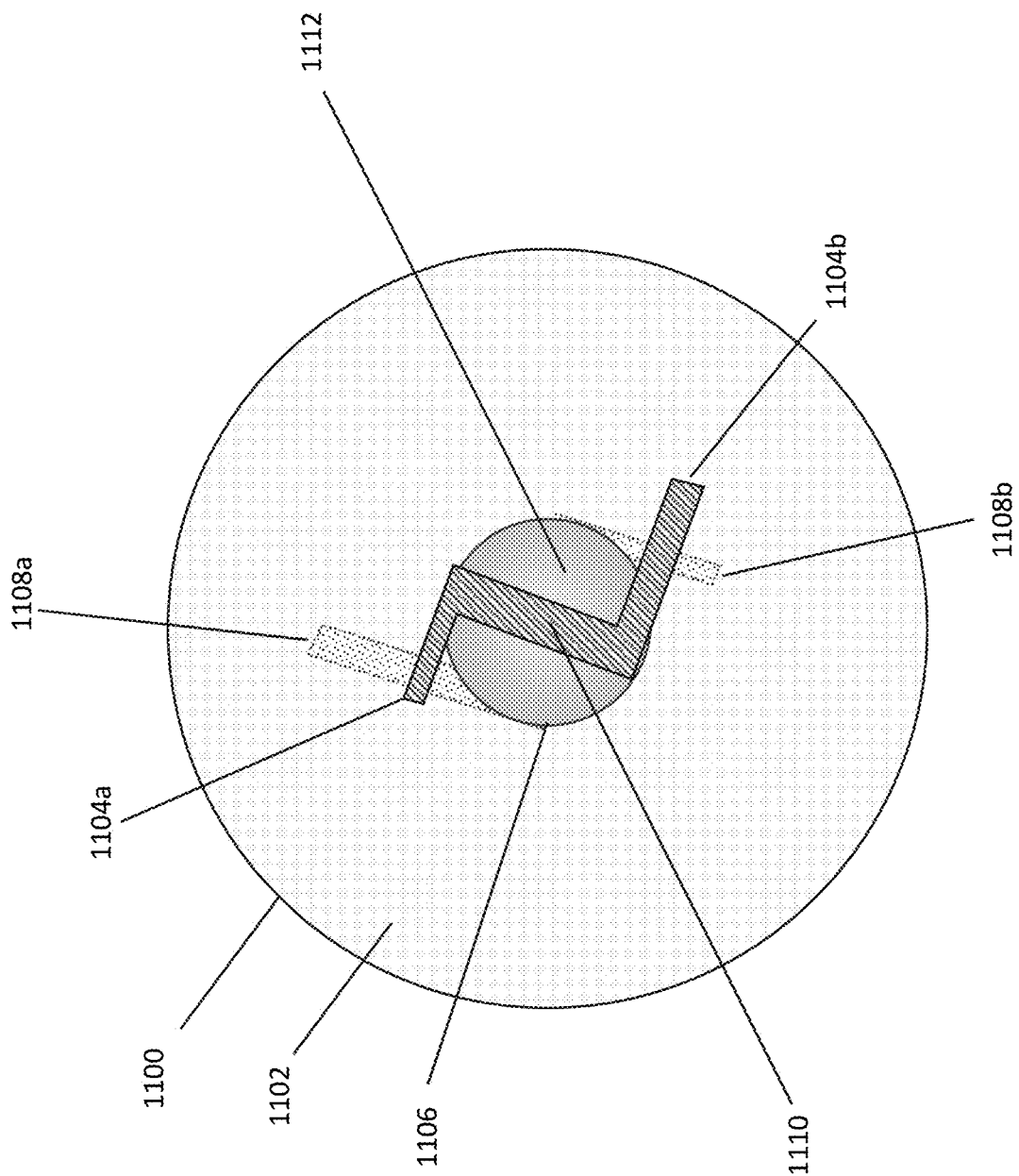
FIG. 11A is a schematic diagram of a gas injector in cross-section.

FIG. 11A is a cross-sectional schematic view (not to scale) of an embodiment of a gas injector suitable for use with the 100 kW-powered plasma-based hydrocarbon processing system, such as the gas injector 1032 depicted in FIG. 10. For exemplary purposes, the cross-sectional view in FIG. 11A corresponds to a cross-section taken at the line A-A' in FIG. 10. FIG. 11A shows a gas injector 1106 situated in a reaction chamber 1102 of a plasma reactor 1100 and providing a plurality of gas flows into the reaction chamber 1102 for those gases to encounter microwave energy as described above. As shown in this Figure, the gas injector 1106 provides flow paths for two distinct gas streams into the reactor 1102, with each gas stream directed through its own nozzle and flow path within the gas injector device 1106 and into the reactor 1102. As illustrated in FIG. 11A, there are four injector ports, two for the recycled gas flow 1104a and 1104b, and two for the feed gas stream 1108a and 1108b. In the Figure, the two recycled gas nozzles 1104a and 1104b are in fluid communication with a first central flow channel 1110 through which the recycled gas stream enters the gas injector 1106 and is directed to the recycled gas nozzles 1104a and 1104b. Similarly, there is a second centrally-disposed channel 1112 in the gas injector 1106 for feed gas, where this channel is discrete from the first central flow channel 1110 for the recycled gas stream. There are two nozzles for feed gas 1108a and 1108b, in fluid communication with the second centrally-disposed channel 1112, with these nozzles 108a and 1108b entering the reactor 1102 at a different level than the nozzles for the recycled gas 1104a and 1104b. The nozzles for both types of gas flow are oriented in directions that are conducive for the formation of a vortex gas flow within the reactor 1102. The channel for recycled gases 1110 and the channel for feed gas 1112 do not intersect with each other, but rather provide separate gas streams into their respective nozzles 1104a/1104b and 1108a/1108b; neither do the nozzles intersect with each other, but rather, provide their gas streams separately into the reactor 1102. The gas flow through each of the nozzles can be coordinated with the other gas flows in the other nozzles in terms of flow rate, path length, and pressure drop.

It would be understood by skilled artisans that the relative position of the feed gas channel 1112 and the recycled gas channel 1110 can be rearranged, for example, as parallel channels, as helices, at different levels within the gas injector 1106, or as other arrangements besides those shown in FIG. 11A, provided that the channels for each gas are kept separate from each other in the gas injector 1106, and further provided that each distinct gas stream enters the reactor 1102 through its own discrete nozzle or nozzles. Moreover, the number, configuration, and direction of the nozzles can be varied, provided that the gas stream for each component gas (i.e., feed gas and recycled gas and any optional additional gas) enters the reactor through its own nozzle, without commingling with the other gas stream.

Figure 11B:
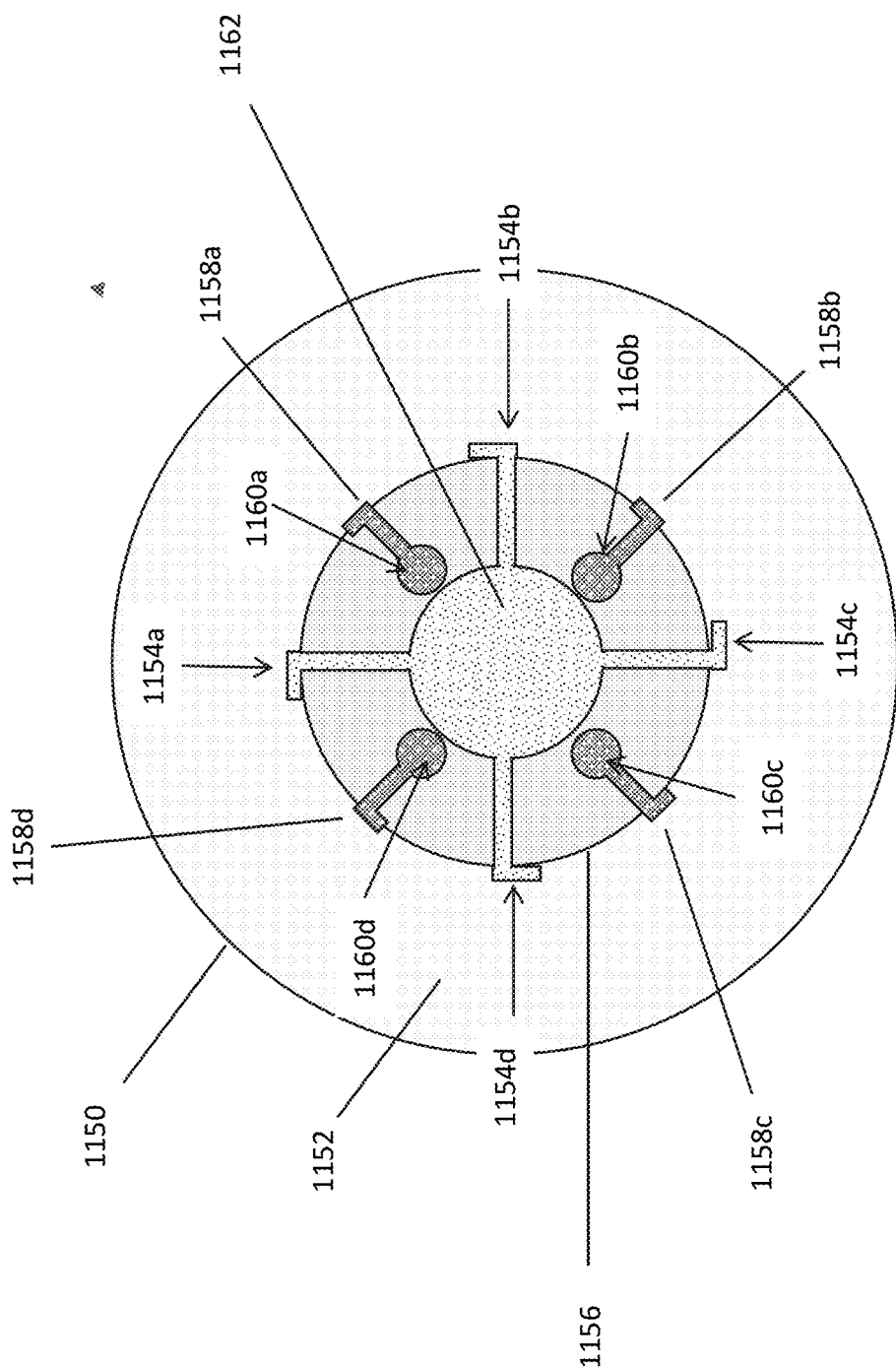
FIG. 11B is a schematic diagram of a gas injector in cross-section.

FIG. 11B is a cross-sectional schematic view (not to scale) of another embodiment of a gas injector suitable for use with the 100 kW-powered plasma-based hydrocarbon processing system, such as the gas injector 1032 depicted in FIG. 10. For exemplary purposes, the cross-sectional view in FIG. 11B corresponds to a cross-section taken at the line A-A' in FIG. 10. FIG. 11B shows a gas injector 1156 situated in a reaction chamber 1152 of a plasma reactor 1150 and providing a plurality of gas flows into the reaction chamber 1152 for those gases to encounter microwave energy as described above. As shown in this Figure, the gas injector 1156 provides flow paths for two distinct gas streams into the reactor 1152, with each gas stream directed through its own set of nozzles within the gas injector device 1156 and into the reactor 1152. As illustrated in FIG. 11B, there are eight injector ports or nozzles, four (1154a, 1154b, 1154c, and 1154d) for a first gas flow, for example the recycled gas flow, and four (1158a. 1158b, 1158c, and 1158d) for a second gas flow, for example a feed gas stream. In the Figure, the four nozzles for the first gas flow (1154a, 1154b, 1154c, and 1154d) are in fluid communication with a central flow channel 1162 through which the first gas stream enters the gas injector 1156 and is directed to the appropriate nozzles 1154a, 1154b, 1154c, and 1154d. The nozzles 1158a. 1158b, 1158c, and 1158d for the second gas flow are each supplied by a separate flow channel 1160a, 1160b, 1160c, and 1160d respectively. Other arrangements of the flow channels to supply the nozzles 1158a. 1158b, 1158c, and 1158d for the second gas flow can be envisioned, provided that the flow channels for the second gas flow do not permit the second gas flow to be commingled with the first gas flow. Instead, each gas flow is conveyed with its own discrete set of nozzles and its own flow channel(s). The nozzles for the first gas flow 1154a, 1154b, 1154c, and 1154d, and the nozzles for the second gas flow 1158a, 1158b, 1158c, and 1158d, are oriented in directions that are conducive for the formation of a vortex gas flow within the reactor 1152. The gas flow through each of the nozzles can be coordinated with the other gas flows in the other nozzles in terms of flow rate, path length, and pressure drop.

iii. Microwave Subsystem

Figure 12:
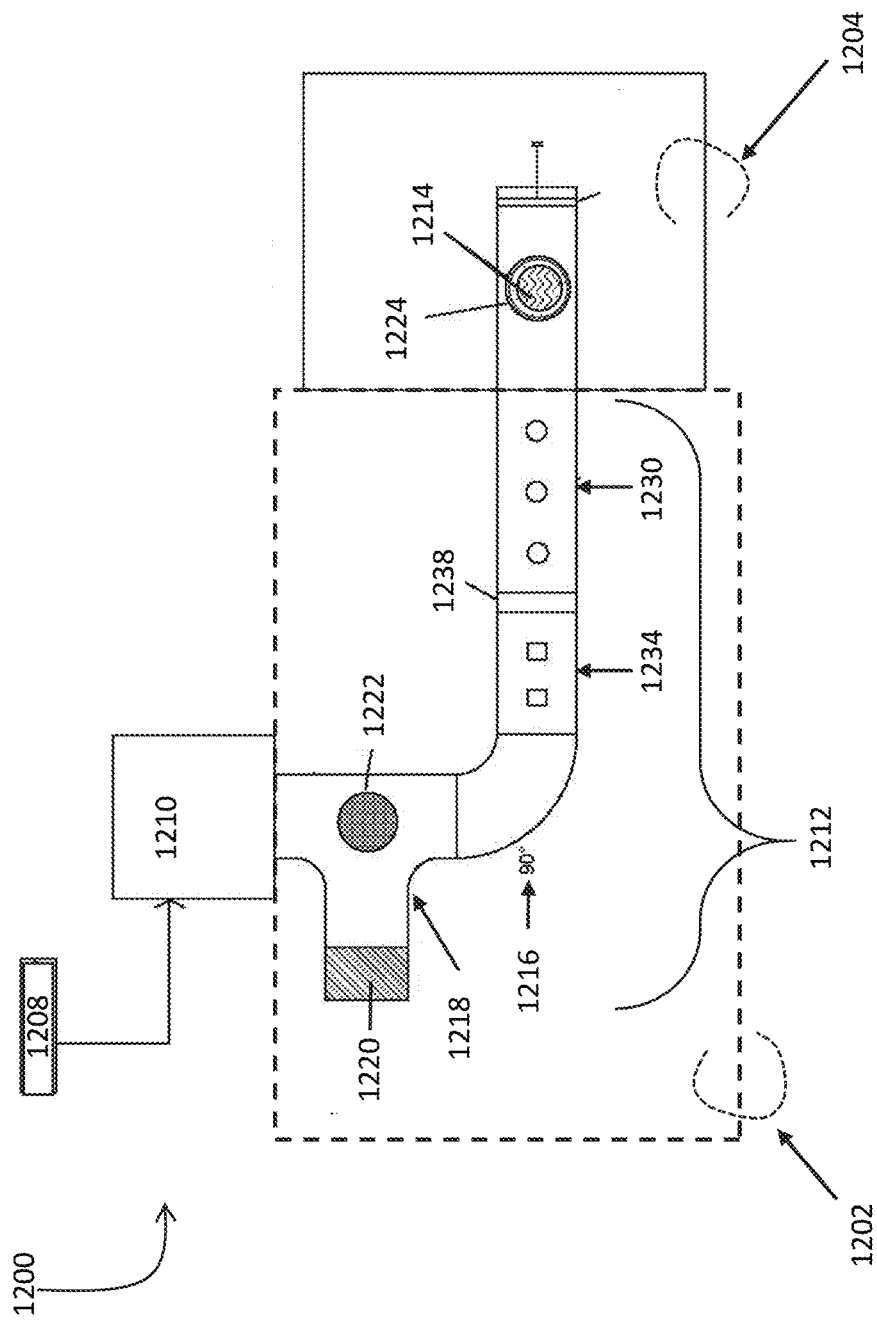
FIG. 12 is a schematic diagram of a microwave subsystem.

The microwave subsystem shown in FIG. 10 is depicted schematically in FIG. 12, and in more detail. Referring to FIG. 10, a reaction region 1012 of the reactor 1002 can be seen intersecting with the waveguide assembly 1020, wherein the microwaves are directed at the gas flow 1006 as it enters the reaction region 1012 to form the plasma 1018. The microwave subsystem 1004 is responsible for generating the microwaves and directing them towards the reactor 1002.

The microwave subsystem is shown in more detail in FIG. 12. As shown in this Figure, the microwave subsystem 1200 comprises a power supply 1208, a magnetron 1210, a waveguide assembly 1202 (which includes a waveguide 1212 and certain other standard microwave components as described below), and an applicator 1204. The power supply 1208 converts 480V, 150 A AC electrical power to 20 kV21 kV, 5.8 A of low-ripple DC power with a conversion of 96% to energize the magnetron 1210. The magnetron 1210, rated at 100 kW, produces continuous microwave power at 83-89% efficiency. The microwaves produced are in the L-band frequency range, approximately 915 MHz. The microwaves are launched into a waveguide assembly 1202, within which a waveguide 1212 directs them through the other components of the system and to the applicator 1204, where they interact with the gas/plasma in the plasma reaction chamber 1214. The waveguide 1212 features a 90-degree bend 1216. One of the components of the waveguide is an isolator 1218 with an attached water load 1220, located distal to the magnetron 1210, to protect the magnetron 1210 from reflected (un-absorbed) microwaves by directing them with a ferritic core 1222 to the water load 1220. The other components of the waveguide assembly 1202 allow the microwaves to be guided towards the plasma reaction chamber 1214 and tuned to optimize the creation of the plasma therein. The applicator 1204 provides the interface between the microwaves and the quartz tube 1224 within which the plasma is created. Plasma is formed within the plasma reaction chamber 1214, the region of the quartz tube 1224 within which the chemical transformations take place. As shown in cross-section in FIG. 12, the quartz tube 1224 is disposed within, but is separated from, the applicator 1204 by an air gap (not labeled).

When the plasma is off and the microwaves are on, a standing wave is formed in the applicator 1204 between the 3-stub tuner 1230 and a sliding shorting plate 1232 on the end of the applicator 1204, such that the electric field is sufficient to initiate breakdown of the gas molecules in the quartz tube. Microwave energy entering the applicator 1204 is tuned to peak at the center of the plasma reaction chamber 1214, using the shorting plate 1232 as needed to change the length of the plasma reaction chamber 1214 and using the 3-stub tuner 1230 to change the phase of the incoming microwaves. Once the plasma has been initiated, the stub locations in the tuner 1230 can be altered preferentially to match the microwave power to the plasma, minimizing un-absorbed power. The 3-stub tuner 1230 contains power and phase sensors (not shown) and can algorithmically adjust the motor-driven stubs to minimize un-absorbed power. A dual-directional coupler 1234, which contains two small pinholes that couple microwaves with a known attenuation, is included in the waveguide 1212 proximal to the 3-stub tuner 1230. Power meters (not shown) are connected to these pinhole ports and convert the microwave power into a voltage, outputting forward and reflected power measurements. A thin quartz window 1238 is added into the waveguide system to prevent environmental debris and dust from entering the waveguide components.

b. Torch System for Acetylene Production

In embodiments, a plasma-based hydrocarbon processing system for producing acetylene and hydrogen can be of any scale and can deliver a range of purities and acetylene concentrations, depending on the desired end use. Plasma-based hydrocarbon processing systems as described previously can be designed for small scale applications and can be adapted to the needs of the end user. To facilitate this customization, a plasma-based hydrocarbon processing system can be configured so that the outflow (effluent) stream from the reactor is separated into gas streams having different compositions, for example, a stream having a higher concentration of acetylene and a stream having a higher concentration of hydrogen. Small-scale plasma-based hydrocarbon processing systems can be designed to deliver pure gas streams, or they can deliver acetylene-hydrogen mixtures, with or without other gases included in the output gas flow. A small-scale system or "mini-unit" as described above can be designed to produce only acetylene-hydrogen mixtures in its reactor, with gas effluent varying from 0.5%-75% acetylene, therefore minimizing the amount of separation required and reducing the complexity of the system. In embodiments, the end user can manipulate the parameters of the separation subsystem to produce a desired composition of acetylene admixed with hydrogen; in embodiments, the parameters of the microwave plasma reactor module in the mini-unit can be adjusted as well, although for more extensive parameter customization, a larger unit is desirable.

In an embodiment, the overall size of the plasma-based hydrocarbon processing system can be scaled, for example from a smaller scale unit such as a table-sized mini-unit (e.g., 4 feet wide by 8 feet long by 4 feet tall) to a large-scale unit that is 20×20×20 feet or larger. In an embodiment, the plasma-based hydrocarbon processing system can be sized so that it is portable. Desirable sizing for a portable unit ranges from the table-sized dimensions (e.g., 4×8×4) to the size of a standard shipping container. While shipping containers vary in size, a standard 20-foot ISO shipping container size would allow transportation of a portable-sized unit; such containers are typically about 8 feet wide, 20 feet long, and 8.5 to 9.5 feet high. Other, smaller, shipping containers can be used for smaller portable devices, for example, those having lengths of 10 feet or 8 feet, combined with height and width dimensions as mentioned above.

Such a small-scale system can be attached to small end-user apparatus (e.g. welding torches such as acetylene or oxy-acetylene torches) or to small storage facilities or storage tanks. In an embodiment, a 5 kW plasma-based hydrocarbon processing system mini-unit with dimensions of 4 feet wide by 8 feet long by 4 feet tall can produce acetylene-hydrogen mixtures of greater than 50% acetylene, in an amount sufficient to feed at least 5 oxy-fuel cutting torches of concurrent, continuous use. In embodiments, power ranges for a plasma-based hydrocarbon processing system mini-unit can range from about 1 kW to about 500 kW, with power ranges selected for desired commercial uses. A plasma-based hydrocarbon processing system such as this can be designed to be portable. As described above, larger units, for example, up to the size of a standard ISO 20-foot shipping container, can also be designed to be portable. In embodiments, a portable plasma-based hydrocarbon processing system can be deployed to construction sites, demolition sites, shipyards, or remote operations like pipelines or offshore oil rigs, depending on the availability of a mixed gas stream such as natural gas or biogas, electricity, and water.

Figure 13:
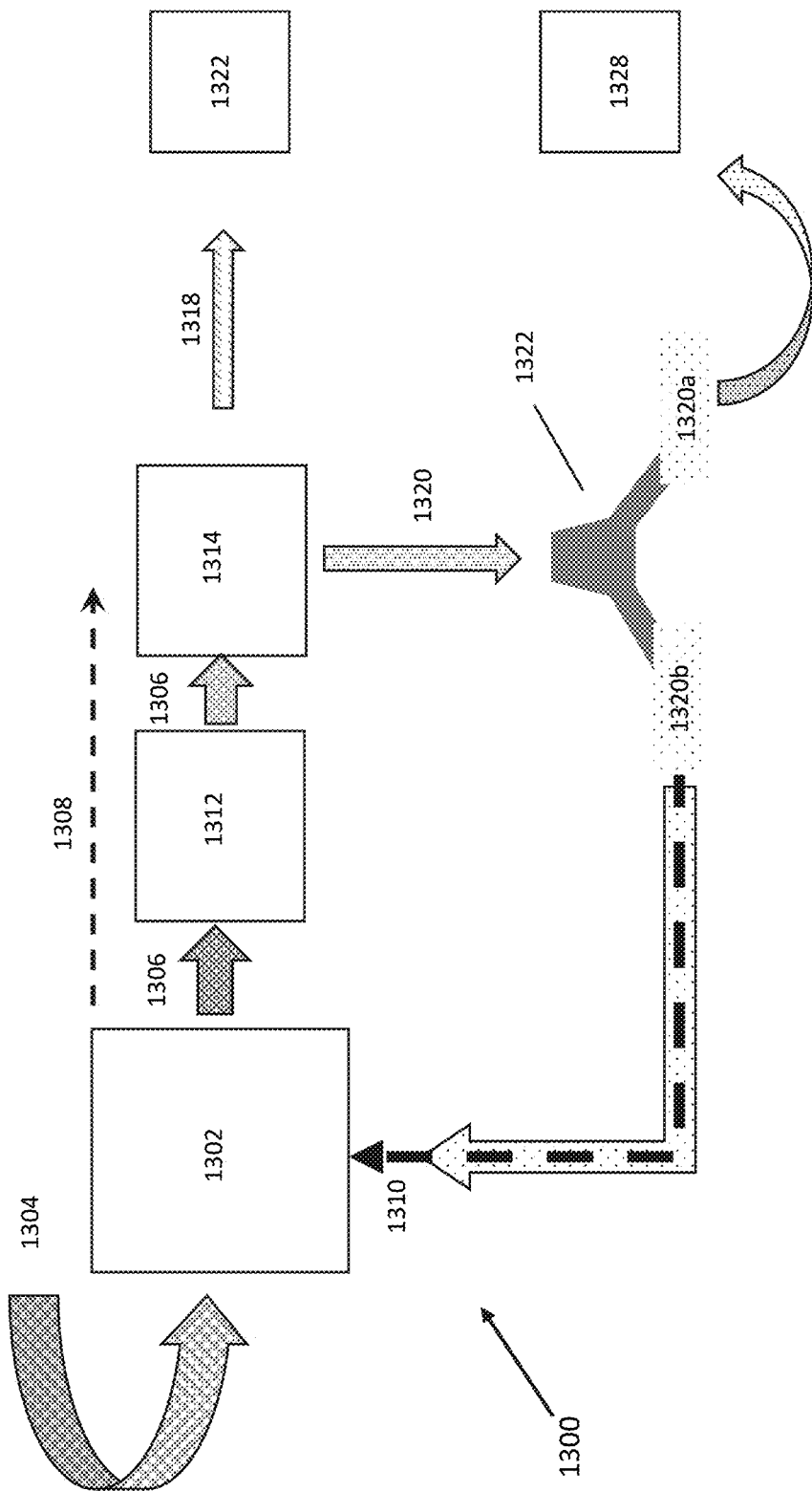
FIG. 13 is a block diagram of a small-scale system for gas processing.

FIG. 13 provides a block diagram of a small scale and scalable plasma-based hydrocarbon processing system 1300 suitable for industrial uses. As shown in FIG. 13, a plasma reactor 1302 substantially as described above has an input feed gas 1304 comprising a hydrocarbon such as methane, ethane, propane, butane, and the like, and derived from tanks or pipelines such as a natural gas line or a biogas tank or line. This input feed gas 1304 has a preselected inflow calibrated to produce an outflow (effluent) gas flow 1306 from the system 1300 ultimately suitable for a particular industrial purpose, for example metal cutting. In embodiments, an input feed gas 1304 such as methane or a methane-dense mixture such as natural gas or biogas can be used. In embodiments, a liquid source of an input feed gas 1304 such as propane or butane is advantageous, since such feed gas sources may be readily available in certain regions or facilities where a native gas source such as natural gas or biogas is not available.

In this Figure, the direction of gas flow is indicated by the arrow 1308 and other directional arrows. As an example of gas flows useful in the system 1300, a gas inflow within the range from about 0 to about 50 SLM can be selected; in an embodiment, a gas inflow of 5 SLM can produce a gas outflow of about 10 SLM. In embodiments, the input feed gas 1304 enters the plasma reactor 1302 as a sole gas input. In other embodiments, a separate gas input from a recycled gas stream 1310 enters the plasma reactor 1302 through a separate inflow nozzle (not shown), to be combined with the input feed gas 1304 within the plasma reactor 1302, for example using a gas injector (not shown) as described in previous Figures.

In an embodiment, the outflow 1306 from the plasma reactor 1302 contains about 14% acetylene, 84% hydrogen, and 2% methane, and it can be further processed by other components of the system. Entrained in the gaseous outflow 1306 are various carbon species byproducts, including higher-order carbon products and carbon particles, that can be removed prior to delivering a gas product to an end-user in certain embodiments. These byproducts can be removed in solid and liquid traps 1312, through which the outflow gas 1306 passes after being processed in the plasma reactor 1302. After the byproducts are removed, the gas stream 1306 is processed through a hydrogen separation membrane system 1314 or a pressure swing adsorber that removes hydrogen. Such processing allows an acetylene-rich stream 1318 to be separated from a hydrogen-rich stream 1320, with the acetylene-rich stream 1318 being available to the end-user for industrial purposes, e.g., metal cutting. In other embodiments, there is no advantage to removing the higher-order carbon products, for example if the gaseous effluent is to be used for welding or other industrial uses where a purified acetylene stream is unnecessary. However, it is understood that higher-order carbon products can foul hydrogen separation membranes, so that these species should be removed if a hydrogen separation membrane system is used; alternatively, if a mixed effluent stream that includes the higher-order carbon products is commercially advantageous, a hydrogen processing system such as a pressure swing adsorber can be used instead of a hydrogen separation membrane system.

As shown in the Figure, the acetylene-rich stream 1318, having been processed to remove higher-order carbon products and hydrogen, can be directed to various end uses or storage 1322. For example, the acetylene-rich stream 1318 can be directed into a pressurized tank, from which end-users can withdraw the gas mixture for use in metal cutting torches; advantageously, if the acetylene-rich stream 1318 is stored, the plasma-based hydrocarbon processing system can be run intermittently on an as-needed basis to fill the tank(s) for later use. In an embodiment, the acetylene-rich stream 1318 can contain about 50% acetylene, along with other components such as hydrogen, methane, and other gaseous additives as applicable. The acetylene-rich stream 1318 can be produced at a flow of about 2.1. SLM. In an embodiment, the hydrogen-rich stream 1320 can contain about 4% acetylene and 96% hydrogen, with a total flow of about 7.9 SLM. In embodiments, two or more separation membrane systems can be employed to increase the concentration of acetylene in the acetylene-rich product stream 1318, although a small-scale system can be designed with a single separation membrane system in order to limit the overall size of the apparatus.

In the plasma-based hydrocarbon processing system embodiment illustrated in FIG. 13, the hydrogen-rich stream 1320 can be directed through a splitter 1322, which can separate the hydrogen-rich stream 1320 into two substreams 1320a and 1320b, one (1320a) for end uses, disposal, and/or storage, and one (1320b) for recycling as a recycled gas stream 1310 into the plasma reactor 1302, where it can be processed along with the input feed gas 1304. The splitter 1322 can be formed from components familiar to those of skill in the art, such as Y-valves, mass flow controllers and the like. The hydrogen-rich substream 1320a that is not recycled can be vented, disposed of, collected, burned, or otherwise used, as required by the specific industrial setting.

The hydrogen-rich substream 1320b used for recycling can have the same composition as the substream 1320a that is directed to end uses, disposal, and/or storage. In an embodiment, a recycle flow 1310 of about 5 SLM can be redirected into the plasma reactor 1302, having a composition of about 97.5% hydrogen and 2.5% acetylene, yielding a recycle flow of about 5 SLM hydrogen. With a recycled stream 1310 combined with the input feed gas 1304 to fuel chemical transformations in the plasma reactor 1302, an outflow gas 1306 is produced, as described above. In embodiments, the proportion for recycling can be tuned, based on the user's requirements. For recycling, a mass flow controller that meters the amount of hydrogen-rich gas 1320b for recycling offers particular consistency, with the remainder directed to end-uses, disposal, or storage.

Figure 14:
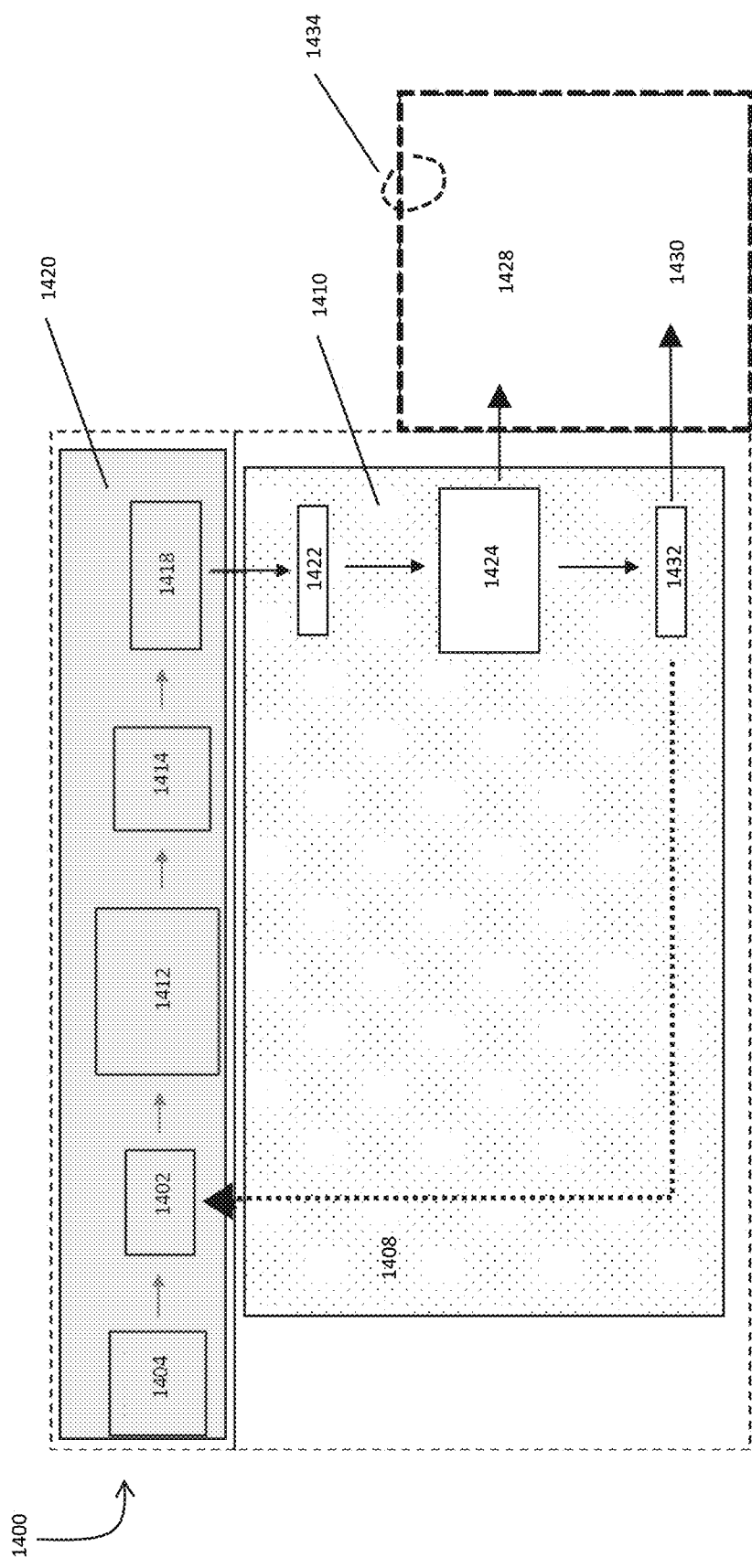
FIG. 14 is a block diagram of a small-scale system for gas processing.

FIG. 14 shows, in more detail, a modular plasma-based hydrocarbon processing system 1400 suitable for small-scale or larger-scale use, with arrows showing directions for gas flow. As shown in FIG. 14, a gas pipeline 1404, for example, a natural gas pipeline, can provide the inflow gas for the microwave plasma reactor 1402, although any source of inflow gas can be used (a supply tank containing the gas, for example, as would be available for $C_1$-$C_4$ alkanes, or a line or tank delivering biogas). The inflow gas can be supplemented by a recycled stream 1408 containing a hydrogen-rich gas. Following processing in the microwave plasma reactor 1402, the outflow (effluent) gas passes through a heavy liquids trap 1412 that removes the higher-order hydrocarbons using a combination of a cold trap and/or a carbon adsorber. As a next stage, the outflow gas passes through a filter 1414 that removes particulate matter, for example carbon soot. The gas pressure is then adjusted by a vacuum pump 1418 and then the gas is compressed by a compressor 1422 to pass through a hydrogen separator 1424. The plasma reactor 1402, the heavy liquids trap 1412, the solids filter 1414, and the vacuum pump 1418 are grouped together as the reactor subsystem 1420. This may be located in proximity to the hydrogen recycle subsystem 1410 and the effluent management subsystem 1434, or these subsystems can be in fluid communication with each other but arranged remotely from each other, as is convenient for a particular industrial application.

As mentioned previously, the hydrogen separator 1424 can include one or more hydrogen separation units; in an exemplary embodiment, each hydrogen separation unit can contain one or more hydrogen separation membranes, but other configurations and separator technologies (for example, pressure swing adsorber technology to separate hydrogen) can be employed. The configurations of the hydrogen separator units are adaptable to permit lesser or greater acetylene enrichment in the effluent acetylene-rich stream 1428. Depending on the desired industrial use, this effluent stream 1428 can be used directly as a cutting stream, or it can be stored as a product stream. In an embodiment, the gas remaining after the acetylene-rich stream 1424 is removed contains a large proportion of hydrogen. As previously described, this hydrogen-rich stream can be split into two substreams in a splitter 1432, with one stream 1408 designated for recycle, and one stream 1430 for disposal, venting, burning, commercialization, or other uses as desired.

Effluent management subsystems, substantially as described previously, can be integrated with the reactor subsystem (including a gas delivery subsystem, a microwave subsystem, and a vacuum subsystem, previously described but not shown in FIG. 14) within a single mini-unit for specific applications. The size, number, and complexity of the components required for the effluent separation processes can affect the size of the system overall. In an embodiment, a single plasma reactor can utilize a single hydrogen separation subsystem to provide a small footprint, with the subsystem including one or two hydrogen-separating membranes or other separation subsystem technologies, such as pressure swing adsorption. In an embodiment, separation subsystems, for example for hydrogen separation, can be integrated with the plasma-based hydrocarbon processing system.

In an embodiment of a modular plasma-based hydrocarbon processing system using a single hydrogen separation unit with a single separation membrane, the outflow gas from the reactor can contain the following gaseous components, at a flow rate of 10 SLM: 14% acetylene, 81% hydrogen, 2% methane, and 3% nitrogen. Following processing through a hydrogen separation unit having a single separation membrane, a hydrogen-rich stream is formed, containing the following gaseous components at a flow rate of 7 SLM: 4% acetylene, 96% hydrogen. Simultaneously, an acetylene-rich stream is formed, containing the following gaseous components at a flow rate of 3 SLM: 50% acetylene, 27% hydrogen, 9% methane, and 14% nitrogen. Using this process, 93.75% acetylene retention is accomplished in the acetylene-rich stream, and 86.5% of hydrogen is recycled. The flow rates and mol ratios of the components of the various gas streams for the one-membrane hydrogen separation system are shown in Table 3 below:

A wide variety of industrial uses can be envisioned for small scale or modular plasma-based hydrocarbon processing systems as described herein. As mentioned above, a major industrial use for acetylene is in the metalworking industry, for example, in metal cutting. For these purposes, an appropriately sized plasma-based hydrocarbon processing system in accordance with this disclosure can be used directly or via storage tanks to provide fuel for metal cutting. In addition, the plasma-based hydrocarbon processing system can be coupled with other systems to provide product versatility and to increase efficiency in the metalworking industry. As an example, in oxy-acetylene steel cutting facilities, the plasma-based hydrocarbon processing system can be used in conjunction with air separation units (ASUs). The ASU can separate air into nitrogen-rich and oxygen-rich streams, which can then be combined with the gas stream(s) used by or produced by microwave plasma reactor unit. Using this combination of apparatus, an operator can generate all the gas feedstock required for steel fabrication on-site.

TABLE 3

|  | Plasma Reactor Effluent | | Acetylene-rich stream | | Hydrogen-rich stream | | Vent/burn | | Recycle Stream | |
| --- | --- | --- | --- | --- | --- | --- | --- | --- | --- | --- |
|  | Flow Rate (SLM) | mol ratio | Flow Rate (SLM) | mol ratio | Flow Rate (SLM) | mol ratio | Flow Rate (SLM) | mol ratio | Flow Rate (SLM) | mol ratio |
| $H_2$ | 8.1 | 0.81 | 0.567 | 0.268 | 7.53 | 0.956 | 3.53 | 0.956 | 4 | 0.956 |
| $CH_4$ | 0.2 | 0.02 | 0.2 | 0.094 | 0 | 0 | 0 | 0 | 0 | 0 |
| $N_2$ | 0.3 | 0.03 | 0.3 | 0.142 | 0 | 0 | 0 | 0 | 0 | 0 |
| $C_2H_2$ | 1.4 | 0.14 | 1.05 | 0.496 | 0.35 | 0.044 | 0.164 | 0.044 | 0.186 | 0.044 |
| Total | 10 |  | 2.12 |  | 7.88 |  | 3.694 |  | 4.186 |  |

A double-membrane hydrogen separation unit can extract more hydrogen from the reactor's outflow gas, yielding a hydrogen-rich stream containing 1.2% acetylene and 98.8% hydrogen, at a flow of 7 SLM. With this system, an acetylene-rich stream is formed containing the following gaseous components at a flow rate of 3 SLM: 45% acetylene, 38% hydrogen, 7% methane, and 10% nitrogen. The flow rates and mol ratios of the components of the various gas streams for the two-membrane hydrogen separation system are shown in Table 4 below:

EXAMPLES

Example 1

A flow of precursor gas, comprised of 60 standard liters per minute of 99.9% purity methane, 90 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube

TABLE 4

|  | Plasma Reactor Effluent | | Acetylene-rich stream | | Hydrogen-rich stream | | Vent/burn | | Recycle Stream | |
| --- | --- | --- | --- | --- | --- | --- | --- | --- | --- | --- |
|  | Flow Rate (SLM) | mol ratio | Flow Rate (SLM) | mol ratio | Flow Rate (SLM) | mol ratio | Flow Rate (SLM) | mol ratio | Flow Rate (SLM) | mol ratio |
| H2 | 8.1 | 0.81 | 1.09 | 0.376 | 7.006 | 0.988 | 3.53 | 0.988 | 4 | 0.988 |
| CH4 | 0.2 | 0.02 | 0.2 | 0.069 | 0 | 0 | 0 | 0 | 0 | 0 |
| N2 | 0.3 | 0.03 | 0.3 | 0.103 | 0 | 0 | 0 | 0 | 0 | 0 |
| C2H2 | 1.4 | 0.14 | 1.05 | 0.452 | 0.088 | 0.012 | 0.038 | 0.012 | 0.05 | 0.012 |
| Total | 10 |  | 2.12 |  | 7.094 |  | 3.568 |  | 4.05 |  | kept at a pressure of 70 Torr. The precursor gas was subjected to 19 kW of incident 915 MHz microwave power in a plasma reactor apparatus similar to that described in FIG. 3. 95.7% of the methane contained in the precursor gas was converted to hydrogen and hydrocarbon products. The hydrocarbon composition of the outflow gas leaving the reactor is described in Table 5 below, as analyzed by a gas chromatograph.

TABLE 5

| Component | Mol % |
|---|---|
| Acetylene | 15.12 |
| Hydrogen | 82.97 |
| Methane | 1.41 |
| Ethylene | 0.14 |
| Propane | 0.01 |
| Propadiene | 0.01 |
| Diacetylene | 0.29 |
| Vinyl Acetylene | 0.03 |
| Benzene | 0.02 |
| Carbon Solids and higher-order hydrocarbons | Trace |

The outflow gas from the reactor was passed through an air-cooled heat sink and then passed through corrugated-paper filters before exiting the vacuum pump. The outflow gas then passed through a cold trap operating at 10° C. and additional filter.

A portion of outflow gas was then passed through an adsorption column containing high surface area activated carbon. Outflow gas composition at the adsorption column exit is shown in Table 6 below.

TABLE 6

| Component | Mol Percent before Adsorption | Mol Percent after Adsorption |
|---|---|---|
| Acetylene | 15.12 | 15.17 |
| Hydrogen | 82.97 | 83.25 |
| Methane | 1.41 | 1.41 |
| Ethylene | 0.14 | 0.14 |
| Propane | 0.01 | 0.1 |
| Propadiene | 0.01 | 0.1 |
| Diacetylene | 0.29 | 0 |
| Vinyl Acetylene | 0.03 | 0 |
| Benzene | 0.02 | 0 |
| Carbon Solids | Trace | 0 |
| Higher Order Hydrocarbons | Trace | 0 |

After leaving the adsorption column, a portion of the outflow gas was then passed through an absorption column. A solvent, N-Methyl pyrrolidone, was flowed counter-currently to the outflow gas to preferentially absorb acetylene. Exiting the absorption column, the solvent with the absorbed acetylene was pumped into a second column for restoring the solvent and heated to 120-140° C. In the second column, the acetylene and associated gases were removed from the solvent as a purified product gas stream and the restored solvent was recycled into the system. Table 7 below shows the composition of the purified product gas stream emanating from the second column.

TABLE 7

| Component | Mol Percent |
|---|---|
| Acetylene | 98.764 |
| Hydrogen | 0.774 |
| Methane | 0.211 |
| Ethylene | 0.083 |

TABLE 7-continued

| Component | Mol Percent |
|---|---|
| Ethane | 0.002 |
| Propylene | 0.042 |
| Diacetylene | 0.002 |
| Vinyl Acetylene | 0.006 |
| Carbon Dioxide | 0.115 |
| Toluene | 0.001 |

Example 2

A flow of precursor gas, comprised of 20 standard liters per minute of 99.9% purity methane, 20 standard liters per minute of ethane, 95 standard liters per minute of 99.9% purity hydrogen, and 6 standard liters per minute of nitrogen was supplied through a plasma reactor apparatus as described in Example 1 and reacted with 18 kW of incident 915 MHz microwave power using the plasma reactor apparatus used in Example 1. 97.9% of the methane and ethane contained feed gas was converted to hydrogen and hydrocarbon products. The hydrocarbon composition of the outflow gas from the reactor is described in Table 8 below, as analyzed by a gas chromatograph.

TABLE 8

| Component | Mol % |
|---|---|
| Acetylene | 16.70 |
| Hydrogen | 72.73 |
| Methane | 0.75 |
| Ethylene | 0.35 |
| Propane | 0.01 |
| Propadiene | 0.01 |
| Diacetylene | 0.38 |
| Vinyl Acetylene | 0.05 |
| Benzene | 0.03 |
| Carbon Solids Higher-Order HCs | Trace |

Example 3

A flow of precursor gas, comprised of 110 standard liters per minute of 99.9% purity methane and 11 standard liters per minute of nitrogen, was supplied through a gas injector apparatus, similar to that described in FIGS. 4A and 4B, into an 80 mm outer diameter, 75 mm inner diameter quartz tube. The precursor gas was subjected to 11 kW of incident 915 MHz microwave power in a plasma reactor apparatus as described in FIG. 3. 50.7% of the methane contained in the precursor gas was converted to hydrogen and hydrocarbon products. 7% of the converted methane yielded carbon solids and polycyclic aromatic hydrocarbons. 76% of the converted methane yielded acetylene.

Example 4

A flow of precursor gas, comprised of 100 standard liters per minute of 99.9% purity methane, 160 standard liters per minute of 99.9% purity hydrogen, and 10 standard liters per minute of nitrogen, was supplied through a gas injector apparatus similar to that described in FIGS. 4A and 4B, into an 50 mm outer diameter, 45 mm inner diameter quartz tube kept at 70 Torr. The precursor gas was subjected to 29 kW of incident 915 MHz microwave power in a plasma reactor apparatus similar to that described in FIG. 3. 90.3% of the methane contained in the precursor gas was converted to hydrogen and hydrocarbon products. The hydrocarbon composition of the outflow gas leaving the reactor is described in Table 9 below.

TABLE 9

| Component | Mol % |
| --- | --- |
| Hydrogen | 83.42729 |
| Methane | 2.99563 |
| Propane | 0.010008 |
| Propylene | 0.010008 |
| Propadiene | 0.060046 |
| Methyl Acetylene | 0.010008 |
| 1,3-butadiene | 0 |
| Vinyl Acetylene | 0.020015 |
| Diacetylene | 0.253528 |
| Ethylene | 0.143443 |
| Ethane | 0 |
| Acetylene | 13.05334 |
| Benzene | 0.016679 |
| Toluene | 0 |

Example 5

A flow of precursor gas, comprised of 130 standard liters per minute of 99.9% purity methane, and 13 standard liters per minute of nitrogen, was supplied through a gas injector apparatus similar to that described in FIGS. 4a and 4b, into an 80 mm outer diameter, 75 mm inner diameter quartz tube kept at 48 Torr. The precursor gas was subjected to 24.3 kW of incident 915 MHz microwave power in a plasma reactor apparatus similar to that described in FIG. 3. 85.2% of the methane contained in the precursor gas was converted to hydrogen and hydrocarbon products.

Example 6

A flow of precursor gas, comprised of 74 standard liters per minute of 99.9% purity methane, 40 standard liters per minute of 99.9% purity hydrogen, and 88 standard liters per minute of nitrogen, was supplied through a gas injector apparatus similar to that described in FIGS. 4A and 4B, into an 80 mm outer diameter, 75 mm inner diameter quartz tube kept at 70 Torr. The precursor gas was subjected to 23.9 kW of incident 915 MHz microwave power in a plasma reactor apparatus similar to that described in FIG. 3. 95.1% of the methane contained in the precursor gas was converted to hydrogen and hydrocarbon products.

Example 7

A flow of precursor gas, comprised of 47 standard liters per minute of 99.9% purity methane, 110 standard liters per minute of 99.9% purity hydrogen, and 5 standard liters per minute of nitrogen, was supplied through a gas injector apparatus similar to that described in FIGS. 4a and 4b, into an 80 mm outer diameter, 75 mm inner diameter quartz tube kept at 65 Torr. The precursor gas was subjected to 15.6 kW of incident 915 MHz microwave power in a plasma reactor apparatus similar to that described in FIG. 3. 89.7% of the methane contained in the precursor gas was converted to hydrogen and hydrocarbon products.

Example 8

A flow of precursor gas, comprised of 90 standard liters per minute of 99.9% purity methane, 135 standard liters per minute of 99.9% purity hydrogen, and 9 standard liters per minute of nitrogen, was supplied through a gas injector apparatus similar to that described in FIGS. 4A and 4B, into an 38 mm outer diameter, 35 mm inner diameter quartz tube kept at 105 Torr. The precursor gas was subjected to 25 kW of incident 915 MHz microwave power in a plasma reactor apparatus similar to that described in FIG. 3. 92.0% of the methane contained in the precursor gas was converted to hydrogen and hydrocarbon products.

Example 9

A flow of precursor gas, comprised of 15 standard liters per minute of 99.9% purity butane, 90 standard liters per minute of 99.9% purity hydrogen, and 6 standard liters per minute of nitrogen, was supplied through a gas injector apparatus similar to that described in FIGS. 4a and 4b, into an 50 mm outer diameter, 45 mm inner diameter quartz tube kept at 50 Torr. The precursor gas was subjected to 17.7 kW of incident 915 MHz microwave power in a plasma reactor apparatus similar to that described in FIG. 3. 100% of the butane contained in the precursor gas was converted to hydrogen and hydrocarbon products with a 0.6% methane yield.

Example 10

A flow of precursor gas, comprised of 30 standard liters per minute of 99.9% purity ethane, 90 standard liters per minute of 99.9% purity hydrogen, and 6 standard liters per minute of nitrogen, was supplied through a gas injector apparatus similar to that described in FIGS. 4a and 4b, into an 50 mm outer diameter, 45 mm inner diameter quartz tube kept at 126 Torr. The precursor gas was subjected to 16 kW of incident 915 MHz microwave power in a plasma reactor apparatus similar to that described in FIG. 3. 100% of the ethane contained in the precursor gas was converted to hydrogen and hydrocarbon products with 3.3% methane yield. The hydrocarbon composition of the outflow gas leaving the reactor is described in Table 10 below.

TABLE 10

| Component | Mol % |
| --- | --- |
| acetylene | 18.34358 |
| hydrogen | 79.93364 |
| methane | 0.824195 |
| ethane | 0.003651 |
| ethylene | 0.383346 |
| propane | 0.006845 |
| propadiene | 0.008215 |
| propylene | 0 |
| diacetylene | 0.412097 |
| vinyl acetylene | 0.054307 |
| methyl acetylene | 0 |
| benzene | 0.028751 |
| toluene | 0.001369 |

Example 11

A flow of precursor gas, comprised of 8.6 standard liters per minute of 99.9% purity propane, 8.6 standard liters per minute of 99.9% purity butane, 88 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube kept at 70 Torr. The precursor gas was subjected to 16 kW of incident 915 MHz microwave power in a plasma reactor apparatus similar to that described in FIG. 3. 100% of the ethane contained in the precursor gas was converted to hydrogen and hydrocarbon products with a 3.2% methane yield. The hydrocarbon composition of the outflow gas leaving the reactor is described in Table 11 below.

TABLE 11

| Component | Mol % |
|---|---|
| acetylene | 20.33077 |
| hydrogen | 77.56967 |
| methane | 1.155769 |
| ethane | 0 |
| ethylene | 0.293664 |
| propane | 0.008498 |
| propadiene | 0.013692 |
| propylene | 0 |
| diacetylene | 0.549557 |
| vinyl acetylene | 0.046269 |
| methyl acetylene | 0 |
| benzene | 0.030688 |
| toluene | 0.001416 |

Example 12

A plasma reactor system as described in Example 1 that produces 250 liters of outflow gas per minute was used. After the vacuum pump in the system, solid carbon byproducts were removed with a simple in-line filter. Liquid hydrocarbon condensates containing greater than 14 carbon atoms were separated from the stream in a cold trap operating at −20° C. No further hydrocarbons were removed, and the outflow was directly passed through a stainless-steel vessel with an internal diameter of 8 inches containing 0.4 kg of blank 100-200 mesh α-alumina mixed with 1.8 kg of 100-200 mesh α-alumina doped with 3 wt % metallic palladium and 4 wt % metallic silver. The catalyst bed was maintained at 350° C. with internal, open-loop water cooling system. A gas mixture was obtained that contains 50% hydrogen, 11% ethylene, 0.5% ethane and 38.5% methane; acetylene content in the gas mixture was deliberately kept below 100 ppm.

Example 13

A plasma reactor system as described in Example 1 was used. A stream of 1 liter of outflow gas per minute was split off and processed further as described in this example. After the vacuum pump, solid carbon byproducts were removed with a ceramic, regenerative filter. Liquid hydrocarbon condensates containing greater than 10 carbon atoms were separated from the stream in a cold trap operating at −30° C. Afterwards, the outflow gas was passed through a stainless-steel vessel containing 20 grams high-surface area activated carbon, doped with 0.01% metallic palladium. The outflow gas at this point contained 85% hydrogen, 8% acetylene, 4% ethylene, and 0.6% vinyl acetylene and balance methane. The vinyl acetylene was removed by bubbling through a 500 mL vessel containing 300 mL of concentrated sulfuric acid at room temperature, then through a vessel containing 100 mL room temperature water to trap the volatized sulfuric acid. Finally, the gas stream was dried by passing through 10 grams of calcium sulfate desiccant.

While this invention has been particularly shown and described with references to preferred embodiments thereof, it will be understood by those skilled in the art that various changes in form and details may be made therein without departing from the scope of the invention encompassed by the appended claims. Unless otherwise indicated, all numbers expressing reaction conditions, quantities, amounts, ranges and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. A method for processing a methane-containing inflow gas to produce acetylene gas, comprising directing reactants into a system comprising: a gas delivery subsystem, a plasma reaction chamber, a microwave subsystem, and an effluent separation and disposal subsystem;

i. wherein the gas delivery subsystem is in fluid communication with the plasma reaction chamber and directs the reactants into the plasma reaction chamber; the gas delivery subsystem comprising a delivery conduit and a gas injector, wherein the reactants consist of gaseous reactants, wherein the gaseous reactants comprise the methane-containing inflow gas and a hydrogen-rich reactant gas;

wherein the gas injector comprises an injector body comprising two or more separate gas feeds, a first gas feed conveying the methane-containing inflow gas into the plasma reaction chamber through a first set of one or more nozzles, and a second gas feed conveying the hydrogen-rich reactant gas into the plasma reaction chamber through a second set of one or more nozzles, wherein the delivery conduit is in fluid communication with the gas injector, wherein the delivery conduit comprises a feed gas conveying circuit that delivers the methane-containing inflow gas into the gas injector, and wherein the delivery conduit further comprises an auxiliary gas conveying circuit that delivers the hydrogen-rich reactant gas into the gas injector, each of the methane-containing inflow gas and the hydrogen-rich reactant gas being delivered into the gas injector, through the gas injector, and into the plasma reaction chamber through a separate pathway; and wherein the gas delivery subsystem conveys the methane-containing inflow gas and the hydrogen-rich reactant gas into the plasma reaction chamber such that the ratio of the methane to the hydrogen is about 1:1 to about 1:3;

ii. wherein the plasma reaction chamber is disposed within an elongate reactor tube, the elongate reactor tube having a proximal end and a distal end and being dimensionally adapted for interaction with the microwave subsystem, iii. wherein the microwave subsystem comprises an applicator that interacts with the elongate reactor tube by directing microwave energy into the plasma reaction chamber, wherein the plasma reaction chamber is disposed in a region of the elongate reactor tube that passes through the applicator and intersects it perpendicularly, and wherein the microwave subsystem produces the microwave energy and directs the microwave energy into the plasma reaction chamber to energize the methane-containing inflow gas and the hydrogen-rich reactant gas within the region of the elongate reactor tube to form a non-thermal plasma, and wherein the non-thermal plasma transforms the methane in the methane-containing inflow gas and the hydrogen in the hydrogen-rich reactant gas into outflow gas products, wherein the outflow gas products comprise the acetylene gas and hydrogen;

wherein the outflow gas products flow within the plasma reaction chamber towards the distal end of the elongate reactor tube and emerge from the distal end to form an effluent stream that enters the effluent separation and disposal subsystem in fluid communication with the elongate reactor tube, and iv. wherein the effluent separation and disposal subsystem comprises at least one of a hydrogen separation subsystem for removing hydrogen from the effluent stream, an acetylene separation subsystem for removing acetylene from the effluent stream, and an absorption column for removing higher hydrocarbons from the effluent stream.

2. The method of claim 1, wherein the hydrogen-rich reactant gas comprises a recycled gas formed from a portion of the outflow gas products, wherein the recycled gas is delivered through a recycled gas conveying circuit into the auxiliary gas conveying circuit to form at least a portion of the hydrogen-rich reactant gas that enters into the gas injector.

3. The method of claim 1, wherein the hydrogen-rich reactant gas consists essentially of hydrogen.

4. The method of claim 1, wherein the elongate reactor tube comprises a proximal portion at the proximal end, wherein the gas injector conveys the methane-containing inflow gas, and the hydrogen-rich reactant gas into the proximal portion and the methane-containing inflow gas and the hydrogen-rich reactant gas flow distally therefrom towards the plasma reaction chamber.

5. The method of claim 1, wherein at least one of the one or more nozzles in the first set of one or more nozzles or the second set of one or more nozzles is oriented at an angle to a longitudinal axis of the plasma reaction chamber or at an angle to a transverse axis of the plasma reaction chamber.

6. The method of claim 1, wherein at least one of the one or more nozzles in the first set of one or more nozzles or the second set of one or more nozzles is oriented at an angle to a longitudinal axis or a transverse axis of the injector body.

7. The method of claim 1, wherein the methane-containing inflow gas entering the plasma reaction chamber from the first set of one or more nozzles and the hydrogen-rich reactant gas entering the plasma reaction chamber from the second set of one or more nozzles create a vortex of the gases within the plasma reaction chamber.

8. The method of claim 1, wherein the hydrogen separation subsystem is downstream from the acetylene separation subsystem and in fluid communication therewith.

9. The method of claim 1, wherein the hydrogen separation subsystem is in fluid communication with a recycled gas conveying circuit, wherein at least a portion of the hydrogen removed from the effluent stream by the hydrogen separation subsystem is recycled into the recycled gas conveying circuit into the auxiliary gas conveying circuit to form at least a portion of the hydrogen-rich reactant gas that enters into the gas injector.

10. The method of claim 1, wherein the hydrogen separation subsystem is downstream from the acetylene separation subsystem.

11. The method of claim 1, wherein the effluent separation and disposal subsystem comprises at least two of the following: the hydrogen separation subsystem for removing hydrogen from the effluent stream, the acetylene separation subsystem for removing acetylene from the effluent stream, and the absorption column for removing higher hydrocarbons from the effluent stream.

12. The method of claim 1, wherein the effluent separation and disposal subsystem comprises the hydrogen separation subsystem for removing hydrogen from the effluent stream, the acetylene separation subsystem for removing acetylene from the effluent stream, and the absorption column for removing higher hydrocarbons from the effluent stream.

13. The method of claim 1, wherein the effluent separation and disposal subsystem further comprises a filter for removal of carbon solids upstream of the acetylene separation subsystem.

14. The method of claim 1, wherein the effluent separation and disposal subsystem further comprises a cold trap for removing higher order hydrocarbons as condensates.

15. The method of claim 14, wherein the hydrogen separation subsystem is downstream from the acetylene separation subsystem.

16. The method of claim 1, wherein the ratio is about 1:1-2.

17. The method of claim 1, wherein the ratio is about 1:1.5.

18. The method of claim 1, wherein the gaseous reactants consist of the methane-containing inflow gas and the hydrogen-rich reactant gas.

* * * * *